US 12,098,387 B2

(12) United States Patent
Cheng

(10) Patent No.: US 12,098,387 B2
(45) Date of Patent: Sep. 24, 2024

(54) METHODS FOR GENERATING ENGINEERED HUMAN PRIMARY BLOOD DENDRITIC CELL LINES

(71) Applicant: University of Maryland, Baltimore, Baltimore, MD (US)

(72) Inventor: Hua Cheng, Cooksville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 1710 days.

(21) Appl. No.: 15/769,241

(22) PCT Filed: Oct. 19, 2016

(86) PCT No.: PCT/US2016/057750
§ 371 (c)(1),
(2) Date: Apr. 18, 2018

(87) PCT Pub. No.: WO2017/070237
PCT Pub. Date: Apr. 27, 2017

(65) Prior Publication Data
US 2018/0305666 A1   Oct. 25, 2018

Related U.S. Application Data

(60) Provisional application No. 62/243,177, filed on Oct. 19, 2015.

(51) Int. Cl.
| | | |
|---|---|---|
| *C12N 5/0784* | (2010.01) | |
| *A61K 35/15* | (2015.01) | |
| *A61K 39/00* | (2006.01) | |
| *A61K 39/395* | (2006.01) | |
| *A61P 35/02* | (2006.01) | |
| *C07K 14/005* | (2006.01) | |
| *C07K 14/15* | (2006.01) | |
| *C07K 14/47* | (2006.01) | |
| *C12N 9/12* | (2006.01) | |
| *C12N 15/86* | (2006.01) | |

(52) U.S. Cl.
CPC ............ *C12N 5/0639* (2013.01); *A61K 35/15* (2013.01); *A61K 39/0011* (2013.01); *A61K 39/395* (2013.01); *A61P 35/02* (2018.01); *C07K 14/005* (2013.01); *C07K 14/15* (2013.01); *C07K 14/4703* (2013.01); *C12N 9/1276* (2013.01); *C12N 15/86* (2013.01); *C07K 2319/00* (2013.01); *C12N 2510/00* (2013.01); *C12N 2740/14022* (2013.01); *C12N 2740/16043* (2013.01)

(58) Field of Classification Search
None
See application file for complete search history.

(56) References Cited

U.S. PATENT DOCUMENTS

| | | |
|---|---|---|
| 4,722,848 A | 2/1988 | Paoletti |
| 6,916,642 B1 | 7/2005 | Kilian |
| 8,877,182 B2 | 11/2014 | Alici |
| 2003/0204069 A1 | 10/2003 | Morin |
| 2004/0253574 A1 | 12/2004 | Schuler |
| 2006/0067944 A1 | 3/2006 | Le Buannec |
| 2008/0090778 A1 | 4/2008 | Scarselli |
| 2009/0098090 A1 | 4/2009 | Hart |

FOREIGN PATENT DOCUMENTS

| | | |
|---|---|---|
| JP | 11509411 A | 8/1999 |
| JP | 2013256454 A | 12/2013 |
| JP | 2014239681 A | 12/2014 |
| JP | 2015529219 A | 10/2015 |
| WO | 9703186 | 1/1997 |
| WO | 2009111396 A1 | 9/2009 |
| WO | 2015067781 A1 | 5/2015 |

OTHER PUBLICATIONS

Jain, P. et al, J Leukoc. Biol., vol. 82, 2007, 28 pages.*
Besson, S. et al., Mol Ther., 2023, vol. 28: pp. 76-89.*
Mildner et al,. Development and function of dendritic cell subsets, Immunity, 40:642-656 (2014).
Osugi et al., Myeloid blood CD11c+ dendritic cells and monocyte-derived dendritic cells differ in their ability to stimulate T lymphocytes, Blood, 100:2858-2866 (2002).
Jongbloed et al., Human CD141+ (BDCA-3)+ dendritic cells (DCs) represent a unique myeloid DC subset that cross-presents necrotic cell antigens, The Journal of Experimental Medicine, 207:1247-1260 (2010).
Kvistborg et al., Fast generation of dendritic cells, Cellular immunology, 260:56-62 (2009).
Saskia et al., Human dendritic cell line models for DC differentiation and clinical DC vaccination studies, Journal of Leukocyte Biology, 84:1364-1373 (2008).
Ciminale et al., HTLV-1 and HTLV-2: highly similar viruses with distinct oncogenic properties, Front. Microbiol, 5:1-9 (2014).
Azran et al., Role of Tax protein in human T-cell leukemia virus type-I leukemogenicity, Retrovirology, 1:20 (2004).
Jones et al., Cell-free HTLV-1 infects dendritic cells leading to transmission and transformation of CD4+ T cells, Nature medicine, 14:429-436 (2008).
Kobayashi et al., TRAF6 is a critical factor for dendritic cell maturation and development, Immunity, 19:353-363 (2003).
Childs et al., Therapeutic approaches to enhance natural killer cell cytotoxicity against cancer: the force awakens, Nature Reviews Drug Discovery, 14:487-498 (2015).

(Continued)

*Primary Examiner* — Michael D Burkhart
(74) *Attorney, Agent, or Firm* — Nevrivy Patent Law Group P.L.L.C.

(57) ABSTRACT

Provided are engineered primary blood and monocyte-derived dendritic cells, wherein the dendritic cell expresses a functional Tax protein from a T cell leukemia virus, and methods of making and using the same.

15 Claims, 41 Drawing Sheets

Specification includes a Sequence Listing.

(56) References Cited

OTHER PUBLICATIONS

Cornetta et al., No Retroviremia or Pathology in Long-Term Follow-Up of Monkeys Exposed to a Murine Amphotropic Retrovirus, Hum. Gene Therapy, 2:215-219 (1991).
Kolberg et al., Gene-transfer virus contaminant linked to monkeys' cancer, J. Nih Res, 4:43 (1992).
Miller et al., Gene Transfer by Retrovirus Vectors Occurs Only in Cells That Are Actively Replicating at the Time of Infection, Mol. Cell. Biol., 10:4239-4242 (1990).
Naldini et al., In Vivo Gene Delivery and Stable Transduction of Nondividing Cells by a Lentiviral Vector, Science, 272:263-267 (1996).
Steinman, The Dendritic Cell System and its Role in Immunogenicity, Ann. Rev. Immunol., 9:271-296 (1991).
Woodhead et al., Novel Molecular Mechanisms of Dendritic cell-induced T cell activation, International Immunol, 12:1051-1061 (2000).
International Search Report from Appl. No. PCT/US16/57750, dated Mar. 31, 2017.
Moulon et al., T Cell Receptor Transfection Shows Non-HLA-Restricted Recognition of Nickel by CD8+ Human T Cells to be Mediated by αβ T Cell Receptors, The Society for investigative Dermatology, 121:496-501 (2003).
Pievani et al., Dual-functional Capability of CD3+CD56+ CIK Cells, a T-cell Subset that Acquires NK Function and Retains TCR-mediated Specific Cytotoxicity. Immunobiology, 118:3301-3310 (2011).
Ganchi et al., IkB/MAD-3 Masks the Nuclear Localization Signal of NF-kB p65 and Requires the Transactivation Domain to Inhibit NF-kB p65 DNA binding. Molecular Biology of the Cell. 3:1339-1352 (1992).
Mostoller et a., Human T-cell Leukemia Virus Type1 Tax Induces the Expression of Dendritic Cell Markers Associated with Maturation and Activation, Journal of Virology, 10:358-371 (2004).
Manuel et al., Dendritic Cells in Autoimmune diseases and Neuroinflammatory Disorders, Frontiers in Bioscience, 12:4315-4335 (2007).
Pooja et al., DC-SIGN Mediates Cell-Free Infection and Transmission of Human T-Cell Lymphotropic Virus Type 1 by Dendritic Cells, J Virol, (2009), 83:10908-10921.
Jones et al., Cell-free HTLV-1 infects dendritic cells leading to transmission and transformation of CD4+ T Cells, Nat. Med., (2008), 14:429-436.
Pievani et al., Dual-Functional capability of CD3+ CD56+ CIK cells, a T-Cell subset that acquires NK function and retains TCR-mediated specific cytotoxicity, Blood, (2011), 118:3301-3310.
Akagi el al., Increased protein tyrosine-phosphorylation in primary T-cell transduced with Taxl of Human T-cell leukemia virus type I, FEBS lett., (1995), 358: 34-38.
Japanese Office Action from Appl. No. 2018-520135, dated Dec. 1, 2020.
English translation of Japanesse Office action from Appl. No. 2018-520135, dated Dec. 1, 2020.
European Communication from Appl. No. EP16858151, dated Feb. 25, 2019.
Jain et al., DC-SIGN Mediates Cell-Free Infection and Transmission of Human T-Cell Lymphotropic Virus Type 1 by Dendritic Cells, Journal of Virology, 83:10908-10921 (2009).
Jain et al., Modulation of dendritic cell maturation and function by the Tax protein of human T cell leukemia virus type 1, Journal of Leukoeyte Biology, 82:44-56 (2007).
Richter et al., Generation of Inducible Immortalized Dendritic Cells with Proper Immune Function In Vitro and In Vivo, PLoS ONE, 8:1-12, e62621 (2013).
Santegoets et al., In vitro priming of tumor-specific cytotoxic T lymphocytes using allogeneic dendritic cells derived from the human MUTZ-3 cell line, Cancer Immunol Immunother, 55:1480-1490 (2006).
Wu et al., Induction of antitumor cytotoxic lymphocytes using engineered human primary blood dendritic cells, PNAS, 115:E4453-E4462 (2018).
Chinese Office Action from Appl. No. 201680070294.2, dated May 31, 2021.
English translation of Chinese Office action from Appl. No. 201680070294.2, dated May 31, 2021.
Jain et al., DC-SIGN Mediates Cell-Free Infection and Transmission of Human T-Cell Lymphotropic Virus Type 1 by Dendirtic Cells, Journal of Virology, (2009), p. 10908-10921.
Jain et al., Modulation of dendritic cell maturation and function by the Tax protein of human T cell leukemia virus type 1, J Leukoc Biol., (2007), 82:44-56.
Japanese pre-trial Examination from Appl. No. 2018-520135, dated Jun. 15, 2022.
Translation of Japanese pre-trial Examination from Appl. No. 2018-520135, dated Jun. 15, 2022.
Chinese Office Action from Appl. No. 201680070294.2, mailed on Feb. 16, 2022.
English translation of Chinese Office Action from Appl. No. 201680070294.2, mailed on Feb. 16, 2022.
European Office Action from Appl. No. 16858151.0, mailed on Dec. 9, 2021.
Mostoller et al., Human T-cell leukemia virus type I Tax induces the expression of dendritic cell markers associated with maturation and activation, Journal of NeuroVirology, (2004), 10:358-371.
Mostoller et al., Human T-cell leukemia virus type I Tax induces the expression of dendritic cell markers associated with maturation and activation, J Neurovirol, (2004)10:358-371.
Manuel et al., Dendritic cells in autoimmune diseases and neuroinflammatory disorders, Frontiers in Biosci., May 1, 2007, vol. 12, pp. 4315-4335.
Japanese Office Action from Appl. No. 201680070294.2, dated Oct. 5, 2021.
English translation of Japanese Office Action from Appl. No. 201680070294.2, dated Oct. 5, 2021.
Abstract of Japanese Patent Appl. No. JPH11509411A.
Santegoets et al., In vitro priming of tumor-specific cytotoxic T lymphocytes using allogeneic dendritic cells derived from the human MUTZ-3 cell line, Cancer Immunol Immunother, (2006), 55:1480-1490.
Cabannes et al., Mutations in the IkBa gene in Hodgkin's disease suggest a tumour suppressor role for IKBx, Oncogene, (1999), 18:3063-3070.
Immunology and Allergology in Otolaryngology, (2013), 31:237-246.
Official Communication from European Appl. No. 16858151.0, dated Feb. 10, 2020.
Abstract of Japanese Patent Appl. No. JP2013256454A.
Abstract of Japanese Patent Appl. No. JP2015529219A.
Abstract of Japanese Patent Appl. No. JP2014239681A.
Japanese Office Action from Appl. No. 2018-520135, mailed on Nov. 14, 2023.
Japanese Office Action from Appl. No. 2022-017157, mailed on Jan. 9, 2024.
English translation of Japanese Office action from Appl. No. 2022-017157, mailed on Jan. 9, 2024.
Romanelli et al., Highlights on distinctive structural and funtional properties of HTLV Taxproteins, Frontiers in Microbiology,(2013), 271:1-14.
Currer et al., HTLVTax: a fascinating multifunctional co-regulator of viral and cellular pathways, Frontiers in Microbiology, (2013), 406:1-24.

\* cited by examiner

EMSA

FIG. 3B

FIG. 5B
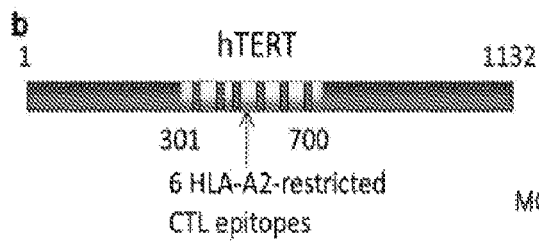
FIG. 5C
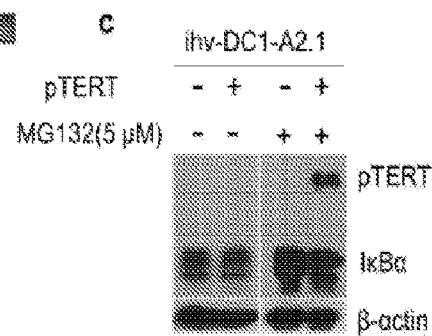
FIG. 5D
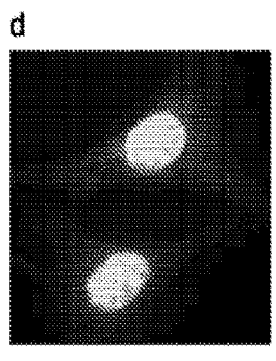
FLAG-TERT (aa301-700)
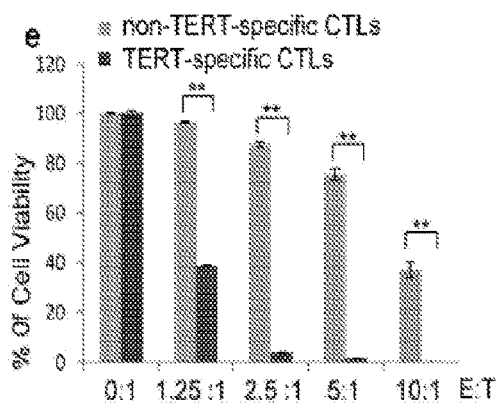
FIG. 5E
FIG. 5F
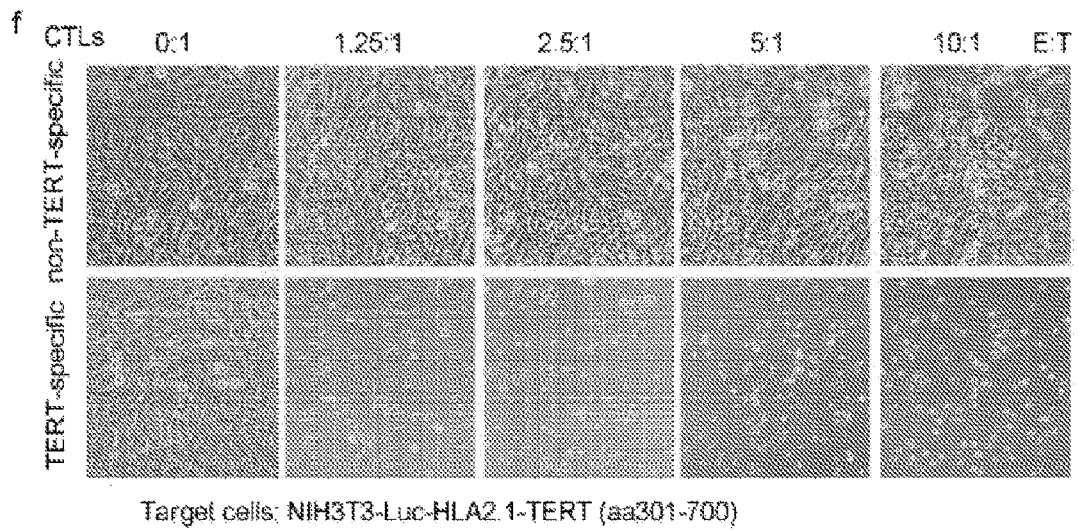
Target cells: NIH3T3-Luc-HLA2.1-TERT (aa301-700)

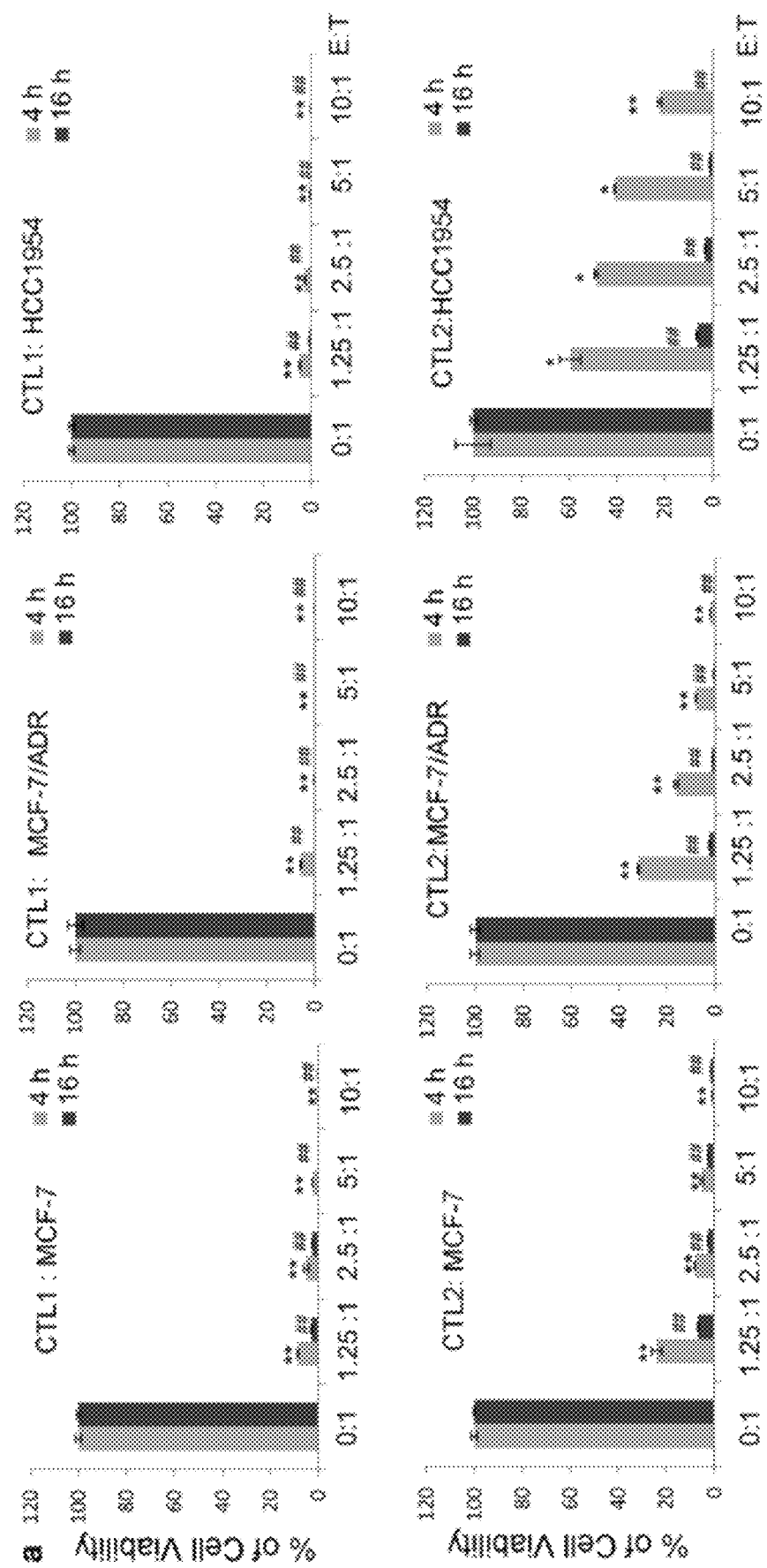

FIG. 9B
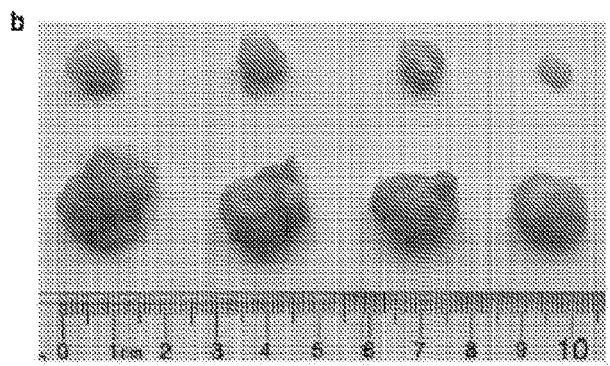
FIG. 9C
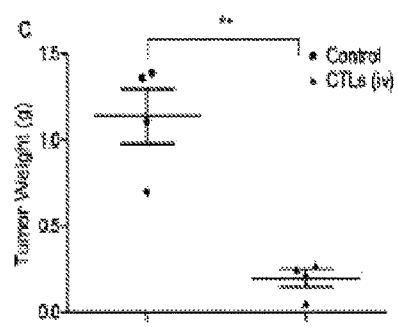
FIG. 9D
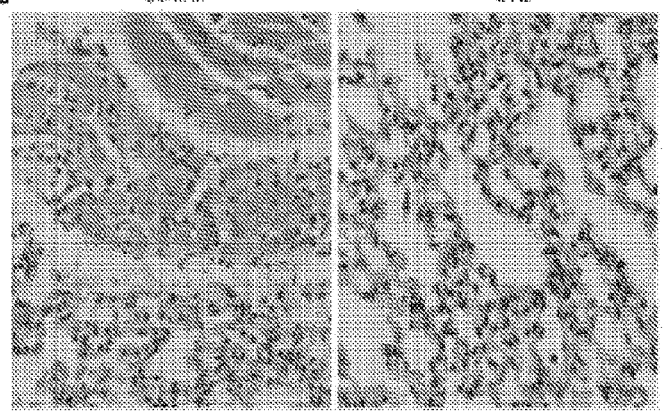
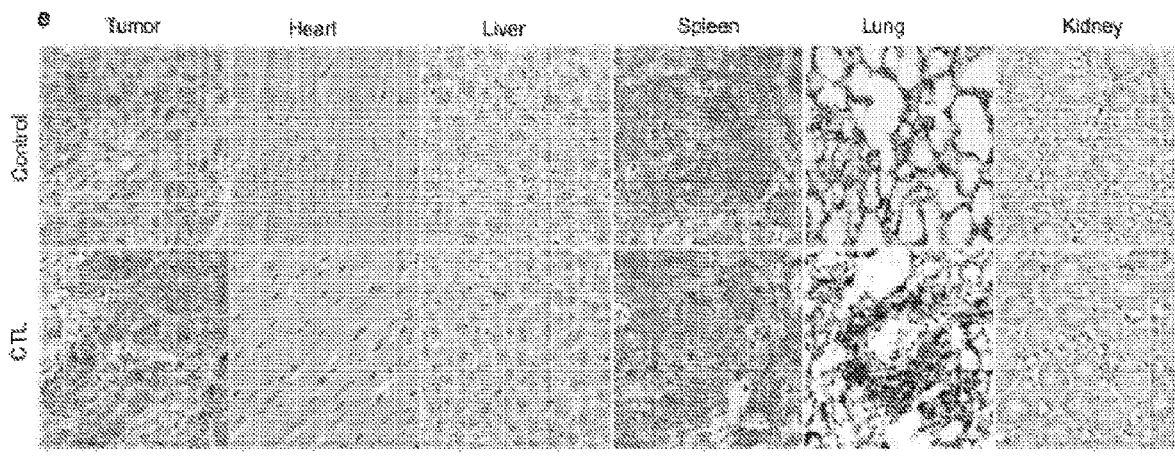
FIG. 9E

METHODS FOR GENERATING ENGINEERED HUMAN PRIMARY BLOOD DENDRITIC CELL LINES

CROSS-REFERENCE TO RELATED APPLICATIONS

This application claims the benefit of U.S. Provisional Appl. No. 62/243,177 filed on Oct. 19, 2015, the contents of which are hereby incorporated by reference in their entirety.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 60,990 Byte ASCII (Text) file named "sequence_listing_ST25.txt," created on Oct. 19, 2016.

FIELD OF THE INVENTION

The field of the invention relates generally to the field of biology and medicine. The field also relates to methods for the production of dendritic cells and related compositions useful in the treatment of disease such as cancer.

BACKGROUND OF THE INVENTION

Among professional antigen-presenting cells (APC), dendritic cells (DC) hold unique abilities to prime naïve T lymphocytes in mediating antigen-specific, adaptive immune response. Palucka, K. & Banchereau, J. Cancer immunotherapy via dendritic cells. *Nature Reviews Cancer* 12, 265-277 (2012). DCs also possess the capacity to induce activation and proliferation of γσ T cells and natural killer (NK) cells, bridging innate immunity to adaptive immune response. Tyler, C. J., Doherty, D. G., Moser, B. & Eberl, M. Human Vγ9/Vδ2 T cells: Innate adaptors of the immune system. *Cellular immunology* 296, 10-21 (2015); van Beek, J. J., Wimmers, F., Hato, S. V., de Vries, I. J. M. & Skold, A. E. Dendritic cell cross talk with innate and innate-like effector cells in antitumor immunity: implications for DC vaccination. *Critical Reviews™ in Immunology* 34:517-536 (2014). DCs are evolved from the bone marrow and migrate to lymphoid and non-lymphoid tissues via blood circulation. In blood, a vast majority of DCs are immature and are capable of engulfing foreign antigens from invading pathogens. Upon uptake of foreign antigens, immature DCs undergo a complex maturation and activation process through activation of a number of pathogen recognition receptors (PRRs), such as Toll-like receptors (TLRs), and cytokine receptors. Pradere, J.-P., Dapito, D. H. & Schwabe, R. F. The Yin and Yang of Toll-like receptors in cancer. *Oncogene* 33, 3485-3495 (2014); Dzopalic, T., Rajkovic, I., Dragicevic, A. & Colic, M. The response of human dendritic cells to co-ligation of pattern-recognition receptors. *Immunologic Research* 52, 20-33 (2012); Hammer, G. E. & Ma, A. Molecular control of steady-state dendritic cell maturation and immune homeostasis. *Annual Review of Immunology* 31, 743-791 (2013). Mature and activated DCs characteristically express cell surface co-stimulatory molecules such as CD80, CD83 and CD86, assemble the antigen peptide-MHC complex and migrate to secondary lymphoid tissues to promote antigen-specific T cell expansion.

DCs constitute 1% of immune cells in blood. Two major types of blood DCs including CD11c+ myeloid DCs (mDCs) and CD303+ plasmacytoid DCs (pDCs) have been characterized. Mildner, A. & Jung, S. Development and function of dendritic cell subsets. *Immunity* 40, 642-656 (2014). While pDCs are crucial in mediating anti-inflammatory response by secreting large amounts of interferon alpha (IFNα) upon encountering pathogens, mDCs play a major role in antigen presentation to prime naïve T cells. Osugi, Y., Vuckovic, S. & Hart, D. N. Myeloid blood CD11c+ dendritic cells and monocyte-derived dendritic cells differ in their ability to stimulate T lymphocytes. *Blood* 100, 2858-2866 (2002); Kassianos, A. J., Jongbloed, S. L., Hart, D. N. & Radford, K. J. Isolation of human blood DC subtypes. *Dendritic Cell Protocols*, 45-54 (2010). The CD11c+ subset of mDCs is relatively abundant, and a minor subset or CD141+ mDCs exhibit a potent ability to cross-present extracellular antigens on MHC-I to CD8 T cells, polarizing into cytotoxic T lymphocytes (CTL). Jongbloed, S. L. et al. Human CD141+ (BDCA-3)+dendritic cells (DCs) represent a unique myeloid DC subset that cross-presents necrotic cell antigens. *The Journal of Experimental Medicine* 207, 1247-1260 (2010); Bachem, A. et al. Superior antigen cross-presentation and XCR1 expression define human CD11c+ CD141+ cells as homologues of mouse CD8+ dendritic cells. *The Journal of Experimental Medicine* 207, 1273-1281 (2010). By analyzing the transcriptional profiling with comparative evaluation of human and murine DC subsets, it is proposed that human CD141+ DCs are closely related to the counterparts of murine CD8+ DCs, the major subset of DCs in mediating antigen cross-presentation. Since DCs are rarely infected by invading pathogens, therefore DC-mediated cross-presentation and induction of terminally differentiated cytotoxic effector T cells are essential steps in developing adaptive immunity against pathogenic viruses and cancer cells.

Because of the paucity of blood DCs, the current DC method frequently exploits antigen-loaded monocyte-derived DCs (MoDCs) through a complex maturation and activation process with a cocktail of cytokines and PRR stimulating factors. Kvistborg, P., Bøgh, M., Pedersen, A., Claesson, M. & Zocca, M. Fast generation of dendritic cells. *Cellular immunology* 260, 56-62 (2009); Jolanda, I., de Vries, M., Adema, G. J., Punt, C. J. & Figdor, C. G. Phenotypical and functional characterization of clinical-grade dendritic cells. *Adoptive Immunotherapy: Methods and Protocols*, 113-125 (2005). This method has been widely utilized in clinical cancer vaccine trials, however the clinical benefit of such approach is rather limited. There are apparently several drawbacks with this approach. Comparing to primary blood DCs, MoDCs are more closely related to in vitro-derived macrophages. Robbins, S. H. et al. Novel insights into the relationships between dendritic cell subsets in human and mouse revealed by genome-wide expression profiling. *Genome Biology* 9, R17 (2008). Additionally, in vitro-developed MoDCs have limited growth potential and can be hardly maintained in culture for prolonged time and therefore, repeated preparations of MoDCs is necessary for several rounds of vaccine delivery. To address these limitations, several human DC models have been developed in order to understand DC biology and to evaluate their potential application as cancer vaccine. van Helden, S. F., van Leeuwen, F. N. & Figdor, C. G. Human and murine model cell lines for dendritic cell biology evaluated. *Immunology Letters* 117, 191-197 (2008). For instance, MUTZ-3, a myeloid leukemia cell line, can mature and differentiate into DC-like cells in vitro. Masterson, A. J. et al. MUTZ-3, a human cell line model for the cytokine-induced differentiation of dendritic cells from CD34+ precursors. *Blood* 100, 701-703 (2002). MUTZ-3 cells can be stably maintained at the pre-DC stage in culture, providing an adequate amount of inducible DC-like cells for the development of cancer vaccine. Santegoets, S. J., van den Eertwegh, A. J., van de Loosdrecht, A. A., Scheper, R. J. & de Gruijl, T. D. Human dendritic cell line models for DC differentiation and clinical DC vaccination studies. *Journal of Leukocyte Biology* 84, 1364-1373 (2008); Santegoets, S. J. et al. In vitro priming of tumor-specific cytotoxic T lymphocytes using allogeneic dendritic cells derived from the human MUTZ-3 cell line. *Cancer Immunology, Immunotherapy* 55, 1480-1490 (2006).

Human T cell leukemia virus type-1 (HTLV-1) primarily infects CD4+ T cells to cause malignant transformation of T cells and development of adult T cell leukemia-lymphoma (ATL) among 3-5% of infected individuals. Ishitsuka, K. & Tamura, K. Human T-cell leukaemia virus type I and adult T-cell leukaemia-lymphoma. *The Lancet Oncology* 15, e517-e526 (2014). Other HTLV viruses are also known. For example, HTLV-2 is related to its pathogenic counterpart, HTLV-1, however, HTLV-2 has not been linked to the development of leukemia in humans. Ciminale, V., Rende, F., Bertazzoni, U. & Romanelli, M. G. HTLV-1 and HTLV-2: highly similar viruses with distinct oncogenic properties. *Front. Microbiol.* 5(398): 1-9 (2014). The viral Tax protein of HTLV-1 is considered to play a central role in the process leading to adult T cell leukemia. Azran et al., Role of Tax protein in human T-cell leukemia virus type-I leukemogenicity, *Retrovirology* 20041:20 (2004). HTLV-1 also infects dendritic cells, allowing cell-free virus to be transmissible to CD4+ T cells. Jones, K. S., Petrow-Sadowski, C., Huang, Y. K., Bertolette, D. C. & Ruscetti, F. W. Cell-free HTLV-1 infects dendritic cells leading to transmission and transformation of CD4+ T cells. *Nature* medicine 14, 429-436 (2008); Jain, P. et al. DC-SIGN mediates cell-free infection and transmission of human T-cell lymphotropic virus type 1 by dendritic cells. *Journal of Virology* 83, 10908-10921 (2009). In a very small percentage of HTLV-1-infected patients, a neuroinflammatory disorder called HTLV-1-associated myelopathy and tropical spastic paraparesis (HAM/TSP) occurs. Yamano, Y. & Sato, T. Clinical pathophysiology of human T-lymphotropic virus-type 1-associated myelopathy/tropical spastic paraparesis. *Frontiers in Microbiology* 3, 389 (2012). It is recognized that generation of Tax-reactive CD8+ CTLs plays a role in the pathogenesis of HAM/TSP, while the Tax-specific CTLs exert a protective immunity against ATL.

There is a need to develop new methods for generating dendritic cells, particularly from blood, for use as dendritic cell vaccines and for activating cytotoxic T lymphocytes that can be used therapeutically in subjects. The present invention satisfies this need and provides additional advantages as well.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

Provided herein is a method to develop primary dendritic cells with the viral protein Tax from the non-leukemia-causing retrovirus, human T cell leukemia virus type 2 (HTLV-2), a virus related to its pathogenic counterpart, HTLV-1.

It is shown herein that Tax can harness dendritic cells, leading to their maturation/activation and subsequent induction of a polarized cytotoxic T lymphocyte response. In the present disclosure, HTLV-2 Tax has been exploited as a molecular tool to establish primary blood dendritic cell lines and monocyte-derived dendritic cells. Human primary blood dendritic cells and monocyte-derived dendritic cells, along with methods of making and using the same are provided that enable the generation of highly potent anti-cancer cytotoxic lymphocytes.

In one aspect, the invention provides an engineered primary blood dendritic cell, wherein the dendritic cell expresses a functional Tax protein from a T cell leukemia virus. In some embodiments, the Tax protein is from a human T cell leukemia virus selected from the group consisting of HTLV-1, HTLV-2, HTLV-3 and HTLV-4.

In some embodiments, the engineered primary blood dendritic cell has a constitutive maturation and activation phenotype. The engineered primary blood dendritic cell is CD205+ and CD11c+. In some embodiments, the engineered primary blood dendritic cell expresses one or more dendritic cell maturation and activation markers selected from the group consisting of CD83, CD80, CD86, CD70, CCR7 and HLA-DR. In some embodiments, the engineered primary blood dendritic cell is TLR3+ and TLR4+. In some embodiments, the engineered primary blood dendritic cell expresses the cleaved form of TLR7. In some embodiments, the dendritic cell expresses TLR9. In some embodiments, the engineered primary blood dendritic cell produces IL-1A and TNFα. In some embodiments, the engineered primary blood dendritic cell produces IL-15. In some embodiments, the engineered primary blood dendritic cell produces negligible levels of IL-10 and TGFβ.

In some embodiments, the engineered primary blood dendritic cell expresses one or more of c-Myc, Mcl-1, Bcl-xL, Bcl-2, phosphorylated pRb, phosphorylated cdc, phosphorylated Stat1, phosphorylated Stat3, and phosphorylated Stat5. In some embodiments, the transcription factors NF-κB, Stat3 and AP-1 are active in the engineered primary blood dendritic cell. In some embodiments, the engineered primary blood dendritic cell is capable of inducing proliferation of naïve lymphocytes in the absence of exogenously added IL-2.

In some embodiments, the engineered primary blood dendritic cell has been genetically modified to express one or more HLA proteins. In some embodiments, the HLA protein is HLA-A2.1.

In some embodiments, the engineered primary blood dendritic cell harbors one or more exogenously added antigens or antigenic fragments or variants thereof. In some embodiments, the antigen is a cancer antigen. In some embodiments, the cell expresses human telomerase reverse transcriptase or an antigenic fragment or variant thereof. In some embodiments, the antigen comprises a fusion protein comprising a proteasomal target sequence of IκBα and a fragment of human telomerase reverse transcriptase. In some embodiments, the fusion protein comprises SEQ ID NO:13. In some embodiments, the engineered primary blood dendritic cell presents the cancer antigen in an HLA-restricted manner. In some embodiments, the cancer antigen is introduced by viral transduction. In some embodiments, the virus is a lentivirus. In some embodiments, the engineered primary blood dendritic cell is capable of priming naïve PBMCs to generate cytotoxic lymphocytes that recognize antigen. In some embodiments, the engineered primary blood dendritic cell is capable of priming naïve PBMCs to generate cytotoxic lymphocytes capable of killing cells in a non-HLA restricted manner.

In another aspect, the invention provides a method of generating an engineered primary blood dendritic cell, comprising:
  i) providing a sample of cells comprising immature dendritic cells; and
  ii) expressing a functional Tax protein from a T cell leukemia virus in the cells.

In some embodiments, the method further comprises iii) culturing the cells to induce their maturation and activation. The culturing step to induce the maturation and activation of the engineered primary blood dendritic cell is not limiting. In some embodiments, the cells are cultured in the presence of one or more cytokines. In some embodiments, the cells are cultured in media comprising an effective amount of IL-2. In some embodiments, the method further comprises depleting T cells from the cultured cells.

In another aspect, the invention provides a method of generating an engineered primary blood dendritic cell, comprising:
  i) providing a sample of cells comprising immature dendritic cells;
  ii) expressing a functional Tax protein from a T cell leukemia virus in the cells and culturing the cells;
  iii) culturing the cells to induce their differentiation into mature dendritic cells; and
  iv) depleting T cells from the cultured cells.

In another aspect, the invention provides a method of generating an engineered primary blood dendritic cell, comprising:
  i) providing a sample of cells comprising immature dendritic cells, such as a sample of PBMCs;
  ii) treating the cells in culture with an effective amount of phytohaemagglutinin (PHA);
  iii) treating the cells in culture with an effective amount of IL-2;
  iv) expressing a functional Tax protein from a T cell leukemia virus in the cells and culturing the cells; and
  v) depleting T cells from the cultured cells.

In some embodiments, the PBMCs are isolated from a leukopak. In some embodiments, the concentration of PHA ranges from about 1-5 µg/ml. In some embodiments, the cells are treated for PHA from about 12 hours to about 36 hours. In some embodiments, the cells are treated with about 100-200 units/ml of IL-2 and cultured for a period of time in media comprising IL-2. In some embodiments, the cells are cultured for a period of time from about 4-5 days in media comprising IL-2. In some embodiments, the cells are manipulated to express a functional Tax protein following step iii).

In some embodiments, the cells are transduced with a virus that encodes a functional Tax protein. In some embodiments, the virus is a lentivirus. In some embodiments, the cells are transduced in the presence of about 10 µg/ml polybrene.

In some embodiments, the transduced cells are further cultured in media comprising about 100-200 units/ml of IL-2. In some embodiments, the transduced cells are further cultured in media comprising IL-2 for about 2-3 months. In some embodiments, the transduced cells are cultured in media comprising human serum and about 100-200 units/ml of IL-2. In some embodiments, the transduced cells are cultured for about 2-3 months in media comprising human serum and about 100-200 units/ml of IL-2. In some embodiments, the cells are cultured in complete RPMI1640 medium comprising 5% heat-inactivated human AB serum and about 100-200 units/ml of IL-2. In some embodiments, the cells are cultured in media comprising complete RPMI1640 medium comprising 10% fetal bovine serum and about 100-200 units/ml of IL-2.

In some embodiments, the T cells are depleted with a composition comprising a molecule that binds to T cells. In some embodiments, the T cells are depleted with an antibody. In some embodiments, the antibody is an anti-CD3 antibody. In some embodiments, the antibody is conjugated to a magnetic bead.

In another aspect, the invention provides an engineered monocyte-derived dendritic cell, wherein the dendritic cell expresses a functional Tax protein from a T cell leukemia virus. In some embodiments, the Tax protein is from a human T cell leukemia virus selected from the group consisting of HTLV-1, HTLV-2, HTLV-3 and HTLV-4. The engineered monocyte-derived dendritic cell is CD205+.

In some embodiments, the engineered monocyte-derived dendritic cell has a constitutive maturation and activation phenotype. In some embodiments, the engineered monocyte-derived dendritic cell expresses one or more dendritic cell maturation and activation markers selected from the group consisting of CD83, CD80, CD86, and CD70. In some embodiments, the engineered monocyte-derived dendritic cell further expresses 4-1BBL and/or CD4. In some embodiments, the engineered monocyte-derived dendritic cell is capable of proliferating for up to three months in culture. In some embodiments, the cell is TLR3+ and TLR4−. In some embodiments, the engineered monocyte-derived dendritic cell expresses the cleaved form of TLR7. In some embodiments, the cell produces IL-1A and TNFα. In some embodiments, the engineered monocyte-derived dendritic cell produces TGFβ. In some embodiments, the engineered monocyte-derived dendritic cell produces IL-15. In some embodiments, the engineered monocyte-derived dendritic cell expresses one or more of the following: c-Myc, Mcl-1, Bcl-xL, Bcl-2, phosphorylated pRb, phosphorylated cdc2, phosphorylated Stat1, phosphorylated Stat3, and phosphorylated Stat5.

In some embodiments, the engineered monocyte-derived dendritic cell is capable of inducing proliferation of naïve lymphocytes in the absence of exogenously added IL-2. In some embodiments, the engineered monocyte-derived dendritic cell has been genetically modified to express one or more HLA proteins. In some embodiments, the engineered monocyte-derived dendritic cell has been genetically modified to express HLA-A2.1.

In some embodiments, the engineered monocyte-derived dendritic cell expresses one or more antigens or antigenic fragments or variants thereof. In some embodiments, the antigen is a cancer antigen. In some embodiments, the engineered monocyte-derived dendritic cell expresses human telomerase reverse transcriptase or an antigenic fragment or variant thereof. In some embodiments, the antigen comprises a fusion protein comprising a proteasomal target sequence of IκBα and a fragment of human telomerase reverse transcriptase. In some embodiments, the fusion protein comprises SEQ ID NO:13. In some embodiments, the cell presents the cancer antigen in an HLA-restricted manner.

In some embodiments, the engineered monocyte-derived dendritic cell is capable of priming naïve lymphocytes, such as a population of PBMCs to generate cytotoxic lymphocytes that recognize antigen. In some embodiments, the engineered monocyte-derived dendritic cell is capable of priming naïve lymphocytes such as a population of PBMCs to generate cytotoxic lymphocytes capable of killing cells in a non-HLA restricted manner.

In another aspect, the invention provides a method of generating monocyte-derived dendritic cells, comprising:
i) providing a sample of cells comprising immature dendritic cells derived from monocytes; and
ii) expressing a functional Tax protein from a T cell leukemia virus in the cells.

In some embodiments, the method further comprises, prior to part i) culturing monocyte cells to induce their differentiation into immature dendritic cells. In some embodiments, differentiation is induced by contacting the monocytes with a culture medium comprising an effective amount of a composition that induces the differentiation of monocytes into immature dendritic cells, including, but not limited to, GM-CSF; GM-CSF and IL-4: GM-CSF and IL-13; GM-CSF and IL-15; and IFNα. In some embodiments, the monocytes are cultured in media comprising effective amounts of GM-CSF and IL-4 to induce differentiation to immature dendritic cells.

In some embodiments, the method further comprises a step after part ii) comprising culturing the cells to induce their maturation and activation. The culturing step to induce the maturation and activation of the monocyte-derived dendritic cell is not limiting. In some embodiments, the cells are culture in the presence of one or more cytokines. In some embodiments, the cells are further cultured in media comprising an effective amount of GM-CSF and IL-4.

In another aspect, the invention provides a method of generating monocyte-derived dendritic cells, comprising:
i) providing adherent monocyte cells;
ii) culturing the cells in media comprising an effective amount of GM-CSF and IL-4;
iii) expressing a functional Tax protein from a T cell leukemia virus in the cells; and
iv) culturing the functional Tax protein expressing cells in media comprising an effective amount of GM-CSF and IL-4.

In some embodiments, following step iv), the method further comprises culturing the cells in media comprising an effective amount of IL-2. In some embodiments, IL-4 and/or GM-CSF is fused to Fc4. In some embodiments, the adherent monocytes come from PBMCs, for example, about 4 million PBMCs. In some embodiments, the culturing of part ii) comprises culturing the cells in media comprising conditioned medium from GM-CSF-Fc4/IL-4-Fc4 producing 293 cells. In some embodiments, the cells are cultured in media comprising the conditioned medium at about a 1:10 dilution for about 7 days. In some embodiments, the cells are transduced with a virus that encodes a functional Tax protein from a T cell leukemia virus. In some embodiments, the cell is transduced in the presence of about 10 μg/ml polybrene.

In some embodiments, the cells are cultured in media comprising RPMI1640 with about 10% fetal bovine serum. In some embodiments, the culturing step iv) comprises culturing the Tax protein expressing cells in RPMI1640 medium with 10% FBS in the presence of GM-CSF-Fc4 and IL-4-Fc4 for about 5-7 days, followed by maintaining the cells in culture in the presence of about 100-200 u/ml of IL-2.

In some embodiments, the method further comprises activating the monocyte-derived dendritic cells. In some embodiments, the activating comprises stimulating the cells with effective amounts of TNFα and LPS. In some embodiments, the cells are stimulated for about 2 days.

In another aspect, the invention provides a method for producing cytotoxic T lymphocytes, comprising culturing the primary blood or monocyte-derived dendritic cells together with cells comprising naïve lymphocytes for a period of time, whereby cytotoxic T lymphocytes are produced.

In another aspect, the invention provides a method for producing cytotoxic T lymphocytes, comprising
i) culturing dendritic cells of the invention together with cells comprising naïve lymphocytes for a first period of time to create a mixed culture of cells; and
ii) treating the mixed culture of cells with IL-2 and continuing to culture the cells for a second period of time,
whereby cytotoxic T lymphocytes are produced.

In some embodiments, the cells comprising naïve lymphocytes comprise naïve PBMCs. In some embodiments, the naïve lymphocytes are isolated from leukopaks. In some embodiments, the naïve lymphocytes and the dendritic cells are allogeneic. In some embodiments, the ratio of dendritic cells to naïve PBMCs is about 1:100. In some embodiments, the culturing of step i) is conducted without addition of exogenous cytokines. In some embodiments, the first period of time is about 2-3 days. In some embodiments, the concentration of the IL-2 is about 100-200 u/ml. In some embodiments, the second period of time is from 2-6 weeks. In some embodiments, the cytotoxic T lymphocytes are antigen specific and induce cytolysis of target cells in an HLA-restricted manner.

In some embodiments, the cytotoxic T lymphocytes comprise CD3+/CD56+ T cells capable of killing target cells in a non-HLA-restricted manner. In some embodiments, the dendritic, cells express 4-1BBL. In some embodiments, the dendritic cells have been engineered to express 4-1BBL. In some embodiments, the non-HLA-restricted killing of cells is mediated by ligand binding of NKG2D.

In another aspect, the invention provides a pharmaceutical composition, comprising an effective amount of cytotoxic T lymphocytes, produced according to a methods of the invention.

In another aspect, the invention provides a method of treating a disease or condition in a subject, comprising administering to the subject an effective amount of cytotoxic T lymphocytes, wherein the cytotoxic T lymphocytes are produced using a primary blood dendritic cell and/or a monocyte-derived dendritic cell of the invention.

In another aspect, the invention provides a method of treating a disease or condition in a subject, comprising administering to the subject an effective amount of cytotoxic T lymphocytes, wherein the cytotoxic T lymphocytes are produced by a method of the invention.

In another aspect, the invention provides a method of treating a disease or condition in a subject, comprising administering to the subject an effective amount of a primary blood dendritic cell and/or a monocyte-derived dendritic cell of the invention.

In another aspect, the invention provides a method of treating a disease or condition in a subject, comprising administering to the subject an effective amount of a primary blood dendritic cell and/or monocyte-derived dendritic cell produced by a method of the invention.

In some embodiments, the disease to be treated is cancer. In some embodiments, the cancer cells express MICA/B. In some embodiments, the cancer is breast cancer. In some embodiments, the subject to be treated is a human.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

Figure 1A:
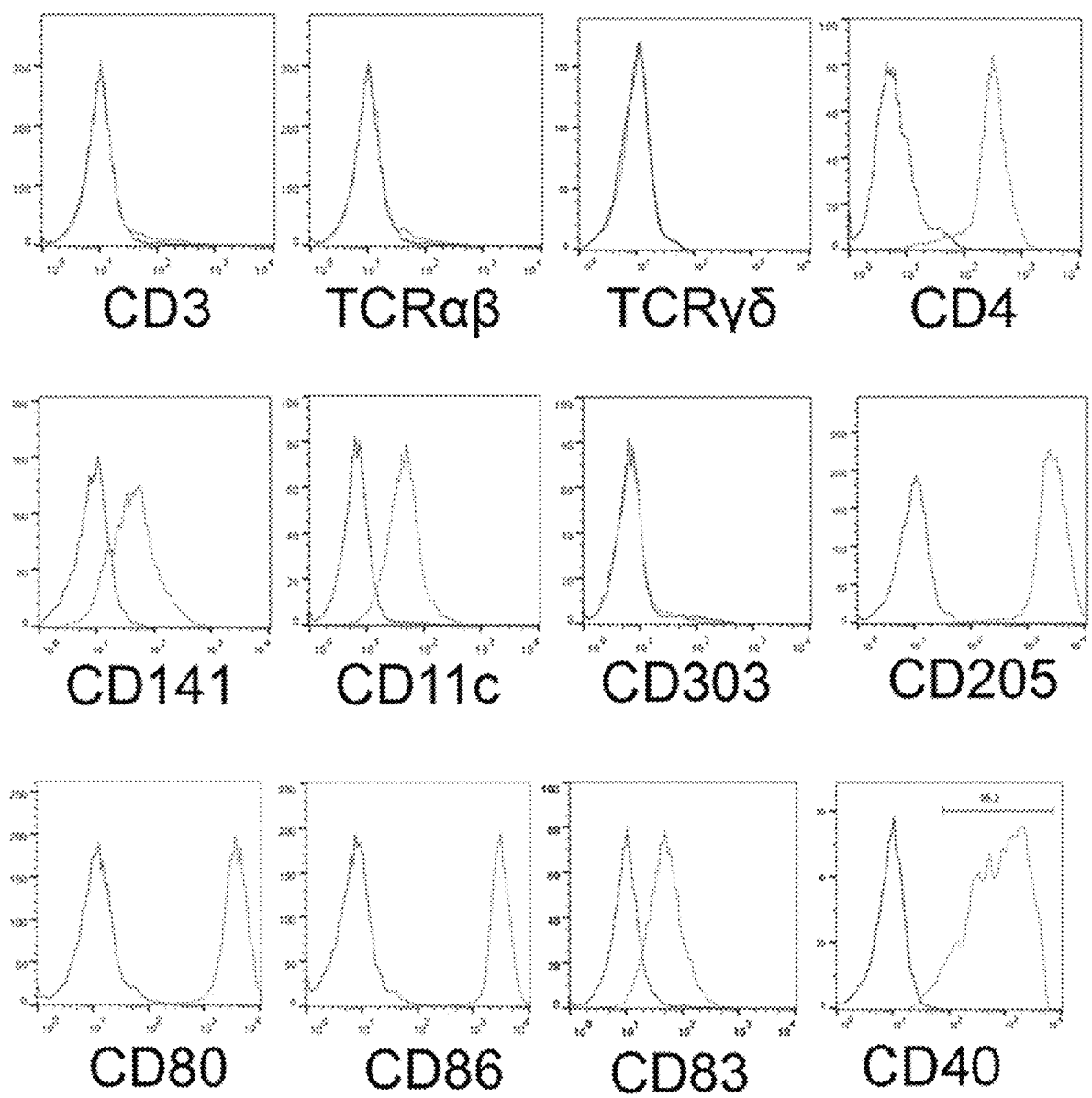
FIG. 1. Immunophenotyping analysis of the established ihv-DC cell lines. (a) ihv-DC1. (b) ihv-DC2. (c) Image of GM-CSF/IL-4 stimulated and differentiated DCs from adherent monocytes of healthy blood donors. (d) Immunophenotype of MoDC-Tax cells generated from the MoDCs that were transduced with the Tax-GFP lentivirus.
Figure 1A:
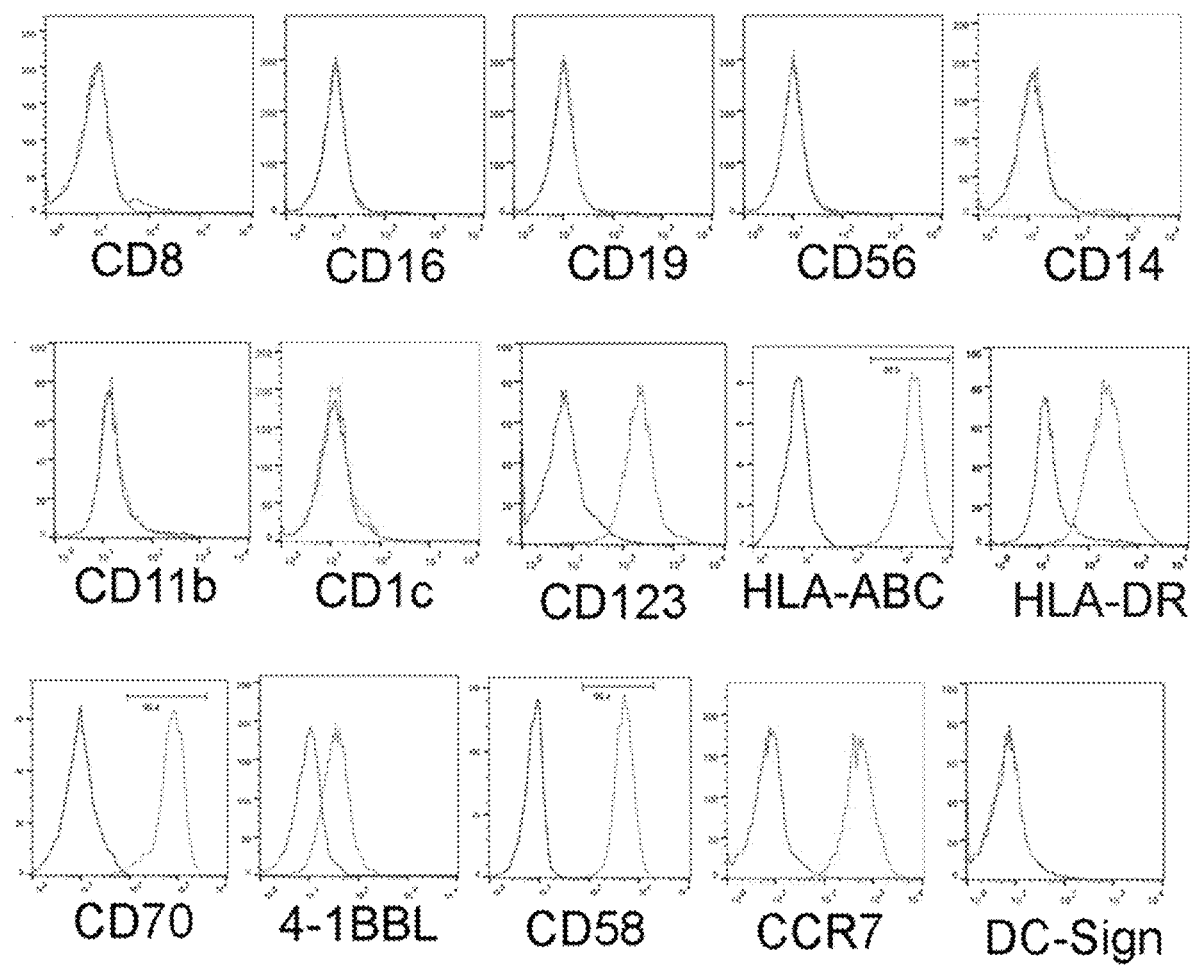

Tumor volumes of the mice of the control and CTL treatment groups. (b) Image of the tumors harvested at the end point. (c) Tumor weight at the end point. (d) HE staining of the lung tissues in the control group and the CTL treatment group. (e) Anti-human CD3 staining of tumor and various tissues using the IHC method.

FIG. 10. ihv-DC1-activated CTLs inhibit growth of MCF-7/ADR tumors in NSG mice. (a) Tumor volume. (b) Tumor weight at the end point. (c) Mouse weight. (d) HE staining of the lung tissues of mice in the control group and the CTL treatment group, (e) Anti-human CD3 staining of the tumor and various tissues using the IHC method.

DETAILED DESCRIPTION OF THE INVENTION

The inventor has surprisingly discovered methods of preparing engineered dendritic cells. The engineered dendritic cells can be either primary blood dendritic cells or dendritic cells derived from monocytes. The engineered dendritic cells express a functional Tax protein from a T cell leukemia virus. The invention provides engineered dendritic cells, methods of making and using the cells, and pharmaceutical and vaccine compositions comprising the cells.

In some embodiments, antigen-loaded dendritic cells of the invention are useful as vaccines in the treatment or prevention of disease or for the activation of T cells, which can then be used in therapy. For example, antigen loaded dendritic cells can be used to elicit an immune response against an antigen. They may be used as vaccines to prevent future infection or disease, or to activate the immune system to treat ongoing disease, including, but not limited to pathogen infection or cancer. The antigen loaded dendritic cells can be formulated for use as vaccines or pharmaceutical compositions with suitable carriers such as physiological buffers or other injectable liquids. The vaccines or pharmaceutical compositions can be administered in therapeutically effective amounts sufficient to elicit an immune response.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. *Molecular Cloning: A Laboratory Manual, 2$^{nd}$ edition* (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2: A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

An "effective amount" is an amount sufficient to effect beneficial or desired results. An effective amount can be administered in one or more administrations, applications or dosages. For example, the term "effective amount" with regard to the activated lymphocytes, is meant an amount that produces the desired effect for which it is administered, e.g., inhibiting the growth of cancer cells or killing the cancer cells. In the context of dendritic cells, an "effective amount" is meant an amount that is capable of inducing an immune response, e.g., inducing the activation of T lymphocytes. The activated T lymphocytes can function in an HLA or non-HLA restricted manner. The exact amount will depend on the particular agent, the subject to be treated, and will be ascertainable by a person skilled in the art using known methods and techniques for determining effective doses.

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need of treatment include those already with cancer as well as those prone to have cancer or in those in whom cancer metastasis is to be prevented.

By "cancer" is meant the abnormal presence of cells which exhibit relatively autonomous growth, so that a cancer cell exhibits an aberrant growth phenotype characterized by a significant loss of cell proliferation control. Cancerous cells can be benign or malignant. Various types of cancer are known and the cancer to be treated is not limiting. A cancer cell, as used herein, includes not only a primary cancer cell, but also any cell derived from a cancer cell. This includes metastasized cancer cells, and in vitro cultures and cell lines derived from cancer cells. Cancer includes, but is not limited to, solid tumors and hematologic malignancies.

The term "antigen" is well understood in the art and includes substances which are immunogenic, i.e., immunogens, as well as antigenic epitopes. In some embodiments, the engineered primary blood dendritic cells and monocyte-derived dendritic cells of the invention can be loaded with one or more antigens for presentation to other cells, e.g., T lymphocytes. Antigen loaded dendritic cells are useful as vaccines and for the in vitro stimulation of T cells.

It will be appreciated that the use of any antigen is envisioned for use in the present invention and thus includes, but is not limited to, a self-antigen (whether normal or disease-related), an infectious antigen (e.g., a microbial antigen, viral antigen, etc.), or some other foreign antigen (e.g., a food component, pollen, etc.). The term "antigen" or alternatively, "immunogen" also applies to collections of more than one immunogen, so that immune responses to multiple immunogens may be modulated simultaneously. Moreover, the term includes any of a variety of different formulations of immunogen or antigen.

In some embodiments, the antigen is from a cancer cell or a pathogen. In some embodiments, the cancer cell is a breast cancer cell.

Antigens can be loaded into immature or mature dendritic cells. If antigens are loaded into immature dendritic cells, the immature dendritic cells can then be matured by the process of loading itself, or by other maturation methods described herein or alternative maturation methods known to those of skill in the art. The loading of the antigen on the dendritic cells is not limiting. In some embodiments, the antigen can be loaded using methods as described herein, including transfection, transduction, electroporation and peptide pulsing. In some embodiments, the cancer antigen is introduced by viral transduction. In some embodiments, the virus is a lentivirus. In some embodiments, the antigen is delivered to the dendritic cells as described herein, in the form of nucleic acid that is isolated or derived from a cancer cell or a pathogen. In some embodiments, the antigen is encoded by a virus that is capable of infecting the dendritic cells. "Derived from" includes, but is not limited recombinant variants of naturally occurring sequences, including fusions to unrelated or related sequences.

In some embodiments, the antigen(s) can be loaded as the antigen itself (e.g., proteins, peptides, epitopes, cell lysates, viral particles, etc.) or can be loaded as a nucleic acid(s) encoding antigen(s). Methods for loading dendritic cells with peptide and protein antigens, cells, cell or tissue lysates, viruses or viral particles, nucleic acids and the like are known to those of skill in the art.

The antigen can be from any source. However, in some embodiments, the antigen or antigen(s) are autologous to the subject. By autologous to the subject is meant that the antigen is obtained or derived from the subject. As non-limiting examples, the antigens may be from cancer cells or tumor tissue obtained from a subject. The cancer antigens can be loaded into dendritic cells as cancer cells, cancer cell or tissue lysates, extracts from cancer cells or tissues, purified or cloned components of cancer cells or tissues, total RNA or total mRNA, or selected RNA or mRNA from such cells or tissues, whether present in extracts, purified, amplified, in vitro translated and the like. In one embodiment, the cancer antigen is engineered into a viral vector, such as a lentiviral vector for administration to the immature or mature dendritic cell. In some embodiments, the antigen can be obtained or derived from a pathogen or pathogen-infected cells present in a subject.

In some embodiments, the antigen is a cancer antigen and comprises human telomerase reverse transcriptase or an antigenic fragment or variant thereof. In some embodiments, the cancer antigen comprises a fusion protein comprising a proteasomal target sequence of IκBα and sequence from a cancer cell. In some embodiments, IκBα has the nucleotide and amino acid sequence shown in SEQ ID NO:11 and a nucleotide sequence shown in SEQ ID NO:12, respectively. In some embodiments, the sequence from a cancer cell comprises a fragment of human telomerase reverse transcriptase (hTERT). In some embodiments, hTERT has the amino acid sequence shown in SEQ ID NO:9 and a nucleotide sequence shown in SEQ ID NO:10. In some embodiments, the cancer antigen comprises full length IκBα and a hTERT fragment (aa 301-700) fusion protein. In some embodiments, the fusion protein comprises SEQ ID NO:13.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin-3 (IL-3), interleukin-4 (IL-4), interleukin-6 (IL-6), interleukin-11 (IL-11), interleukin-12 (IL-12), interleukin-13 (IL-13), interleukin-15 (IL-15), granulocyte-colony stimulating factor (G-CSF), granulocyte macrophage-colony stimulating factor (GM-CSF), interleukin-1 beta (IL-1β), interferon-γ (IFNγ), tumor necrosis factor-α (TNFα), prostaglandin E2 (PGE2), MIP-11, leukemia inhibitory factor (LIF), c-kit ligand, thrombopoietin (TPO) and flt3 ligand. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The term "dendritic cells (DCs)" refers to a population of morphologically similar cell types found in a variety of lymphoid and non-lymphoid tissues. Steinman, *Ann. Rev. Immunol.* 9:271-296 (1991). Dendritic cells constitute the most potent and preferred APCs in the organism. Dendritic cells can be differentiated from monocytes and possess a distinct phenotype from monocytes. For example, a particular differentiating marker, CD14 antigen, is not found in dendritic cells but is possessed by monocytes. It has been shown that mature DCs can provide all the signals necessary for T cell activation and proliferation. Also, mature dendritic cells are not phagocytic, whereas the monocytes and immature dendritic cells are strongly phagocytosing cells. Immature DCs are capable of capturing antigens by endocytosis, phagocytosis, macropinocytosis or adsorptive pinocytosis and receptor mediated antigen uptake, and are phenotypically CD80⁻ or CD80$^{low}$, CD83⁻ or CD83$^{low}$, CD86$^{low}$, and have high intracellular concentrations of MHC class II molecules. Mature DCs have a veiled morphology, a lower capacity for endocytosis and are phenotypically CD80$^{high}$, CD83$^{high}$, CD86$^{high}$ in comparison to immature DCs.

As used herein, "expression" refers to the processes by which polynucleotides are transcribed into mRNA and/or mRNA is translated into peptides, polypeptides, or proteins.

The term "genetically modified" means containing and/or expressing a foreign gene or nucleic acid sequence which in turn, modifies the genotype or phenotype of the cell or its progeny.

The term "isolated" means separated from constituents, cellular and otherwise, in which the polynucleotide, peptide, polypeptide, protein, antibody, or fragments thereof, or cells are normally associated with in nature. For example, with respect to mammalian cells, in some embodiments an isolated mammalian cell is separated from where it is normally found in the body, or is removed from the body. For example, leukocytes collected by leukopheresis are "isolated," and dendritic cells differentiated from monocytes or other cells in vitro are "isolated." The dendritic cell can also be further isolated and purified from a heterogeneous population of cells, e.g., lymphocytes with which they are associated.

The terms "major histocompatibility complex" or "MHC" refers to a complex of genes encoding cell-surface molecules that are required for antigen presentation to T cells and for rapid graft rejection. In humans, the MHC is also known as the "human leukocyte antigen" or "HLA" complex. The proteins encoded by the MHC are known as "MHC molecules" and are classified into Class I and Class II MHC molecules. Class I MHC molecules include membrane heterodimeric proteins made up of an α chain encoded in the MHC noncovalently linked with the β2-microglobulin. Class I MHC molecules are expressed by nearly all nucleated cells and have been shown to function in antigen presentation to CD8 T cells. Class I molecules include HLA-A, B, and C in humans. Class II MHC molecules also include membrane heterodimeric proteins consisting of noncovalently associated α and β chains. Class II MHC molecules are known to function in CD4$^+$ T cells and, in humans, include HLA-DP, DQ, and DR.

"Pathogen", as used herein, refers to any disease causing organism, such as, for example, bacteria, fungi, parasite or virus, and also to attenuated derivatives thereof.

A "pharmaceutical composition" is intended to include the combination of an active agent (such as an antigen-loaded dendritic cell and/or activated lymphocyte) with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as heat-inactivated serum plus 10% DMSO plus 5% dextrose, phosphate buffered saline solution, water, and emulsions, such as an oil/water or water/oil emulsion, and various types of wetting agents. The compositions also can include adjuvants, stabilizers and preservatives. For examples of carriers, stabilizers and adjuvants, see *Remington's Pharm. Sci.* 18.sup.th Ed. (Mack Publ. Co., Easton (1990)).

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

As used herein "subject" refers to any bird, fish, reptile, amphibian, or mammal. In some embodiments, the subject is a primate, rodent, dog or cat. In some embodiments, the subject is a human.

As used herein, "monocyte" refers to a CD14+ leukocyte having the capacity to differentiate into a dendritic cell. A monocyte is capable of differentiating into immature dendritic cells in response to GM-CSF and IL-4. The monocyte may be from any animal, and in some embodiments is a human monocyte. The monocytes can be provided and incubated in compositions such as, but not limited to, blood, blood fractions (e.g., white blood cells (WBCs), buffy coats, peripheral blood mononuclear cells (PBMCs), etc. and as well as in compositions further enriched for monocytes. In one embodiment, the monocytes are provided together with other peripheral blood mononuclear cells (PBMCs), for example, as a leukapheresis product. In another embodiment, the monocytes are enriched from PBMCs, or isolated directly from peripheral blood. Methods of isolating monocytes or PBMCs containing monocytes are known to those of skill in the art. In some embodiments, the monocytes are collected together with other PBMCs by leukapheresis. Methods of leukapheresis are known in the art. In some embodiments of the invention, PBMCs comprising monocytes are collected from a subject by leukapheresis at a hospital, clinic, doctor's office, etc. Leukapheresis is a procedure by which the white blood cells are removed from a subject's blood, the remainder of which is then transfused back into the subject. The leukapheresis product is typically a blood fraction enriched for PBMCs, with low levels of contaminating red blood cells, granulocytes and platelets. Methods and equipment for performing leukapheresis are well known in the art. See, for example gambrobct.com/Products_&_Services/for detailed information on leukapheresis. Examples of leukapheresis apparatuses include the COBESpectra™ manufactured by GAMBRO BCT, and the CS3000 Plus Blood Cell Separator manufactured by Baxter Fenwal.

A "functional Tax protein" is a protein that is capable of performing one or more functions of a wild-type Tax protein from a T cell leukemia virus (HTLV). A functional Tax protein is defined by its activity to induce NF-κB activation in the cell. The engineered primary blood dendritic cell and monocyte-derived dendritic cell of the invention comprises a functional Tax protein. In some embodiments, the Tax protein is from a human T cell leukemia virus selected from the group consisting of HTLV-1, HTLV-2, HTLV-3 and HTLV-4. In some embodiments, the functional Tax protein is a full length protein from a human T cell leukemia virus selected from the group consisting of HTLV-1, HTLV-2, HTLV-3 and HTLV-4. In some embodiments, the Tax protein is from HTLV-1. In some embodiments, the Tax protein is from HTLV-1 and comprises the amino acid sequence of SEQ ID NO:1 and the nucleotide sequence of SEQ ID NO:2. In some embodiments, the Tax protein is from HTLV-2. In some embodiments, the Tax protein is from HTLV-2 and comprises the amino acid sequence of SEQ ID NO:3 and the nucleotide sequence of SEQ ID NO:4. In some embodiments, the Tax protein is from HTLV-3. In some embodiments, the Tax protein is from HTLV-3 and comprises the amino acid sequence of SEQ ID NO:5 and the nucleotide sequence of SEQ ID NO:6. In some embodiments, the Tax protein is from HTLV-4. In some embodiments, the Tax protein is from HTLV-4 and comprises the amino acid sequence of SEQ ID NO:7 and the nucleotide sequence of SEQ ID NO:8. In some embodiments, the Tax protein is from HTLV-2, which is a virus that does not cause leukemia in humans.

In some embodiments, the nucleic acid sequence of the functional Tax protein contains a nucleotide sequence that is highly identical, at least 90% identical, with a nucleotide sequence encoding a Tax polypeptide. In some embodiments, the nucleic acid sequence of the functional Tax protein comprises a nucleotide sequence that is at least 60%, 65%, 70%, 75%, 80%, 85%, 90%, 91%, 92%, 93%, 94%, 95%, 96%, 97%, 98% 99% or 100% identical with the nucleotide sequence set forth in any of SEQ ID NOS:2, 4, 6 or 8.

In some embodiments, the polynucleotide encoding a functional Tax protein may include the coding sequence for the full-length polypeptide or a fragment thereof, by itself; or the coding sequence for the full-length polypeptide or fragment in reading frame with other coding sequence. The polynucleotide may also contain non-coding 5' and 3' sequences, such as transcribed, non-translated sequences, splicing and polyadenylation signals, ribosome binding sites and sequences that stabilize mRNA.

In some embodiments, the nucleotide sequence encoding a functional Tax protein includes nucleic acid molecules comprising a polynucleotide having a nucleotide sequence at least 90%, 91%, 92%, 93%, 94%, 95%, 96%, 97%, 98% 99% or 100% identical to (a) a nucleotide sequence encoding Tax protein having the amino acid sequence in any of SEQ ID NOS:1, 3, 5 or 7; or (b) a nucleotide sequence complementary to the nucleotide sequences in (a).

In some embodiments, the functional Tax protein for use in the invention comprises SEQ ID NO:3. In some embodiments, the Tax protein comprises biologically active fragments or variants of SEQ ID NO:3. In some embodiments, the Tax protein comprising biologically active fragment or variants have at least 80% identity to SEQ ID NO:3. In some embodiments, the biologically active fragments or variants have at least 81%, 82%, 83%, 84%, 85%, 86%, 87%, 88%, 89%, 90%, 91%, 92%, 93%, 94%, 95%, 96%, 97%, 98% or 99% identity to the polypeptide of SEQ ID NO:3.

In some embodiments, the functional Tax protein comprises a fusion protein comprising a full length Tax protein or a biologically active fragment thereof. A fragment is a polypeptide having an amino acid sequence that entirely is the same as part but not all of the amino acid sequence of the aforementioned Tax polypeptide. In some embodiments, a fragment may constitute at least about 150 contiguous amino acids identified in any of SEQ ID NOS:1, 3, 5 or 7. In some embodiments, the fragment is at least about 100, 120, 130, 140, 150, 160, 170, 180, 190, 200, 210, 220, 230, 240, 250, 260, 270, 280, 290, 300, 310, 320, or 330 contiguous amino acids identified in any of SEQ ID NOS:1, 3, 5 or 7.

In some embodiments the fragments include, for example, truncation polypeptides having the amino acid sequence of Tax, except for deletion of a continuous series of residues that includes the amino terminus, or a continuous series of residues that includes the carboxyl terminus or deletion of two continuous series of residues, one including the amino terminus and one including the carboxyl terminus.

In one embodiment, the fragment comprises the final about 290, 300, 310, 320, or 330 amino acids of any of SEQ ID NOS:1, 3, 5 or 7.

In one embodiment, the fragment comprises the first 200, 210, 220, 230, 240, 250, 260, 270, 280, 290, 300, 310, 320 or 330 amino acids of any of SEQ ID NOS:1, 3, 5 or 7.

Biologically active or functional fragments or variants of Tax protein include polypeptides having an amino acid sequence at least 80% identical to any of SEQ ID NOS:1, 3, 5 or 7 or fragments thereof with at least 80% identity to the corresponding fragment of any of SEQ ID NOS:1, 3, 5 or 7. Included in this group are variants of the defined sequence and fragment. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 1, 2, 3, 4, 5, 6, 7, 8, 9, 10 or more amino acids are substituted, deleted, or added in any combination.

Conventional means utilizing known computer programs such as the BestFit program (Wisconsin Sequence Analysis Package, Version 10 for Unix, Genetics Computer Group, University Research Park, 575 Science Drive, Madison, Wis. 53711) may be utilized to determine percent identity of a particular sequence.

As described in the methods herein, immature dendritic cells are manipulated to express a functional Tax protein from a T cell leukemia virus. The functional Tax protein present in the dendritic cells as described herein in accordance with the invention is not expressed as a result of an infection of a T cell leukemia virus (i.e., a non-engineered virus or wild-type virus) of the immature dendritic cells. Instead, a nucleic acid encoding a functional Tax protein is delivered to the cell by other mechanisms, such as engineering a nucleic acid construct comprising a functional Tax protein and delivery of the construct to the immature dendritic cell. In some embodiments, nucleic acid encoding a functional Tax protein can be engineered in a viral vector and used to transduce the cells. In some embodiments, the cells are transduced in the presence of about 10 µg/ml polybrene.

The viral vector which can be used to transduce the cells is not limiting. In some embodiments, the viral vector will typically comprise a highly attenuated, non-replicative virus. Viral vectors include, but are not limited to, DNA viral vectors such as those based on adenoviruses, herpes simplex virus, avian viruses, such as Newcastle disease virus, poxviruses such as vaccinia virus, and parvoviruses, including adeno-associated virus; and RNA viral vectors, including, but not limited to, the retroviral vectors. Vaccinia vectors and methods useful in immunization protocols are described in U.S. Pat. No. 4,722,848. Retroviral vectors include lentiviruses such as human immunodeficiency virus. Naldini et al. (1996) *Science* 272:263-267. Replication-defective retroviral vectors harboring a nucleotide sequence of interest as part of the retroviral genome can be used. Such vectors have been described in detail. (Miller, et al. (1990) *Mol. Cell. Biol.* 10:4239; Kolberg, R. (1992) *J. NIH Res.* 4:43; Cornetta, et al. (1991) *Hum. Gene Therapy* 2:215).

Adenovirus and adeno-associated virus vectors useful in the invention may be produced according to methods already taught in the art. (See, e.g., Karlsson, et al. (1986) *EMBO* 5:2377; Carter (1992) *Current Opinion in Biotechnology* 3:533-539; Muzcyzka (1992) *Current Top. Microbiol. Immunol.* 158:97-129; *Gene Targeting: A Practical Approach* (1992) ed. A. L. Joyner, Oxford University Press, NY). Several different approaches are feasible.

Alpha virus vectors, such as Venezuelan Equine Encephalitis (VEE) virus, Semliki Forest virus (SFV) and Sindbis virus vectors, can be used for efficient gene delivery. Replication-deficient vectors are available.

Additional literature describing viral vectors which could be used in the methods of the present invention include the following: Horwitz, M. S., Adenoviridae and Their Replication, in Fields, B., et al. (eds.) *Virology*, Vol. 2, Raven Press New York, pp. 1679-1721, 1990); Graham, F. et al., pp. 109-128 in *Methods in Molecular Biology*, Vol. 7: *Gene Transfer and Expression Protocols*, Murray, E. (ed.), Humana Press, Clifton, N.J. (1991); Miller, et al. (1995) *FASEB Journal* 9:190-199, Schreier (1994) *Pharmaceutica Acta Helvetiae* 68:145-159; Schneider and French (1993) *Circulation* 88:1937-1942; Curiel, et al. (1992) *Human Gene Therapy* 3:147-154; WO 95/00655; WO 95/16772; WO 95/23867; WO 94/26914; WO 95/02697 (Jan. 26, 1995); and WO 95/25071.

In some embodiments, the viral vector is a retrovirus/lentivirus, adenovirus, adeno-associated virus, alpha virus, vaccinia virus or a herpes simplex virus. In some embodiments, the viral vector is a lentiviral vector.

I. Engineered Primary Blood Dendritic Cells and Methods of Making

A. Engineered Primary Blood Dendritic Cells

In one embodiment, the invention provides an engineered primary blood dendritic cell, wherein the dendritic cell expresses a functional Tax protein from a T cell leukemia virus. In accordance with the invention, the primary blood dendritic cell is CD205+ and CD11c+. In some embodiments, the engineered primary blood dendritic cell is made by the methods as described herein.

In some embodiments, the engineered primary blood dendritic cell has a constitutive maturation and activation phenotype. In some embodiments, the dendritic cell expresses one or more dendritic cell maturation and activation markers. In some embodiments, the dendritic cell comprises one or more maturation and activation markers selected from the group consisting of CD83, CD80, CD86, CD70, CCR7 and HLA-DR.

In some embodiments, the engineered primary blood dendritic cell can be further characterized by the presence or absence of various markers, by their ability to produce various cytokines, and grow in suspension culture. In some embodiments, the engineered primary blood dendritic cell is TLR3+ and TLR4−. In some embodiments, the engineered primary blood dendritic cell comprises the cleaved form of TLR7. In some embodiments, the engineered primary blood dendritic cell expresses TLR9. In some embodiments, the engineered primary blood dendritic cell produces IL-1A and TNFα. In some embodiments, the engineered primary blood dendritic cell produces IL-15.

The presence or absence of certain markers can be assayed using known techniques, such as fluorescence-activated cell sorting (FACS).

In some embodiments, the engineered primary blood dendritic cell produces negligible levels of IL-10 and TGFβ. In some embodiments, the dendritic cell is capable of growth in suspension culture.

The source of the cells is not particularly limiting. In some embodiments, the engineered primary blood dendritic cell can be derived from blood cells from birds, fish, reptiles, amphibians, or mammals. In some embodiments, the cells are derived from blood cells from primates, rodents, such as rats, mice or guinea pigs, dogs or cats. In some embodiments, the cells are derived from blood cells from a human.

In some embodiments, the engineered primary blood dendritic cell further expresses c-Myc. In some embodiments, the engineered primary blood dendritic cell further expresses one or more of Mcl-1, Bcl-xL, Bcl-2, phosphorylated pRb, phosphorylated cdc2, phosphorylated Stat1, phosphorylated Stat3, and phosphorylated Stat5. In some embodiments, the transcription factors NF-κB, Stat3 and AP-1 are active.

The engineered primary blood dendritic cells can be genetically modified to express one or more HLA proteins. HLA is a major histocompatibility complex (MHC) antigen specific to humans. HLA-A, HLA-B and HLA-C are types of human MHC class I cell surface receptors. The receptor is a heterodimer, and is composed of a heavy α chain and smaller β chain. The α chain is encoded by a variant HLA-A, HLA-B or HLA-C gene, and the β chain is an invariant β2 microglobulin molecule. The β2 microglobulin protein is coded for by a separate region of the human genome. In some embodiments, the engineered primary blood dendritic cells can be genetically modified to express one or more of HLA-A, HLA-B or HLA-C. In one embodiment, the engineered primary blood dendritic cells are genetically modified to express HLA-A. In some embodiments, the engineered primary blood dendritic cells can be genetically modified to express HLA-A2.1. In some embodiments, the amino acid sequence of HLA-A2.1 is SEQ ID NO:15.

The engineered primary blood dendritic cells can be loaded with one or more antigens. In some embodiments, engineered primary blood dendritic cell harbors one or more antigens or antigenic fragments or variants thereof. In some embodiments, the antigen is a cancer antigen. In some embodiments, the antigen is an antigen from a pathogenic organism.

In some embodiments, the engineered primary blood dendritic cells can induce proliferation of naïve lymphocytes. In some embodiments, the engineered primary blood dendritic cells are capable of inducing proliferation of naïve lymphocytes in the absence of exogenously added IL-2.

In some embodiments, the engineered primary blood dendritic cell includes the cell lines ihv-DC1 and ihv-DC2 as described in Example 1.

In some embodiments, the engineered primary blood dendritic cell is capable of priming naïve lymphocytes (such as a population of PBMCs) to generate cytotoxic lymphocytes that recognize antigen. In some embodiments the engineered primary blood dendritic cell presents the antigen in an HLA-restricted manner. In some embodiments, the engineered primary blood dendritic cell is capable of priming naïve lymphocytes (such as a population of PBMCs) to generate cytotoxic lymphocytes capable of killing cells in a non-HLA restricted manner.

B. Methods of Making Engineered Primary Blood Dendritic Cell

The engineered primary blood dendritic cell of the invention can be prepared by a variety of methods and is not limiting. In some embodiments, the engineered primary blood dendritic cell is prepared according to the methods described herein.

In one embodiment, the invention provides a method of generating an engineered primary blood dendritic cell, comprising:
 i) providing a sample of cells comprising immature dendritic cells; and
 ii) expressing a functional Tax protein from a T cell leukemia virus in the cells.

In some embodiments, the method further comprises iii) culturing the cells to induce their maturation and activation. The culturing step to induce the maturation and activation of the engineered primary blood dendritic cell is not limiting. In some embodiments, the cells are cultured in the presence of one or more cytokines. In some embodiments, the cells are cultured in media comprising an effective amount of IL-2. In some embodiments, the concentration of IL-2 comprises at least about 10 units/ml. In some embodiments, the concentration of IL-2 is at least about 50 units/ml. In some embodiments, the concentration of IL-2 is at least about 100 units/ml. In some embodiments, the concentration of IL-2 ranges from about 100-200 units/ml. IL-2 can be provided in recombinant form. Recombinant IL-2 can be obtained from the NIH AIDS Reagent Program (Germantown, Md.).

In some embodiments, the method further comprises depleting T cells from the cultured cells.

In one embodiment, the invention provides a method of generating an engineered primary blood dendritic cell, comprising:
 i) providing a sample of cells comprising immature dendritic cells;
 ii) treating the cells in culture with an effective amount of phytohaemagglutinin (PHA);
 iii) treating the cells in culture with an effective amount of IL-2;
 iv) expressing a functional Tax protein from a T cell leukemia virus in the cells; and
 v) depleting T cells from the cultured cells.

In some embodiments, the sample of cells comprising immature dendritic cells comprises a sample of PBMCs. In some embodiments, the PBMCs are from a subject that is to be subsequently treated with the dendritic cells or T lymphocytes activated by the dendritic cells. In some embodiments, the PBMCs are isolated from a leukopak. In some embodiments, the PBMCs are prepared from healthy blood donors. For example, Leukopaks from healthy blood donors can be obtained from a blood bank. PBMCs can be isolated using the Ficoll-Paque method. For example, 10 ml of blood from leukopaks can be mixed with 10 ml of $Ca^{2+}/Mg^{2+}$-free PBS buffer in a 50 ml conical tube. 15 ml of Ficoll-Paque PLUS (GE Healthcare) can be pipted in a separate 50 ml tube. 20 ml of the diluted blood can be layered onto the Ficoll. The samples can be spun at 400×g for 30 min at room temperature (RT). The PBMCs layer is collected at the diluted plasma/Ficoll interface and PBS buffer can be added for a total volume of 40 ml, then spun at 200×g for 10 min at RT. The pellets can be washed with PBS and spun again at 200×g for 10 min at RT. The cell numbers can be counted and 2 million of fresh PBMCs can be stimulated with PHA (5 µg/ml) and IL-2 (100 u/ml).

In some embodiments, the concentration of PHA of part ii) is at least about 1 µg/ml. In some embodiments, the concentration of PHA ranges from about 1-30 µg/ml. In some embodiments, the concentration of PHA of part ii) ranges from about 1-5 µg/ml. In some embodiments, the concentration of PHA of part ii) is at least about 5 µg/ml. In some embodiments, the cells are treated for PHA from about 12 hours to about 36 hours. In some embodiments, the cells are treated for PHA for about 24 hours.

In some embodiments, the cells were treated with IL-2 after treatment with PHA. In some embodiments, the cells are treated with at least about 10 units/ml of IL-2. In some embodiments, the cells are treated with at least about 50 units/ml of IL-2. In some embodiments, the cells are treated with about 10-500 units/ml of IL-2 and cultured for a period of time in media comprising IL-2 prior to expression of functional Tax protein. In some embodiments, the cells are treated with about 100-200 units/ml IL-2 and cultured for a period of time in media comprising IL-2. In some embodiments, the cells are cultured for a period of time ranging from about 2-10 days in media comprising IL-2. In some embodiments, the cells are cultured in media comprising about 100-200 units/ml IL-2 for a period of time from about 4-5 days.

The cells are manipulated to express a functional Tax protein from a T cell leukemia virus. The functional Tax protein present in the dendritic cells as described herein in accordance with the invention is not expressed as a result of an infection of a T cell leukemia virus (i.e., a non-engineered virus or wild-type virus) of the immature dendritic cells. Instead, a nucleic acid encoding a functional Tax protein is delivered to the cell by other mechanisms, such as engineering a nucleic acid construct comprising a functional Tax protein and delivery of the construct to the immature dendritic cell. In some embodiments, the Tax protein is from a human T cell leukemia virus selected from the group consisting of HTLV-1, HTLV-2, HTLV-3 and HTLV-4. In some embodiments, the Tax protein is from HTLV-2, which is a virus that does not cause leukemia in humans.

In some embodiments, nucleic acid encoding a functional Tax protein can be engineered in a viral vector and used to transduce the cells. In some embodiments, the cells are transduced in the presence of about 10 µg/ml polybrene. In some embodiments, the viral vector is a retrovirus/lentivirus, adenovirus, adeno-associated virus, alpha virus, vaccinia virus or a herpes simplex virus. In some embodiments, the viral vector is a lentiviral vector.

In some embodiments, the functional Tax protein is prepared in a lentiviral vector and the cells are cultured and transduced as follows. The tax gene from HTLV-2 can be fused with a fragment encoding enhanced green fluorescence protein (EGFP), and the Tax2-GFP fusion fragment can be cloned into a lentivirus vector. In some embodiments, the Tax2-GFP fusion has the amino acid sequence of SEQ ID NO:16 and the nucleotide sequence of SEQ ID NO:17. To generate the Tax2-GFP lentivirus, the lentiviral Tax2-GFP vector can be co-transfected with a packaging plasmid mix containing the expression plasmids for VSV-G, Gag-Pol and Rev (Invitrogen) into 293 cells using SuperFect transfection reagent (Qiagen). The viral supernatants can be collected and can be subjected to ultracentrifugation at 25,000 rpm/4° C. for 2 hours. The virus pellets can be resuspended with RPMI640 medium supplemented with 10% heat-inactivated fetal bovine serum (FBS) (Sigma) and stored at −80° C. 2 million freshly isolated PBMCs can be stimulated with PHA (5 µg/ml) for 24 hours. The next day, the cells can be washed once with the complete RPM11640 medium, followed by adding recombinant IL-2 (100 units/ml). The activated PBMCs can be cultured for 4-5 days. 2 million activated PBMCs can be mixed with the Tax2-GFP lentivirus at MOI (multiplicity of infection) of about 20 plus adding polybrene (6 μg/ml). The cell-lentivirus mix is incubated in a cell culture incubator at 32° C./5% $CO_2$ for 16 hours. The next day, the transduced cells can be washed once with the complete RPM11640 medium and then placed in culture flask with the complete RPM11640 medium supplemented with recombinant IL-2 (100 units/ml). In some embodiments, 10% FBS in the complete medium can be replaced with 5% heat-inactivated human AB serum from Sigma.

In some embodiments, the transduced cells are further cultured in media comprising effective amounts of IL-2 to facilitate their maturation and activation. In some embodiments, the concentration of IL-2 comprises at least about 10 units/ml. In some embodiments, the concentration of IL-2 is at least about 50 units/ml. In some embodiments, the concentration of IL-2 is at least about 100 units/ml. In some embodiments, the transduced cells are cultured in media comprising about 100-200 units/ml of IL-2. In some embodiments, the transduced cells are further cultured in media comprising effective amounts of IL-2 for about 2-3 months. In some embodiments, the media comprises 100-200 units/ml of IL-2 and serum. In some embodiments, the media comprises about 10% fetal bovine serum and 100-200 units/ml of IL-2. In some embodiments the media comprises about 5% human serum and 100-200 units/ml of IL-2. In some embodiments, the transduced cells are cultured for about 2-3 months in media comprising IL-2 and human serum. In some embodiments, the media comprises 5% heat-inactivated human AB serum and 100-200 units/ml of IL-2. The media generally comprises a base media. The base media is not limiting. In some embodiments, the base media is complete RPMI1640 medium.

The T cells can be depleted from the cultured cells using known methods. In some embodiments, the T cells are depleted with a composition comprising a molecule that binds to T cells. In some embodiments, the T cells are depleted with an antibody. In some embodiments, the antibody is an anti-CD3 antibody. In some embodiments the antibody is conjugated to a magnetic bead. In some embodiments, the T cells are depleted by cell sorting or flow cytometry.

In some embodiments, the T cells are depleted as follows. Two to three weeks following lentiviral transduction, 10 million of the transduced cells can be incubated with 100 μl of anti-CD3 magnetic beads (Invitrogen) at 4° C. for 30 min. The cells that are not bound to the beads under a magnetic bar can be aspirated and cultured in the complete RPM11640 medium supplemented with IL-2 in a 6-well culture plate. In some embodiments, CD3-negatively selected cells can be examined with FACS to determine cell purity. In some embodiments, additional rounds of anti-CD3 negative selection can be performed if desired if the retrieved cell population is not pure.

In some embodiments, the cell population depleted of T cells can be further cultured in media comprising an effective amount of IL-2. In some embodiments, the concentration of IL-2 is about 100-200 units/ml. In some embodiments, the CD3-negative cell population is cultured in complete RPM11640 medium supplemented with 100-200 units/ml IL-2. In some embodiments, about two months following CD3 negative selection, the CD3-negative cell population can be analyzed with a panel of antibodies using FACS to determine their immunophenotypes.

In some embodiments, the engineered primary blood dendritic cell produced according to the methods has a constitutive maturation and activation phenotype. In some embodiments, the engineered primary blood dendritic cell comprises maturation and activation markers are selected from the group consisting of CD83, CD80, CD86, CD70, CCR7, 4-1BBL, and HLA-DR and combinations thereof.

In some embodiments, the method further comprises loading the primary blood dendritic cell with one or more antigens or antigenic fragments or variants thereof. In some embodiments, the method comprises transducing the cell with a viral vector encoding one or more antigens or antigenic fragments or variants thereof. In some embodiments, the antigen is a cancer antigen.

In some embodiments, the primary blood dendritic cell expresses human telomerase reverse transcriptase or an antigenic fragment or derivative thereof. In some embodiments, the human telomerase reverse transcriptase amino acid sequence comprises SEQ ID NO:9 and the nucleotide sequence comprises SEQ ID NO:10.

In some embodiments, the nucleic acid sequence of the human telomerase reverse transcriptase contains a nucleotide sequence that is highly identical, at least 90% identical, with a nucleotide sequence encoding a human telomerase reverse transcriptase polypeptide. In some embodiments, the nucleic acid sequence of the human telomerase reverse transcriptase comprises a nucleotide sequence that is at least 90%, 91%, 92%, 93%, 94%, 95%, 96%, 97%, 98% 99% or 100% identical with the nucleotide sequence set forth in SEQ ID NO:10.

In some embodiments, the polynucleotide encoding a human telomerase reverse transcriptase may include the coding sequence for the full-length polypeptide or a fragment thereof, by itself; or the coding sequence for the full-length polypeptide or fragment in reading frame with other coding sequence. The polynucleotide may also contain non-coding 5' and 3' sequences, such as transcribed, non-translated sequences, splicing and polyadenylation signals, ribosome binding sites and sequences that stabilize mRNA.

In some embodiments, the nucleotide sequence encoding a human telomerase reverse transcriptase includes nucleic acid molecules comprising a polynucleotide having a nucleotide sequence at least 90%, 91%, 92%, 93%, 94%, 95%, 96%, 97%, 98% 99% or 100% identical to (a) a nucleotide sequence encoding human telomerase reverse transcriptase having the amino acid sequence in SEQ ID NO:9; or (b) a nucleotide sequence complementary to the nucleotide sequences in (a).

In some embodiments, the human telomerase reverse transcriptase for use in the invention comprises SEQ ID NO:9. In some embodiments, the human telomerase reverse transcriptase comprises antigenic fragments or variants of SEQ ID NO:9. In some embodiments, the human telomerase reverse transcriptase comprising antigenic fragments or variants have at least 80% identity to SEQ ID NO:9. In some embodiments, the antigenic fragments or variants have at least 85%, 86%, 87%, 88%, 89%, 90%, 91%, 92%, 93%, 94%, 95%, 96%, 97%, 98% or 99% identity to the polypeptide of SEQ ID NO:9.

In some embodiments, the human telomerase reverse transcriptase comprises a fusion protein comprising a full length human telomerase reverse transcriptase or an antigenic fragment or derivative thereof. A fragment is a polypeptide having an amino acid sequence that entirely is the same as part but not all of the amino acid sequence of the aforementioned human telomerase reverse transcriptase. In some embodiments, a fragment may constitute at least about 250 contiguous amino acids identified in SEQ ID NO:9. In some embodiments, the fragment is at least about 250, 300, 350, 400, 450, 500, 550, 600, 650, 700, 750, 800, 850, 900, 950, 1000, or 1050 contiguous amino acids identified in SEQ ID NO:9.

In some embodiments the fragments include, for example, truncation polypeptides having the amino acid sequence of human telomerase reverse transcriptase, except for deletion of a continuous series of residues that includes the amino terminus, or a continuous series of residues that includes the carboxyl terminus or deletion of two continuous series of residues, one including the amino terminus and one including the carboxyl terminus.

Antigenic fragments or variants of human telomerase reverse transcriptase include polypeptides having an amino acid sequence at least 90% identical to SEQ ID NO: 9 or fragments thereof with at least 90% identity to the corresponding fragment of SEQ ID NO:9. Included in this group are variants of the defined sequence and fragment. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 1, 2, 3, 4, 5, 6, 7, 8, 9, 10 or more amino acids are substituted, deleted, or added in any combination.

In some embodiments, the antigen comprises a fusion protein. In some embodiments, the fusion protein comprises IκBα fused to the antigen. In some embodiments, the amino acid sequence of IκBα comprises SEQ ID NO:11 and the nucleotide sequence comprises SEQ ID NO: 12. In some embodiments, the fusion protein comprises a proteasomal target sequence of IκBΔ and an antigen, such as a cancer antigen. In some embodiments, the cancer antigen is a fragment of human telomerase reverse transcriptase. In some embodiments, the fusion protein comprises IκBα fused to a fragment of human telomerase reverse transcriptase and comprising an amino acid sequence of SEQ ID NO: 13 and a nucleotide sequence comprising SEQ ID NO:14.

In some embodiments, the method further comprises genetically modifying the primary blood dendritic cell to express one or more HLA proteins. In some embodiments, the method comprises genetically modifying the primary blood dendritic cell to express one or more of HLA-A, HLA-B, or HLA-C. In some embodiments, the primary blood dendritic cell has been genetically modified to express HLA-A2.1. In some embodiments, the amino acid sequence of HLA-A2.1 is SEQ ID NO:15.

In some embodiments, the functionality of the engineered primary blood dendritic cells can be determined by their ability to prime naïve lymphocytes. In some embodiments, this is performed with an assay called a mixed leukocyte reaction (MLR). In some embodiments, about 2 million of unstimulated (naïve) allogeneic PBMCs are mixed with engineered primary blood dendritic cells (e.g., $2 \times 10^4$ cells) at the ratio of about 100:1 without adding any cytokines and growth factors. 10-14 days later, IL-2 can be added into the cell cultures. The immunophenotypes and the tumor killing activity of the proliferating cells can be determined with FACS and a cytotoxic assay, respectively.

In some embodiments, the invention provides a primary blood dendritic cell prepared according to any of the above described methods.

II. Engineered Monocyte-Derived Dendritic Cell and Methods of Making

A. Engineered Monocyte-Derived Dendritic Cell

In some embodiments, the invention provides an engineered monocyte-derived dendritic cell, wherein the dendritic cell expresses a functional Tax protein from a T cell leukemia virus. The monocyte-derived dendritic cell is CD205+.

The source of the cells is not particularly limiting. In some embodiments, the engineered monocyte-derived dendritic cell can be derived from monocyte cells from birds, fish, reptiles, amphibians, or mammals. In some embodiments, the cells are derived from monocyte cells from primates, rodents, such as rats, mice or guinea pigs, dogs or cats. In some embodiments, the cells are derived from monocyte cells from a human.

In some embodiments, the engineered monocyte-derived dendritic cell has a constitutive maturation and activation phenotype. In some embodiments, engineered monocyte-derived dendritic cell expresses one or more dendritic cell maturation and activation markers. In some embodiments, the dendritic cell maturation and activation markers are selected from the group consisting of CD83, CD80, CD86, and CD70.

In some embodiments, the engineered monocyte-derived dendritic cell can be further characterized by the presence or absence of various markers, by their ability to produce various cytokines, and their growth characteristics. In some embodiments, the engineered monocyte-derived dendritic cell expresses the cleaved form of TLR7. In some embodiments, the engineered monocyte-derived dendritic cell produces IL-1A and TNFα. In some embodiments, the engineered monocyte-derived dendritic cell produces TGFβ. In some embodiments, the engineered monocyte-derived dendritic cell produces IL-15. In some embodiments, the engineered monocyte-derived dendritic cell expresses one or more of the following: c-Myc, Mcl-1, Bcl-xL, Bcl-2, phosphorylated pRb, phosphorylated cdc2, phosphorylated Stat1, phosphorylated Stat3, and phosphorylated Stat5. In some embodiments, the engineered monocyte-derived dendritic cell further expresses 4-1BBL and/or CD4. In some embodiments, the engineered monocyte-derived dendritic cell is TLR3+ and TLR4−. In some embodiments, the engineered monocyte-derived dendritic cell is capable of growth in suspension culture. In some embodiments, the monocyte-derived dendritic cell is capable of proliferating for up to three months in culture.

In some embodiments, the engineered monocyte-derived dendritic cell is capable of inducing proliferation of naïve lymphocytes in the absence of exogenously added IL-2.

The engineered monocyte-derived dendritic cell can be genetically modified to express one or more HLA proteins. In some embodiments, the e engineered monocyte-derived dendritic cells can be genetically modified to express one or more of HLA-A, HLA-B or HLA-C. In some embodiments, the engineered monocyte-derived dendritic cells are genetically modified to express HLA-A. In some embodiments, the engineered monocyte-derived dendritic cells can be genetically modified to express HLA-A2.1. In some embodiments, the amino acid sequence of HLA-A2.1 is SEQ ID NO:15.

The engineered monocyte-derived dendritic cells can be loaded with one or more antigens. In some embodiments, the engineered monocyte-derived dendritic cell presents one or more antigens or antigenic fragments or variants thereof. In some embodiments, the antigen is a cancer antigen. In some embodiments, the antigen is an antigen from a pathogenic organism.

The loading of the antigen on the engineered monocyte-derived dendritic cell is not limiting. In some embodiments, the antigen can be loaded using methods as described herein, including transfection, transduction, electroporation and peptide pulsing. In some embodiments, the antigen is introduced by viral transduction. In some embodiments, the virus is a lentivirus.

In some embodiments, the engineered monocyte-derived dendritic cell can induce proliferation of naïve lymphocytes.

In some embodiments, the engineered monocyte-derived dendritic cell is capable of priming naïve lymphocytes (such as a population of PBMCs) to generate cytotoxic lymphocytes that recognize antigen. In some embodiments the engineered monocyte-derived dendritic cell presents the antigen in an HLA-restricted manner. In some embodiments, the engineered monocyte-derived dendritic cell is capable of priming naïve lymphocytes (such as a population of PBMCs) to generate cytotoxic lymphocytes capable of killing cells in a non-HLA restricted manner.

B. Methods of Making Engineered Monocyte-Derived Dendritic Cell

The engineered monocyte-derived dendritic cell of the invention can be prepared by a variety of methods and is not limiting. In some embodiments, the engineered monocyte-derived dendritic cell is prepared according to the methods described herein.

In one embodiment, the invention provides a method of generating monocyte-derived dendritic cells, comprising:
i) providing a sample of cells comprising immature dendritic cells derived from monocytes; and
ii) expressing a functional Tax protein from a T cell leukemia virus in the cells.

In some embodiments, the method further comprises, prior to part i) culturing monocyte cells to induce their differentiation into immature dendritic cells. In some embodiments, differentiation is induced by contacting the monocytes with a culture medium comprising an effective amount of a composition that induces the differentiation of monocytes into immature dendritic cells, such as, but not limited to, GM-CSF; GM-CSF and IL-4; GM-CSF and IL-13; GM-CSF and IL-15; and IFNα. In some embodiments, the monocytes are cultured in media comprising effective amounts of GM-CSF and IL-4 to induce differentiation to immature dendritic cells.

In some embodiments, the method further comprises a step after part ii) comprising culturing the cells to induce their maturation and activation. The culturing step to induce the maturation and activation of the monocyte-derived dendritic cell is not limiting. In some embodiments, the cells are cultured in the presence of one or more cytokines. In some embodiments, the cells are further cultured in media comprising an effective amount of GM-CSF and IL-4.

A variety of methods for collecting monocytes and PBMCs comprising monocytes from a subject are known to those of ordinary skill in the art. See for example, gambrobct.com/Products_&_Services/for detailed information on leukapheresis for the collection PBMCs and elutriation for the purification of monocytes. In one embodiment, PBMCs are obtained by collecting blood in a heparinized syringe, dilution in PBS, layering over Histopaque 1077 (Sigma), centrifugation and recovery of PBMCs at the interface. See Woodhead et al. (2000) *International Immunol* 12:1051-1061. Additional methods of collecting, purifying or fractionating PBMCs are known to those of ordinary skill in the art.

In some embodiments, the method uses an enriched monocyte culture. Methods of enriching for monocytes are known to those of ordinary skill in the art, and include, but are not limited to, density gradient centrifugation (e.g, dilute Ficoll density gradient centrifugation, dilute Percoll density gradient centrifugation, etc.), elutriation, adherence to plastic, tangential flow filtration, fluorescence activated cell sorting (FACS), immunological cell separation techniques (antibody panning to select monocytes or to remove non-monocytes (e.g., leukocytes, macrophages, granulocytes, etc), differential lysis, magnetic cell sorting, etc.), culture in plastic culture bags coated with plastic microcarrier beads, etc. See, for example, O'Doherty et al. (1993) *J Exp Med* 178:1067-1076; Young et al. (1990) *J Exp Med* 171:1315-1332; Freudenthal et al. (1990) *PNAS* 87:7698-7702; Bernhard et al. (1995) *Cancer Res* 55:1099-1104; Caux et al. (1992) *Nature* 360:258-261; Read et al. (2003) "Evaluation of a Closed Automated System to Isolate Peripheral Blood Monocytes for Dendritic Dell (DC) Immunotherapy", Ninth annual meeting of the ISCT; Mu et al. (2003) *Scand J Immunol* 58:578-586; Maffei et al. (2000) *Transfusion* 40:1419-1420; mitenyibiotec.com; Meyer-Wentrup et al. (2003) *J Hematother Stem Cell Res* 12:289-299; and WO 2004/000444, the contents of which are incorporated by reference. For example, magnetic cell sorting can be used to enrich form monocytes by positive selection (CD14+ cells) or by negative selection (i.e., removal of cells that are not monocytes; e.g., CD3+, CD19+ and CD2+ cells).

In some embodiments, monocytes are enriched from a leukapheresis product by elutriation, an automated method to isolate monocytes from the subject leukapheresis. Methods of leukapheresis are known in the art. For example, elutriation can be performed on the Gambro BCT Elutra™ Cell Separation System (Gambro BCT, Lakewood, Colo.). Elutriation buffer can be prepared by adding 1000 mL of 5% Human Albumin Serum (HSA) to a 4 L bag of Hank's Balanced Salt Solution (HBSS). The cells can be fractionated by elutriation according to the manufacturer's protocol. In one embodiment, a modified version of the manufacturer's (Gambro) protocol is used for elutriation, where the final rotor off fraction is the fourth fraction instead of the fifth fraction. CBC with differential analysis can performed on the monocyte fraction to verify purity and recovery. In some embodiments, monocyte purity can be assessed by immunophenotyping with CD14.

In some embodiments, the monocytes are enriched prior to differentiation of the cells into dendritic cells. In particular, PBMCs may be further purified, or monocytes may be enriched from PBMCs during this period of incubation. In one embodiment, monocytes can be enriched from PBMCs after the incubation period by culture in a container (preferably a plastic container) and selection for adherent monocytes.

In one embodiment, monocytes are cultured in a medium comprising a composition that induces the differentiation of monocytes into immature or mature dendritic cells. Compositions which induce the differentiation of monocytes into immature dendritic cells are known to those of skill in the art. Such compositions include, but are not limited to, GM-CSF+IL-4; GM-CSF+IL-13; GM-CSF+IL-15; IFNα; and GM-CSF+TNFα. In some embodiments, the composition which induces differentiation is GM-CSF+IL-4. In some embodiments, the concentrations of GM-CSF and IL-4 may range from about 400 to 2000 units/ml of each cytokine. In some embodiments, the concentration of GM-CSF and IL-4 is 500 to 1000 units/ml of each cytokine. In one embodiment, the monocytes are contacted with GM-CSF and IL-4 for about 4-7 days, in some embodiments, for about 5-6 days, during which time the monocytes differentiate into immature dendritic cells. Conditioned media which comprises effective amounts of GM-CSF and IL-4 can also be utilized. In some embodiments, the culturing comprises culturing the cells in media comprising conditioned media from GM-CSF-Fc4/IL-4-Fc4 producing 293 cells. In some embodiments, the cells are cultured in media comprising the conditioned medium at about a 1:10 dilution.

Following differentiation of monocytes into immature dendritic cells and expressing a functional Tax protein, in some embodiments, the immature dendritic cells can be matured into mature dendritic cells. In one embodiment, the immature dendritic cell is matured by contact with a medium comprising effective amounts of IL-2. In some embodiments, the concentration of IL-2 comprises at least about 10 units/ml. In some embodiments, the concentration of IL-2 is at least about 50 units/ml. In some embodiments, the concentration of IL-2 is at least about 100 units/ml. In some embodiments, the concentration of IL-2 ranges from about 100-200 units/ml.

In another embodiment, the invention provides a method of generating monocyte-derived dendritic cells, comprising:
 i) providing adherent monocyte cells;
 ii) culturing the cells in media comprising an effective amount of GM-CSF and IL-4;
 iii) expressing a functional Tax protein from a T cell leukemia virus in the cells;
 iv) culturing the functional Tax protein expressing cells in media comprising an effective amount of GM-CSF and IL-4.

In some embodiments, the adherent monocyte cells are isolated from PBMCs. In some embodiments, the adherent monocytes are isolated from about 4 million PBMCs. In some embodiments, following the steps of expressing the functional Tax protein and culturing in media comprising an effective amount of GM-CSF and IL-4, the method further comprises culturing the cells in media comprising IL-2 (e.g., comprising about 100-200 units/ml).

In some embodiments, the IL-4 and/or GM-CSF is fused to Fc4. In some embodiments, the IL-4 and/or GM-CSF can be provided by conditioned media. In some embodiments, the culturing of part ii) comprises culturing the cells in media comprising conditioned media from GM-CSF-Fc4/IL-4-Fc4 producing 293 cells. In some embodiments, the cells are cultured in media comprising the conditioned medium at about a 1:10 dilution for about 7 days.

The cells are manipulated to express a functional Tax protein from a T cell leukemia virus. The functional Tax protein present in the dendritic cells as described herein in accordance with the invention is not expressed as a result of an infection of a T cell leukemia virus (i.e., a non-engineered virus or wild-type virus) of the immature dendritic cells. Instead, a nucleic acid encoding a functional Tax protein is delivered to the cell by other mechanisms, such as engineering a nucleic acid construct comprising a functional Tax protein and delivery of the construct to the immature dendritic cell. In some embodiments, the Tax protein is from a human T cell leukemia virus selected from the group consisting of HTLV-1, HTLV-2, HTLV-3 and HTLV-4. In some embodiments, the Tax protein is from HTLV-2, which is a virus that does not cause leukemia in humans.

In some embodiments, nucleic acid encoding a functional Tax protein can be engineered in a viral vector and used to transduce the cells. In some embodiments, the cells are transduced in the presence of an effective amount of polybrene, e.g., about 10 µg/ml polybrene. In some embodiments, the viral vector is a retrovirus/lentivirus, adenovirus, adeno-associated virus, alpha virus, vaccinia virus or a herpes simplex virus. In some embodiments, the viral vector is a lentiviral vector.

The base media for culturing the cells is not limiting. In some embodiments, the media comprises RPMI1640 medium with about 10% fetal bovine serum. In some embodiments, the culturing part iv) comprises culturing the Tax protein expressing cells in RPMI1640 medium with 10% FBS in the presence of effective amounts of GM-CSF-Fc4 and IL-4-Fc4 for about 5-7 days, followed by maintaining the cells in culture in the presence of about 100-200 units/ml of IL-2.

In some embodiments, the method further comprises activating the monocyte-derived dendritic cells. In some embodiments, the monocyte-derived dendritic are stimulated with effective amounts of TNFα and LPS. In some embodiments, the TNFα is administered in an amount of from about 10-250 ng/ml and LPS is administered in an amount of from about 1-5 µg/ml. In some embodiments, the cells are stimulated for 1-5 days. In some embodiments, the cells are stimulated for about 2 days.

In some embodiments, the monocyte-derived dendritic cell produced by the method has a constitutive maturation and activation phenotype. In some embodiments, the monocyte-derived dendritic cell expresses one or more dendritic cell maturation and activation markers. In some embodiments, the monocyte-derived dendritic cell maturation and activation markers are selected from the group consisting of CD83, CD80, CD86, and CD70. In some embodiments, the monocyte-derived dendritic cell further expresses 4-1BBL and/or CD4.

In some embodiments, the monocyte-derived dendritic cell is capable of proliferating for up to three months in culture.

In some embodiments, the method further comprises loading the monocyte-derived dendritic cell with one or more antigens or antigenic fragments or variants thereof. In some embodiments, the method comprises transducing the cell with a viral vector encoding one or more antigens or antigenic fragments or variants thereof. In some embodiments, the antigen is a cancer antigen. In some embodiments, the monocyte-derived dendritic cell expresses human telomerase reverse transcriptase or an antigenic fragment or variant thereof. In some embodiments, the cancer antigen comprises a fusion protein comprising a proteasomal target sequence of IκBα and a fragment of human telomerase reverse transcriptase. In some embodiments, the fusion protein comprises SEQ ID NO:13.

In some embodiments, the method further comprises genetically modifying the monocyte-derived dendritic cell to express one or more HLA proteins. In some embodiments, the method comprises transducing the cell with a viral vector encoding one or more HLA proteins. In some embodiments, the method comprises genetically modifying the monocyte-derived dendritic cell to express one or more of HLA-A, HLA-B, or HLA-C. In some embodiments, the dendritic cell has been genetically modified to express HLA-A2.1. In some embodiments, the amino acid sequence of HLA-A2.1 is SEQ ID NO:15.

In some embodiments, the functionality of the engineered monocyte-derived dendritic cells can be determined by their ability to prime naïve lymphocytes. In some embodiments, this is performed with an assay called a mixed leukocyte reaction (MLR). In some embodiments, about 2 million of unstimulated (naïve) allogeneic PBMCs are mixed with engineered monocyte-derived dendritic cells (e.g., $2\times10^4$ cells) at the ratio of about 100:1 without adding any cytokines and growth factors. 10-14 days later, IL-2 can be added into the cell cultures. The immunophenotypes and the tumor killing activity of the proliferating cells can be determined with FACS and a cytotoxic assay, respectively.

In some embodiments, the invention provides a monocyte-derived dendritic cell prepared according to any of the above described methods.

III. Methods of Producing Cytotoxic T Lymphocytes

In another embodiment, the invention provides a method for producing cytotoxic T lymphocytes, comprising culturing primary blood dendritic cells of the invention with cells comprising naïve lymphocytes for a period of time, whereby cytotoxic T lymphocytes are produced.

In another embodiment, the invention provides a method for producing cytotoxic T lymphocytes, comprising culturing monocyte-derived dendritic cells of the invention with cells comprising naïve lymphocytes for a period of time, whereby cytotoxic T lymphocytes are produced.

In another embodiment, the invention provides a method for producing cytotoxic T lymphocytes, comprising
  i) culturing primary blood dendritic cells of the invention together with cells comprising naïve lymphocytes for a first period of time to create a mixed culture of cells; and
  ii) treating the mixed culture of cells with an effective amount of IL-2 and continuing to culture the cells for a second period of time,
  whereby cytotoxic T lymphocytes are produced.

In another embodiment, the invention provides a method for producing cytotoxic T lymphocytes, comprising
  i) culturing monocyte-derived dendritic cells of the invention together with cells comprising naïve lymphocytes for a first period of time to create a mixed culture of cells; and
  ii) treating the mixed culture of cells with an effective amount of IL-2 and continuing to culture the cells for a second period of time,
  whereby cytotoxic T lymphocytes are produced.

In some embodiments, the cells comprising naïve lymphocytes comprise naïve PBMCs. In some embodiments, the naïve lymphocytes are isolated from leukopaks. In some embodiments, the naïve lymphocytes and the dendritic cells are allogeneic.

The ratio of dendritic cells to naïve PBMCs is not particularly limiting. In some embodiments, the ratio of dendritic cells to naïve PBMCs is about 1:10, about 1:25, about 1:50, about 1:100, about 1:250 or about 1:500. In some embodiments, the ratio of dendritic cells to naïve PBMCs is about 1:100.

In some embodiments, the culturing of step i) is conducted without addition of exogenous cytokines. In some embodiments, the first period of time is about 2-3 days.

In some embodiments, the concentration of IL-2 comprises at least about 10 units/ml. In some embodiments, the concentration of IL-2 is at least about 50 units/ml. In some embodiments, the concentration of IL-2 is at least about 100 units/ml. In some embodiments, the concentration of the IL-2 is about 100-200 units/ml. In some embodiments, the second period of time is from about 2-6 weeks.

In some embodiments, the cytotoxic T lymphocytes are antigen specific and induce cytolysis of target cells in an HLA-restricted manner.

In some embodiments, the cytotoxic T lymphocytes comprise CD3+/CD56+ T cells capable of killing target cells in a non-HLA-restricted manner. In some embodiments, the dendritic cells express 4-1BBL. In some embodiments, the dendritic cells have been engineered to express 4-1BBL. In some embodiments, the non-HLA-restricted killing of cells is mediated by ligand binding of NKG2D.

IV. Methods of Treatment with Cytotoxic T Lymphocytes

In another embodiment, the invention provides a method of treating a disease or condition in a subject, comprising administering to the subject an effective amount of cytotoxic T lymphocytes, wherein the cytotoxic T lymphocytes are produced using an engineered primary blood dendritic cell of the invention.

In another embodiment, the invention provides a method of treating a disease or condition in a subject, comprising administering to the subject an effective amount of cytotoxic T lymphocytes, wherein the cytotoxic T lymphocytes are produced using an engineered primary blood dendritic cell that has been produced according to a method of the invention.

In another embodiment, the invention provides a method of treating a disease or condition in a subject, comprising administering to the subject an effective amount of cytotoxic T lymphocytes, wherein the cytotoxic T lymphocytes are produced using an engineered monocyte-derived dendritic cell of the invention.

In another embodiment, the invention provides a method of treating a disease or condition in a subject, comprising administering to the subject an effective amount of cytotoxic T lymphocytes, wherein the cytotoxic T lymphocytes are produced using an engineered monocyte-derived dendritic cell that has been produced according to a method of the invention.

In some embodiments about $1\times10^8$ to $1\times10^{10}$ cytotoxic T lymphocytes are administered per injection. In some embodiments, about $5\times10^9$ cells are administered per injection.

In some embodiments, the disease to be treated is cancer. In some embodiments, the cancer cells express MICA/B. In some embodiments, the cancer is breast cancer.

In another embodiment, the invention provides a pharmaceutical composition, comprising an effective amount of cytotoxic T lymphocytes that are produced according to the methods of the invention.

The cytotoxic T lymphocytes are administered in a pharmaceutically acceptable carrier. In some embodiments, the cytotoxic T lymphocytes are frozen in the presence of a cryoprotectant, e.g., for storage and/or transport, and subsequently thawed prior to administration. See part V. below for exemplary cryoprotectant compositions.

The cells can be administered to the subject or patient using methods known in the medical arts. In some embodiments, the cells are injected into the subject. In some embodiments, the cells are implanted in a subject. The cells can be administered as a single dose or in multiple doses over a period of time. In some embodiments, the cells are administered about every 1-2 weeks, about every 3 weeks, about every 4 weeks, about every 5 weeks, about every 6 weeks, about every 7 weeks, about every 8 weeks, about every 3 months, about every 4 months, about every 5 months, about every 6 months, or about every year.

In some embodiments, the methods of the present invention are combined with one or more other known treatments. For the treatment of cancer, one or more other known treatments can include radiation, surgery, chemotherapy or administration of other anti-cancer agents and combinations thereof. In some embodiments, the treatment of the invention is combined with a chemotherapeutic agent.

V. Dendritic Cell Vaccines and Methods of Use

The dendritic cells described herein and the methods for their preparation are particularly useful for preparing vaccines. Thus, related dendritic cell compositions and vaccines are provided herein. In one embodiment, the vaccine is autologous to the subject. In some embodiments, the vaccine is allogeneic to the subject. In some embodiments, the dendritic cell vaccine is loaded with antigen from a cancer cell or pathogen present in the subject.

The dendritic cells, whether mature or immature, antigen loaded or not, can be frozen in a composition comprising a cryoprotectant. Numerous cryoprotectants are known to those of skill in the art. Examples of cryoprotectants include, but are not limited to, dimtheylsulfoxide (DMSO), glycerol, ethanol, methanol, acetamide, glycerol monoacetate, propane-diol, polyethylene glycol, ethylene glycol, i-erythritol, D-ribitol, D-mannitol, D-sorbitol, D-lactose, i-inositol, choline chloride, amino acids, albumin (preferably human serum albumin), polyvinyl pyrrolidone, dextran, sucrose, Ficoll, inorganic salts, and hydroxyethyl starch. In a preferred embodiment, the cryoprotectant is DMSO. In some embodiments, the concentration of DMSO is 2-20%, more preferably 5-15%, and most preferably approximately 10%. Also, the freezing medium may contain one or more polyol compounds derived from carbohydrates, such as glucose, dextrose, sucrose, etc., preferably in a concentration of from 2-30%, more preferably from 5-10%, most preferably 5% dextrose. Methods for freezing dendritic cells are known to those of skill in the art. See, for example U.S. Patent Application Pub. No. 2004/0253574, the contents of which are incorporated by reference. In some embodiments, the cryoprotectant is dimethylsulfoxide (DMSO). In some embodiments, the concentration of DMSO is 5% to 20%. Most preferably, the concentration of DMSO in the composition is approximately 10%.

Other suitable formulations for administration can include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, immunostimulants, cytokines and adjuvants.

In one embodiment, the therapeutic cells are suspended in heat-inactivated autologous plasma and 10% dextrose, at a final concentration of about $1\times10^8$ cells/ml. These cells are then diluted 1:1 with a mixture of heat-inactivated autologous plasma and 20% DMSO in heat inactivated autologous plasma which contains 5% dextrose and 10% DMSO. The final filled formulation is stored in a container suitable for cryopreservation. The vaccine is then frozen and stored at ≤150° C. in a dry liquid nitrogen freezer. The vaccine can be ready for administration alter thawing, without the need for washing and resuspending.

In some embodiments, the invention provides for the use of an antigen-loaded dendritic cell according to the invention for the preparation of a frozen medicament for the treatment or prevention of disease such as cancer or pathogen infection, wherein the medicament comprises a pharmaceutically acceptable vehicle and is ready for administration upon thawing.

In another embodiment, the invention provides a method of vaccinating a subject, comprising:
i) thawing a frozen dendritic cell vaccine of the invention; and
ii) administering the thawed vaccine to the subject.

In another embodiment, the invention provides a method of treating a disease or condition in a subject, comprising administering to the subject an effective amount of an engineered primary blood dendritic cell of the invention.

In another embodiment, the invention provides a method of treating a disease or condition in a subject, comprising administering to the subject an effective amount of an engineered monocyte-derived dendritic cell of the invention.

The dendritic cell vaccine can be administered by a variety of methods, such as, but not limited to, injection (e.g., subcutaneous, intradermal, intravenous, intralymphatic, intraarticular, intramuscular, intraperitoneal), by continuous infusion, sustained release from implants, etc. In some embodiments, the dendritic cell vaccine is administered at two to four week intervals. The dendritic cell vaccine can be administered with physiologically acceptable carriers, buffers, diluents, adjuvants, immunomodulators, etc. In some embodiments, the dendritic cell vaccine is autologous to the patient it is administered to, or is HLA matched.

The dose of cells (e.g., activated T cells, or dendritic cells) administered to a subject is in an effective amount, effective to achieve the desired beneficial therapeutic response in the subject over time, such as to inhibit growth of cancer cells, or to inhibit infection. In one embodiment, the dose is approximately $10^7$-$10^{10}$ cells. Biological response modifiers are optionally added for treatment by the dendritic cells or activated T cells of the invention. For example, in some embodiments, the cells are optionally administered with an adjuvant, or cytokine such as GM-CSF, IL-12 or IL-2. In some embodiments, the dendritic cells are irradiated prior to administration to the subject. In some embodiments, about $1\times10^8$ to about $1\times10^{10}$ cells administered per injection.

In some embodiments, the disease to be treated is cancer. In some embodiments, the cancer cells express MICA/B. In some embodiments, the cancer is breast cancer.

The cells can be administered to the subject or patient using methods known in the medical arts. In some embodiments, the cells are injected into the subject. In some embodiments, the cells are implanted in a subject. The cells can be administered as a single dose or in multiple doses over a period of time. In some embodiments, the cells are administered about every 1-2 weeks, about every 3 weeks, about every 4 weeks, about every 5 weeks, about every 6 weeks, about every 7 weeks, about every 8 weeks, about every 3 months, about every 4 months, about every 5 months, about every 6 months, or about every year.

In some embodiments, the methods of the present invention are combined with one or more other known treatments. For the treatment of cancer, one or more other known treatments can include radiation, surgery, chemotherapy or administration of other anti-cancer agents and combinations thereof. In some embodiments, the treatment of the invention is combined with a chemotherapeutic agent.

VI. Sample Embodiments

This section describes exemplary compositions and methods of the invention, presented without limitation, as a series of paragraphs, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

1. An engineered, wherein the dendritic cell expresses a functional Tax protein from a T cell leukemia virus.
2. The dendritic cell of paragraph 1, wherein the Tax protein is from a human T cell leukemia virus selected from the group consisting of HTLV-1, HTLV-2, HTLV-3 and HTLV-4.
3. The dendritic cell of any of paragraphs 1-2, wherein the Tax protein is from HTLV-2.
4. The dendritic cell of any of claims 1-3, wherein the dendritic cell has a constitutive maturation and activation phenotype.
5. The dendritic cell of any of paragraphs 1-4, wherein the dendritic cell is a human cell.
6. The dendritic cell of any of paragraphs 1-5, wherein the dendritic cell is CD205+.
7. The dendritic cell of any of paragraphs 1-6, wherein the dendritic cell is CD11c+.
8. The dendritic cell of any of paragraphs 1-7, wherein the dendritic cell expresses one or more dendritic cell maturation and activation markers.
9. The dendritic cell of paragraph 8, wherein the dendritic cell maturation and activation markers are selected from the group consisting of CD83, CD80, CD86, CD70, CCR7 and HLA-DR.
10. The dendritic cell of any of paragraphs 1-10, wherein the cells are capable of growth in suspension culture.
11. The dendritic cell of any of paragraphs 1-10, wherein the dendritic cell is TLR3+ and TLR4−.
12. The dendritic cell of any of paragraphs 1-11, wherein the cell expresses the cleaved form of TLR7.
13. The dendritic cell of any of paragraphs 1-12, wherein the cell expresses TLR9.
14. The dendritic cell of any of paragraphs 1-13, wherein the cells produce IL-1A and TNFα.
15. The dendritic cell of any of paragraphs 1-14, wherein the cells produce IL-15.
16. The dendritic cell of any of paragraphs 1-15, wherein the cells produce negligible levels of IL-10 and TGFβ.
17. The dendritic cell of any of paragraphs 1-16, wherein the cells express c-Myc.
18. The dendritic cell of any of paragraphs 1-17, wherein the transcription factors NF-κB, Stat3 and AP-1 are active.
19. The dendritic cell of any of paragraphs 1-18, wherein the cell is capable of inducing proliferation of naïve lymphocytes in the absence of exogenously added IL-2.
20. The dendritic cell of any of paragraphs 1-19, wherein the cell has been genetically modified to express one or more HLA proteins.
21. The dendritic cell of any of paragraphs 1-20, wherein the cell has been genetically modified to express HLA-A2.1.
22. The dendritic cell of any of paragraphs 1-21, wherein the cell presents one or more antigens or antigenic fragments or variants thereof.
23. The dendritic cell of any of paragraphs 1-22, wherein the antigen is a cancer antigen.
24. The dendritic cell of any of paragraphs 1-23, wherein the cell expresses human telomerase reverse transcriptase or an antigenic fragment or variant thereof.
25. The dendritic cell of paragraph 24, wherein the antigen comprises a fusion protein comprising full length IκBα and a fragment comprising amino acids 301-700 of human telomerase reverse transcriptase.
26. The dendritic cell of paragraph 25, wherein the fusion protein comprises SEQ ID NO:13.
27. The dendritic cell of any of paragraphs 1-26, wherein the cells present the cancer antigen in an HLA-restricted manner.
28. The dendritic cell of any of paragraphs 1-27, wherein the cancer antigen is introduced by viral transduction.
29. The dendritic cell of any of paragraphs 1-28, wherein the virus is a lentivirus.
30. The dendritic cell of any of paragraphs 1-29, wherein the dendritic cell is capable of priming naïve PBMCs to generate cytotoxic lymphocytes that recognize antigen.
31. The dendritic cell of any of paragraphs 1-30, wherein the dendritic cell is capable of priming naïve PBMCs to generate cytotoxic lymphocytes capable of killing cells in a non-HLA restricted manner.
32. An engineered monocyte-derived dendritic cell, wherein the dendritic cell expresses a functional Tax protein from a T cell leukemia virus.
33. The dendritic cell of paragraph 32, wherein the Tax protein is from a human T cell leukemia virus selected from the group consisting of HTLV-1, HTLV-2, HTLV-3 and HTLV-4.
34. The dendritic cell of any of paragraphs 32-33, wherein the Tax protein is from HTLV-2.
35. The dendritic cell of any of paragraphs 32-34, wherein the dendritic cell has a constitutive maturation and activation phenotype.
36. The dendritic cell of any of paragraphs 32-35, wherein the dendritic cell is a human cell.
37. The dendritic cell of any of paragraphs 32-36, wherein the dendritic cell is CD205+.
38. The dendritic cell of any of paragraphs 32-37, wherein the dendritic cell expresses one or more dendritic cell maturation and activation markers.
39. The dendritic cell of paragraph 38, wherein the dendritic cell maturation and activation markers are selected from the group consisting of CD83, CD80, CD86, and CD70.
40. The dendritic cell of paragraph 38, wherein the dendritic cell further expresses 4-1BBL and/or CD4.
41. The dendritic cell of any of paragraphs 32-40, wherein the cell is capable of growth in suspension culture.
42. The dendritic cell of any of paragraphs 32-41, wherein the cell is capable of proliferating for up to three months in culture.
43. The dendritic cell of any of paragraphs 32-42, wherein the cell is TLR3+ and TLR4−.
44. The dendritic cell of any of paragraphs 32-43, wherein the cell expresses the cleaved form of TLR7.
45. The dendritic cell of any of paragraphs 32-44, wherein the cell produces IL-1A and TNFα.
46. The dendritic cell of any of paragraphs 32-45, wherein the cell produces TGFβ.
47. The dendritic cell of any of paragraphs 32-46, wherein the cell produces IL-15.
48. The dendritic cell of any of paragraphs 32-47, wherein the cell expresses c-Myc.
49. The dendritic cell of any of paragraphs 32-48, wherein the cell is capable of inducing proliferation of naïve lymphocytes in the absence of exogenously added IL-2.
50. The dendritic cell of any of paragraphs 32-49, wherein the cell has been genetically modified to express one or more HLA proteins.

51. The dendritic cell of any of paragraphs 32-50, wherein the cell has been genetically modified to express HLA-A2.1.
52. The dendritic cell of any of paragraphs 32-51, wherein the cells express one or more antigens or antigenic fragments or variants thereof.
53. The dendritic cell of any of paragraphs 32-52, wherein the antigen is a cancer antigen.
54. The dendritic cell of any of paragraphs 32-53, wherein the cell expresses human telomerase reverse transcriptase or an antigenic fragment or variant thereof.
55. The dendritic cell of paragraph 54, wherein the antigen comprises a fusion protein comprising a proteasomal target sequence of IκBα and a fragment of human telomerase reverse transcriptase.
56. The dendritic cell of paragraph 55, wherein the fusion protein comprises SEQ ID NO:13.
57. The dendritic cell of any of paragraphs 32-56, wherein the cell presents the cancer antigen in an HLA-restricted manner.
58. The dendritic cell of any of paragraphs 32-57, wherein the antigen is introduced by viral transduction.
59. The dendritic cell of any of paragraphs 32-58, wherein the virus is a lentivirus.
60. The dendritic cell of any of paragraphs 32-59, wherein the dendritic cell is capable of priming naïve PBMCs to generate cytotoxic lymphocytes that recognize antigen.
61. The dendritic cell of any of paragraphs 32-60, wherein the dendritic cell is capable of priming naïve PBMCs to generate cytotoxic lymphocytes capable of killing cells in a non-HLA restricted manner.
62. A method of generating an engineered primary blood dendritic cell, comprising:
  i) providing a sample of cells comprising immature dendritic cells such as PBMCs;
  ii) treating the cells in culture with an effective amount of phytohaemagglutinin (PHA);
  iii) treating the cells in culture with an effective amount of IL-2;
  iv) expressing a functional Tax protein from a T cell leukemia virus in the cells and culturing the cells; and
  v) depleting T cells from the cultured cells.
63. The method of paragraph 62, wherein the PBMCs are isolated from a leukopak.
64. The method of any of paragraphs 62-63, wherein the concentration of PHA ranges from about 1-5 μg/ml.
65. The method of any of paragraphs 62-64, wherein the concentration of PHA is about 5 μg/ml.
66. The method of any of paragraphs 62-65, wherein the cells are treated for PHA from about 12 hours to about 36 hours.
67. The method of any of paragraphs 62-66, wherein the cells are treated for PHA from about 24 hours.
68. The method of any of paragraphs 62-67, wherein the cells were treated with IL-2 after treatment with PHA.
69. The method of any of paragraphs 62-68, wherein the cells were treated with IL-2 after treatment with PHA.
70. The method of any of paragraphs 62-69, wherein the cells were treated with about 100-200 units/ml of IL-2 and cultured for a period of time in media comprising IL-2.
71. The method of any of paragraphs 62-70, wherein the cells are cultured for a period of time ranging from about 2-10 days in media comprising IL-2.
72. The method of any of paragraphs 62-71, wherein the cells are cultured for a period of time from about 4-5 days in media comprising about 100-200 units/ml IL-2.
73. The method of any of paragraphs 71-72, wherein the cells are manipulated to express a functional Tax protein following step iii).
74. The method of paragraph 73, wherein the cells are transduced with a virus that encodes a functional Tax protein from a T cell leukemia virus.
75. The method of paragraph 74, wherein the Tax protein is from a human T cell leukemia virus selected from the group consisting of HTLV-1, HTLV-2, and HTLV-3.
76. The method of paragraph 75, wherein the Tax protein is from HTLV-2.
77. The method of any of paragraphs 74-76, wherein the virus is a lentivirus.
78. The method of any of paragraphs 74-77, wherein the cells are transduced in the presence of about 10 μg/ml polybrene.
79. The method of any of paragraphs 73-78, wherein the transduced cells are further cultured in media comprising about 100 units/ml of IL-2.
80. The method of paragraph 73-79, wherein the transduced cells are further cultured in media comprising IL-2 for about 2-3 months.
81. The method of any of paragraphs 73-78, wherein the transduced cells are cultured in media comprising human serum and IL-2.
82. The method of paragraph 81, wherein the transduced cells are cultured for about 2-3 months in media comprising human serum.
83. The method of paragraph 82, wherein the cells are cultured in media comprising 5% heat-inactivated human AB serum.
84. The method of any of paragraphs 70-80 wherein the media comprises complete RPMI1640 medium comprising 10% fetal bovine serum.
85. The method of any of paragraphs 81-83, wherein the media comprises complete RPMI1640 medium.
86. The method of any of paragraphs 62-85, wherein the T cells are depleted with a composition comprising a molecule that binds to T cells.
87. The method of paragraph 86, wherein the T cells are depleted with an antibody.
88. The method of paragraph 87, wherein the antibody is an anti-CD3 antibody.
89. The method of any of paragraphs 87-88, wherein the antibody is conjugated to a magnetic bead.
90. The method of any of paragraphs 62-89, wherein the dendritic cell has a constitutive maturation and activation phenotype.
91. The method of any of paragraphs 62-90, wherein the dendritic cell is a human cell.
92. The method of any of paragraphs 62-91, wherein the dendritic cell is CD205+.
93. The method of any of paragraphs 62-92, wherein the dendritic cell is CD11c+.
94. The method of any of paragraphs 62-93, wherein the dendritic cell expresses one or more dendritic cell maturation and activation markers.
95. The method of paragraph 94, wherein the dendritic cell maturation and activation markers are selected from the group consisting of CD83, CD80, CD86, CD70, CCR7 and HLA-DR.
96. The method of any of paragraphs 62-95, wherein the dendritic cells are capable of growth in suspension culture.
97. The method of any of paragraphs 62-96, wherein the dendritic cell is TLR3+ and TLR4−.

98. The method of any of paragraphs 62-97, wherein the dendritic cell expresses the cleaved form of TLR7.

99. The method of any of paragraphs 62-98, wherein the dendritic cell expresses TLR9.

100. The method of any of paragraphs 62-99, wherein the dendritic cell produces IL-1A and TNFα.

101. The method of any of paragraphs 62-100, wherein the dendritic cell produces IL-15.

102. The method of any of paragraphs 62-101, wherein the dendritic cell produces negligible levels of IL-10 and TGFβ.

103. The method of any of paragraphs 62-102, wherein the dendritic cell expresses c-Myc.

104. The method of any of paragraphs 62-103, wherein the transcription factors NF-κB, Stat3 and AP-1 are active.

105. The method of any of paragraphs 62-104, wherein the dendritic cell is capable of inducing proliferation of naïve lymphocytes in the absence of exogenously added IL-2.

106. The method of any of paragraphs 62-105, wherein the dendritic cell has been genetically modified to express one or more HLA proteins.

107. The method of any of paragraphs 62-106, wherein the dendritic cell has been genetically modified to express HLA-A2.1.

108. The method of any of paragraphs 62-107, wherein the dendritic cell presents one or more antigens or antigenic fragments or variants thereof.

109. The method of any of paragraphs 62-108, wherein the antigen is a cancer antigen.

110. The method of any of paragraphs 62-109, wherein the cell expresses human telomerase reverse transcriptase or an antigenic fragment or variant thereof.

111. The method of paragraph 110, wherein the cancer antigen comprises a fusion protein comprising a proteasomal target sequence of IκBβ and a fragment of human telomerase reverse transcriptase.

112. The method of paragraph 111, wherein the fusion protein comprises SEQ ID NO:13.

113. The method of any of paragraphs 62-112, wherein the cell presents the cancer antigen in an HLA-restricted manner.

114. The method of any of paragraphs 62-113, wherein the cancer antigen is introduced by viral transduction.

115. The method of paragraph 114, wherein the virus is a lentivirus.

116. The method of any of paragraphs 62-115, wherein the dendritic cell is capable of priming naïve PBMCs to generate cytotoxic lymphocytes that recognize antigen.

117. A method of generating monocyte-derived dendritic cells, comprising: providing a sample of cells comprising immature dendritic cells derived from monocytes; and expressing a functional Tax protein from a T cell leukemia virus in the cells.

118. A method of generating monocyte-derived dendritic cells, comprising:
i) providing adherent monocyte cells;
ii) culturing the cells in media comprising an effective amount of GM-CSF and IL-4;
iii) expressing a functional Tax protein from a T cell leukemia virus in the cells;
iv) culturing the functional Tax protein expressing cells in media comprising an effective amount of GM-CSF and IL-4.

119. The method of paragraph 118, wherein following step iv), the method further comprises culturing the cells in media comprising IL-2.

120. The method of any of paragraphs 117-119, wherein IL-4 and/or GM-CSF is fused to Fc4.

121. The method of any of paragraphs 117-120, wherein the adherent monocytes come from about 4 million PBMCs.

122. The method of any of paragraphs 117-121, wherein the culturing of part ii) comprises culturing the cells in media comprising conditioned medium from GM-CSF-Fc4/IL-4-Fc4 producing 293 cells.

123. The method of paragraph 122, wherein the cells are cultured in media comprising the conditioned medium at about a 1:10 dilution for about 7 days.

124. The method of paragraph 117-123, wherein the cells are transduced with a virus that encodes a functional Tax protein from a T cell leukemia virus.

125. The method of paragraph 124, wherein the Tax protein is from a human T cell leukemia virus selected from the group consisting of HTLV-1, HTLV-2, and HTLV-3.

126. The method of paragraph 124, wherein the Tax protein is from HTLV-2.

127. The method of any of paragraphs 123-126, wherein the virus is a lentivirus.

128. The method of any of paragraphs 123-127, wherein the cell is transduced in the presence of about 10 μg/ml polybrene.

129. The method of any of paragraphs 117-128, wherein the media comprises RPMI1640 medium with about 10% fetal bovine serum.

130. The method of any of paragraphs 117-129, wherein the culturing step iv) comprises culturing the Tax protein expressing cells in RPMI1640 medium with 10% FBS in the presence of GM-CSF-Fc4 and IL-4-Fc4 for about 5-7 days, followed by maintaining the cells in culture in the presence of about 100 units/ml of IL-2.

131. The method of any of paragraphs 117-130, further comprising activating the monocyte-derived dendritic cells.

132. The method of paragraph 131, wherein the activating comprises stimulating the cells with TNFα and LPS.

133. The method of paragraph 132, wherein the TNFα is administered in an amount of from about 10-250 ng/ml and LPS is administered in an amount of from about 1-5 μg/ml.

134. The method of any of paragraphs 131-133, wherein the cells are stimulated for 1-5 days.

135. The method of paragraph 134, wherein the cells are stimulated for about 2 days.

136. The method of any of paragraphs 117-135, wherein the Tax protein is from a human T cell leukemia virus selected from the group consisting of HTLV-1, HTLV-2, HTLV-3 and HTLV-4.

137. The method of any of paragraphs 117-136, wherein the Tax protein is from HTLV-2.

138. The method of any of paragraphs 117-137, wherein the dendritic cell has a constitutive maturation and activation phenotype.

139. The method of any of paragraphs 117-138, wherein the dendritic cell is a human cell.

140. The method of any of paragraphs 117-139, wherein the dendritic cell is CD205+.

141. The method of any of paragraphs 117-140, wherein the dendritic cell expresses one or more dendritic cell maturation and activation markers.

142. The method of paragraph 117-141, wherein the dendritic cell maturation and activation markers are selected from the group consisting of CD83, CD80, CD86, CD70.

143. The method of paragraph 142, wherein the dendritic cell further expresses 4-1BBL and/or CD4.

144. The method of any of paragraphs 117-143, wherein the dendritic cells are capable of growth in suspension culture.
145. The method of any of paragraphs 117-144, wherein the dendritic cells are capable of proliferating for up to three months in culture.
146. The method of any of paragraphs 117-145, wherein the dendritic cell is TLR3+ and TLR4−.
147. The method of any of paragraphs 117-146, wherein the dendritic cell expresses the cleaved form of TLR7.
148. The method of any of paragraphs 117-147, wherein the dendritic cell produces IL-1A and TNFα.
149. The method of any of paragraphs 117-148, wherein the dendritic cell produces TGFβ.
150. The method of any of paragraphs 117-149, wherein the dendritic cell produces IL-15.
151. The method of any of paragraphs 117-150, wherein the dendritic cell expresses c-Myc.
152. The method of any of paragraphs 117-151, wherein the dendritic cell is capable of inducing proliferation of naïve lymphocytes in the absence of exogenously added IL-2.
153. The method of any of paragraphs 117-152, wherein the dendritic cell has been genetically modified to express one or more HLA proteins.
154. The method of any of paragraphs 117-153, wherein the dendritic cell has been genetically modified to express HLA-A2.1.
155. The method of any of paragraphs 117-154, wherein the dendritic cell expresses one or more antigens or antigenic fragments or variants thereof.
156. The method of any of paragraphs 117-155, wherein the antigen is a cancer antigen.
157. The method of any of paragraphs 117-156, wherein the dendritic cell expresses human telomerase reverse transcriptase or an antigenic fragment or variant thereof.
158. The method of paragraph 157, wherein the cancer antigen comprises a fusion protein comprising a proteasomal target sequence of IκBα and a fragment of human telomerase reverse transcriptase.
159. The method of paragraph 158, wherein the fusion protein comprises SEQ ID NO:13.
160. The method of any of paragraphs 154-159, wherein the cells present the antigen in an HLA-restricted manner.
161. The method of any of paragraphs 154-160, wherein the antigen is introduced by viral transduction.
162. The method of paragraph 161, wherein the virus is a lentivirus.
163. The method of any of paragraphs 117-162, wherein the dendritic cell is capable of priming naïve PBMCs to generate cytotoxic lymphocytes that recognize antigen.
164. A dendritic cell made according to the methods of any of paragraphs 62-163.
165. A method for producing cytotoxic T lymphocytes, comprising
    culturing dendritic cells of any of paragraphs 1-61 together with cells comprising naïve lymphocytes for a period of time, whereby cytotoxic T lymphocytes are produced.
166. A method for producing cytotoxic T lymphocytes, comprising
    i) culturing dendritic cells of any of paragraphs 1-61 together with cells comprising naïve lymphocytes for a first period of time to create a mixed culture of cells; and
    ii) treating the mixed culture of cells with an effective amount of IL-2 and continuing to culture the cells for a second period of time,
    whereby cytotoxic T lymphocytes are produced.
167. The method of any of paragraphs 165-166, wherein the cells comprising naïve lymphocytes comprise naïve PBMCs.
168. The method of any of paragraphs 165-167, wherein the naïve lymphocytes are isolated from leukopaks.
169. The method of any of paragraphs 165-168, wherein the naïve lymphocytes and the dendritic cells are allogenic.
170. The method of any of paragraphs 165-169, wherein the ratio of dendritic cells to naïve PBMCs is about 1:100.
171. The method of any of paragraphs 166-170, wherein the culturing of step i) is conducted without addition of exogenous cytokines.
172. The method of any of paragraphs 166-172, wherein the first period of time is about 2-3 days.
173. The method of any of paragraphs 166-172, wherein the concentration of the IL-2 is about 100-200 units/ml.
174. The method of any of paragraphs 166-173, wherein the second period of time is from 2-6 weeks.
175. The method of any of paragraphs 166-174, wherein the cytotoxic T lymphocytes are antigen specific and induce cytolysis of target cells in an HLA-restricted manner.
176. The method of any of paragraphs 166-175, wherein the cytotoxic T lymphocytes comprise CD3+/CD56+ T cells capable of killing target cells in a non-HLA-restricted manner.
177. The method of any of paragraphs 166-176, wherein the dendritic cells express 4-1BBL.
178. The method of any of paragraphs 166-177, wherein the dendritic cells have been engineered to express 4-1BBL.
179. The method of any of paragraphs 176-178, wherein the non-HLA-restricted killing of cells is mediated by ligand binding of NKG2D.
180. A pharmaceutical composition, comprising an effective amount of cytotoxic T lymphocytes, produced according to the method of any of paragraphs 165-179.
181. A method of treating a disease or condition in a subject, comprising administering to the subject an effective amount of cytotoxic T lymphocytes, wherein the cytotoxic T lymphocytes are produced using a dendritic cell of any of paragraphs 1-61.
182. A method of treating a disease or condition in a subject, comprising administering to the subject an effective amount of cytotoxic T lymphocytes, wherein the cytotoxic T lymphocytes are produced by a method of any one of paragraphs 165-179.
183. A method of treating a disease or condition in a subject, comprising administering to the subject an effective amount of a dendritic cell of any of paragraphs 1-61.
184. The method of any of paragraphs 181-183, wherein the disease is cancer.
185. The method of paragraph 184, wherein the cancer cells express MICA/B.
186. The method of any of paragraphs 181-185, wherein the cancer is breast cancer.
187. The method of any of paragraphs 181-186, wherein the subject is a mammal.
188. The method of any of paragraphs 181-187, wherein the subject is a human.
189. A method of generating an engineered primary blood dendritic cell, comprising:
    i) providing a sample of cells comprising immature dendritic cells; and
    ii) expressing a functional Tax protein from a T cell leukemia virus in the cells.
190. A method of generating an engineered primary blood dendritic cell, comprising:

i) providing a sample of cells comprising dendritic precursor cells;
ii) expressing a functional Tax protein from a T cell leukemia virus in the cells and culturing the cells;
iii) culturing the cells to induce their differentiation into dendritic cells; and
iv) depleting T cells from the cultured cells.

191. A method of generating monocyte-derived dendritic cells, comprising:
i) providing adherent monocyte cells;
ii) expressing a functional Tax protein from a T cell leukemia virus in the cells; and
iii) culturing the cells to induce their differentiation into dendritic cells.

Application of the teachings of the present invention to a specific problem is within the capabilities of one having ordinary skill in the art in light of the teaching contained herein. Examples of the compositions and methods of the invention appear in the following non-limiting Example.

EXAMPLES

Figure 1B:
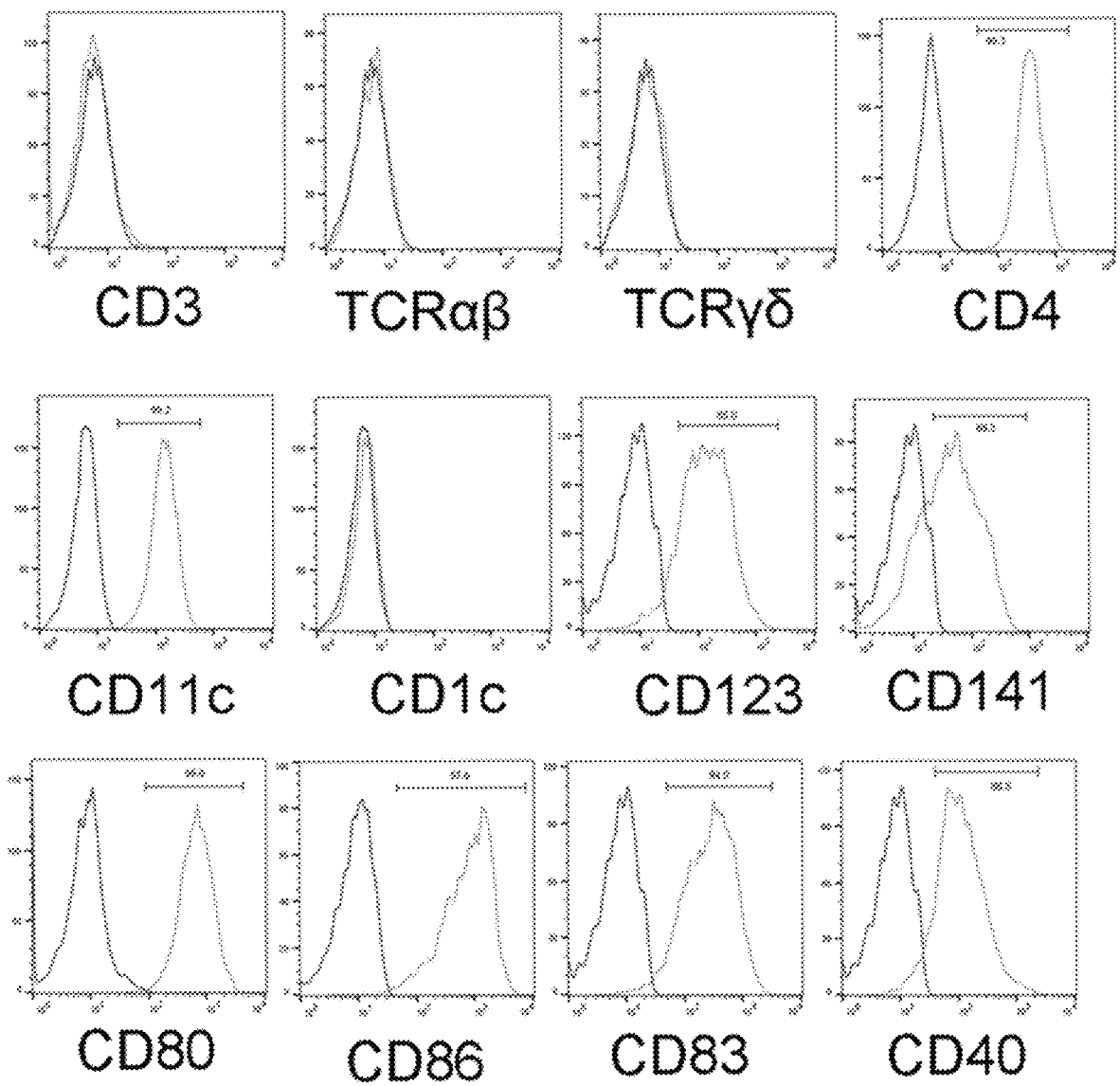
Figure 1B:
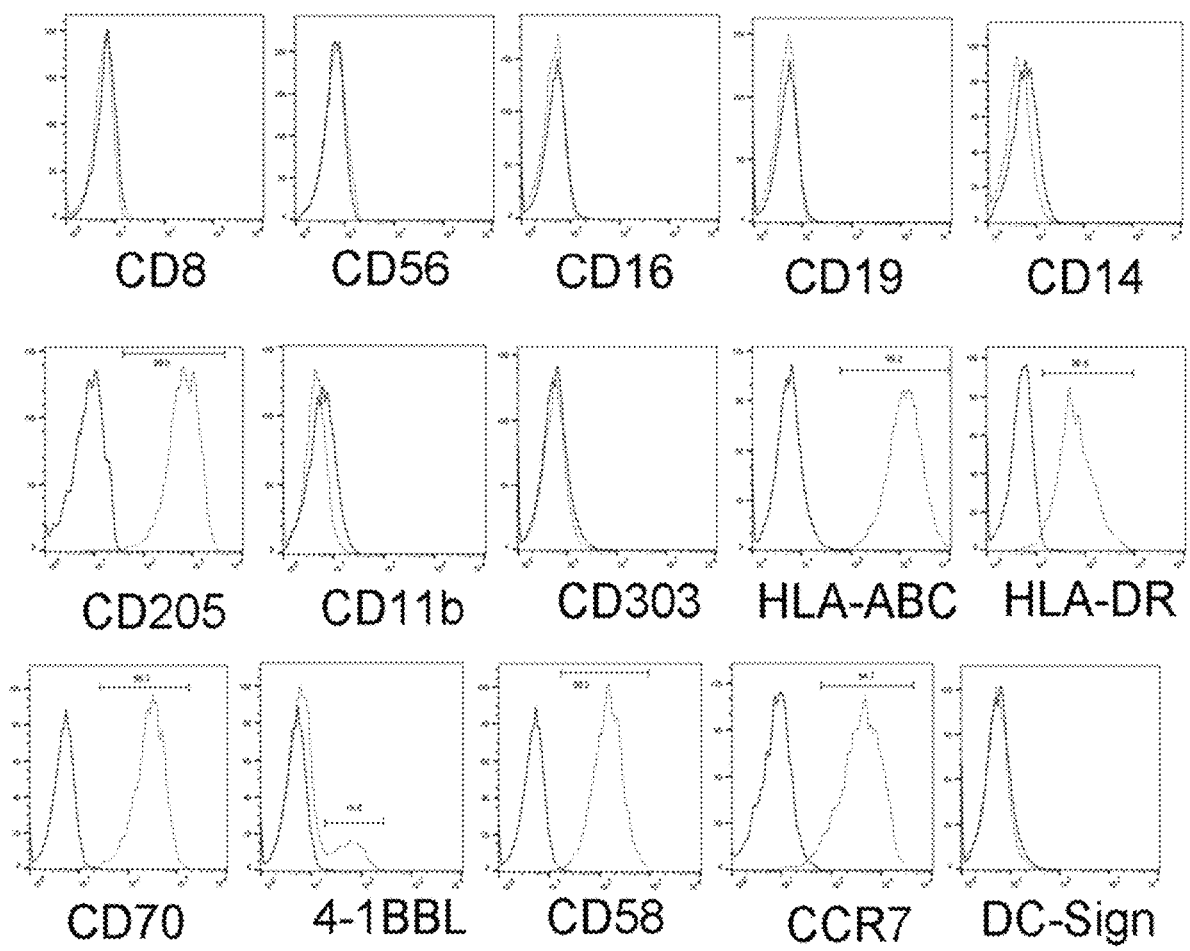

Example 1. Development of Human Primary Blood and Monocyte-Derived Dendritic Cell Lines HTLV-2 Tax was exploited as a molecular tool for its role in modulating DC function. To prevent potential loss of DCs during culture of the Tax-transduced PBMCs, the transduced cells were negatively selected using anti-CD3 magnetic beads to deplete T cells. Two CD3-negative Tax-GFP+ cell lines from the transduced PBMCs of ten blood donors were evolved and grew continuously over six months without losing growth potential. These two DC cell lines, which were established from two different blood donors, displayed dendritic cell-related markers. These cells were lineage-negative and expressed CD11c and CD205 as well as DC maturation and activation molecules including CD83, CD80, CD86, CD70, CCR7 and HLA-DR (FIGS. 1a and 1b). These two cell lines were named as ihv-DC1 and ihv-DC2, which represented a subset of human CD11c+/CD205+ blood dendritic cells that maintained a constitutive maturation and activation phenotype.

Figure 1C:
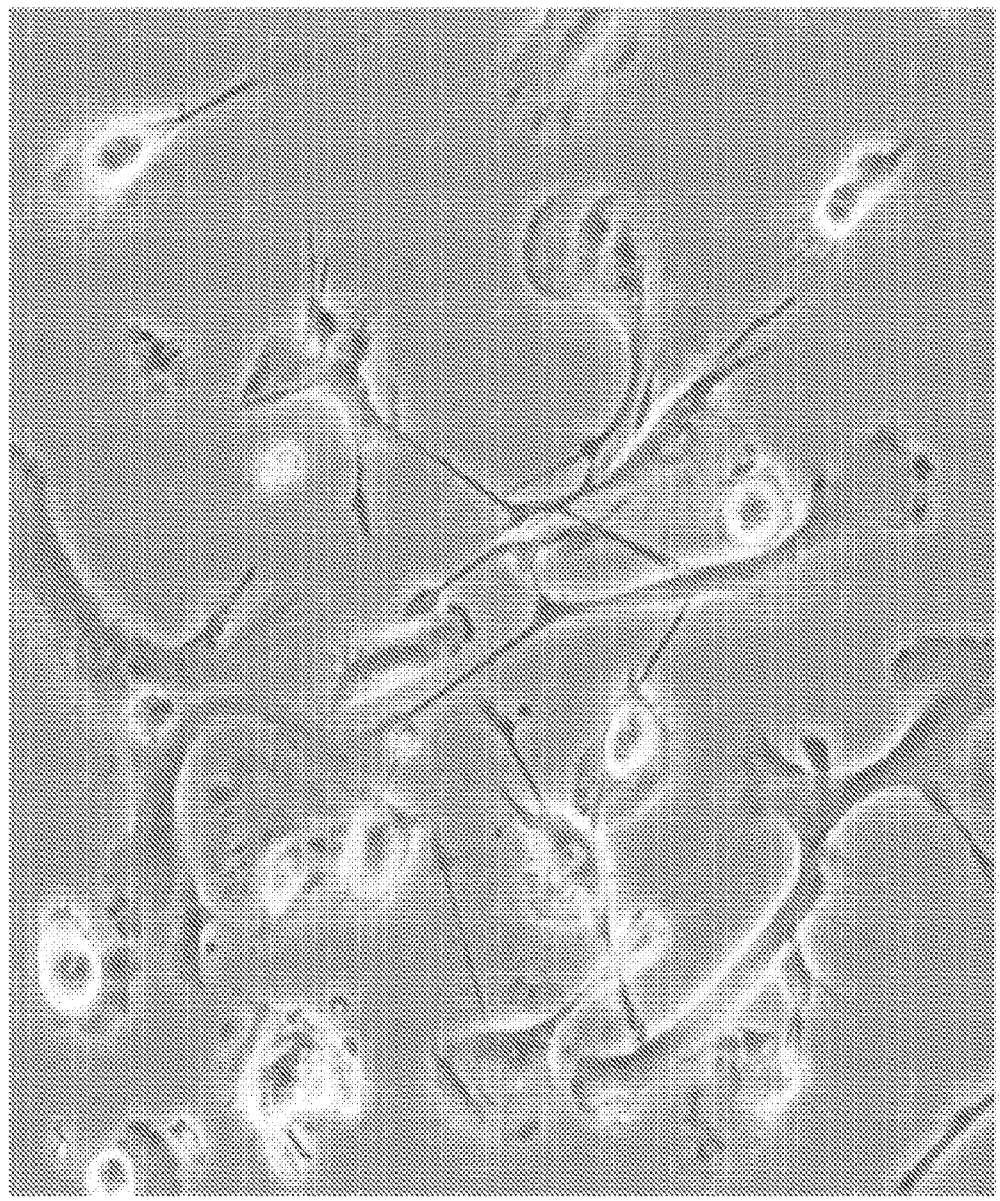
Figure 1D:
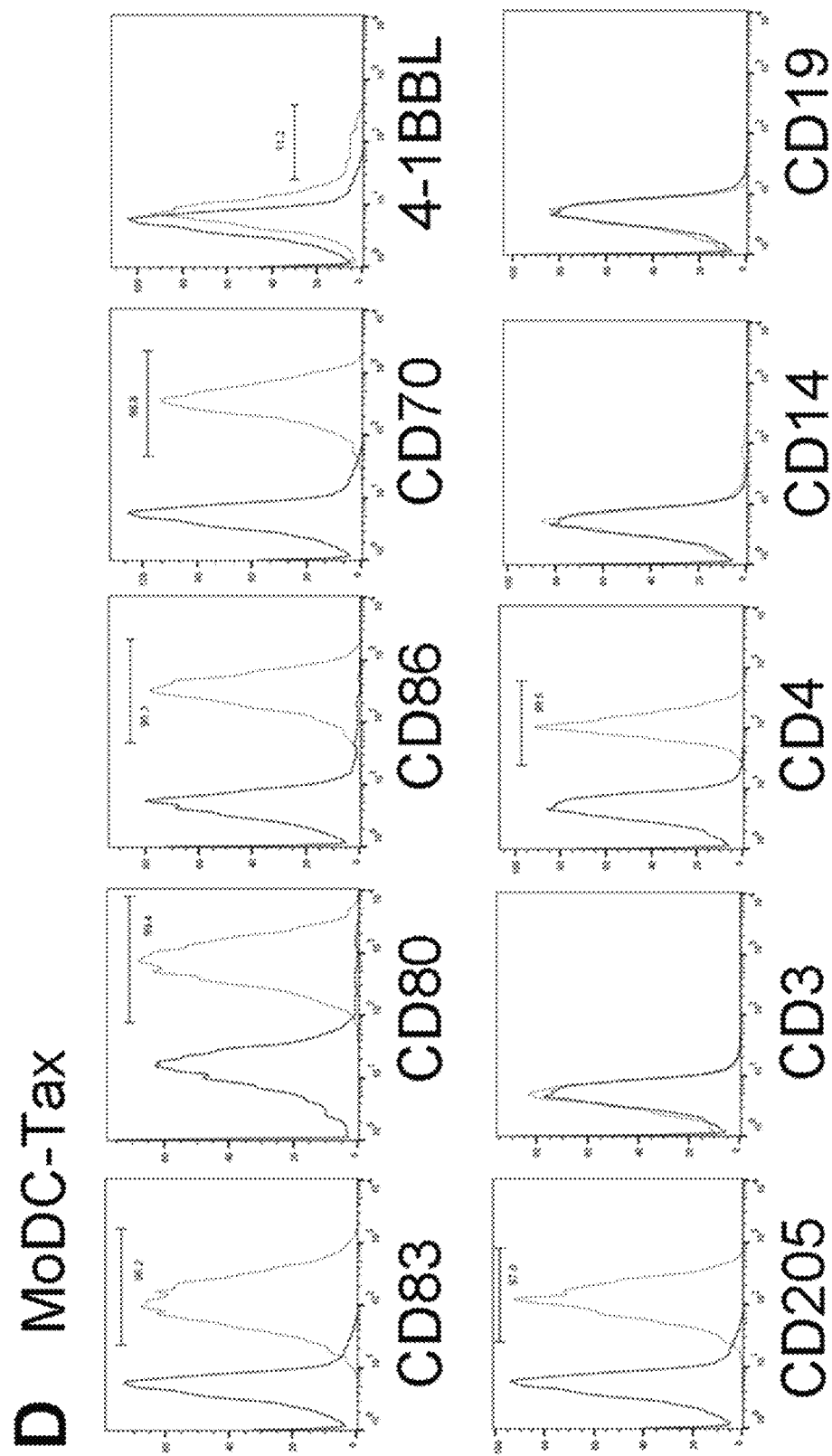

The ihv-DCs grew in suspension at the normal culture condition, and a few cells were adherent and showed typical dendrites. To validate the ability of Tax in promoting DC growth, adherent monocytes from PBMCs were first simulated with GM-CSF/IL-4 to generate monocyte-derived dendritic cells (MoDCs) (FIG. 1c). Some of these MoDCs presented dendrites, and the MoDCs were subsequently transduced with the Tax lentivirus. The transduced MoDC-Tax cells were detached during culture and were capable of proliferating for up to three months. The MoDC-Tax cells presented a mature and activation phenotype (FIG. 1d). These results suggested that Tax was able to promote the growth of both blood and monocyte-derived DCs that lost cell adherence at the normal culture condition.

Results

Expression of TLRs, Cytokines and Cellular Signaling Molecules in Ihv-DCs

Figure 2A:
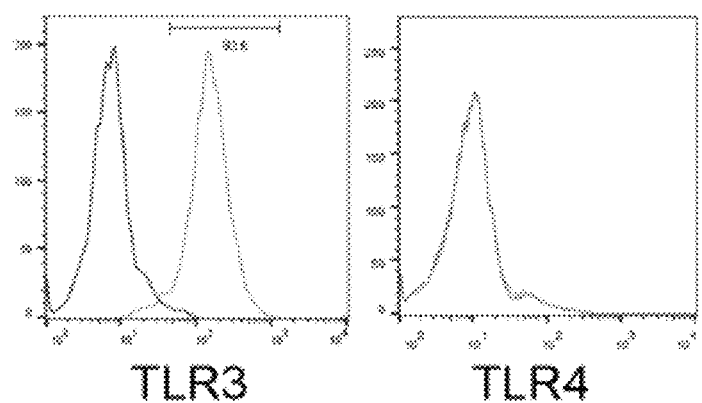
FIG. 2. The expression profiles of TLRs, cytokines and cellular signaling molecules in ihv-DCs. (a) The expression of TLR3 and TLR4 in ihv-DCs and MoDC-Tax cells examined by FACS. (b) Immunoblot analysis of TLR1, TLR2, TLR7 and TLR9 in the established DCs using relevant antibodies. Cytokine expression profiles were determined by qRT-PCR in ihv-DC1 cells (c), ihv-DC2 cells (d), MoDC-Tax cells (e) and TNFα/LPS-activated MoDCs (f). (g) The expression levels of c-Myc in various DCs were determined by qRT-PCR. (h) Immunoblot analysis of the expressions of Tax-GFP, Bcl-2, Bcl-xL and Mcl-1 in the established DCs. PBLs (peripheral blood lymphocytes from normal donors) and MT4 were used for controls. (i) The phosphorylation status of Stat1, Stat3, Stat5, pRb or cdc2 was examined using specific anti-phospho-specific antibodies. (j) EMSA assay for detection of the transcriptional activities of NF-κB, Stat3 and AP-1 using the nuclear extracts prepared from ihv-DCs.
Figure 2A:
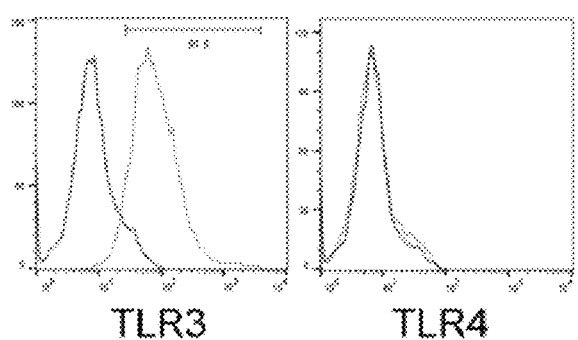
Figure 2A:
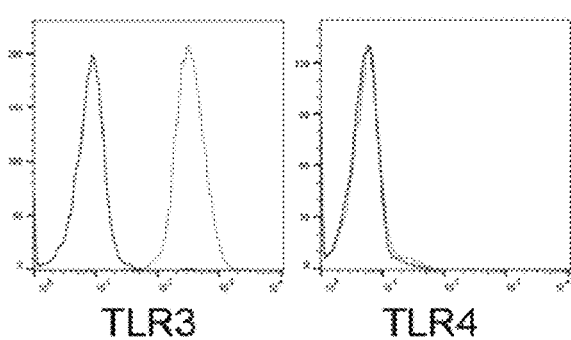
Figure 2B:
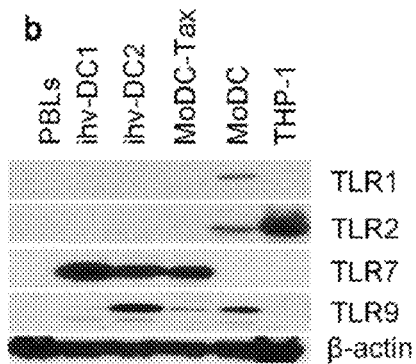
Figure 2C:
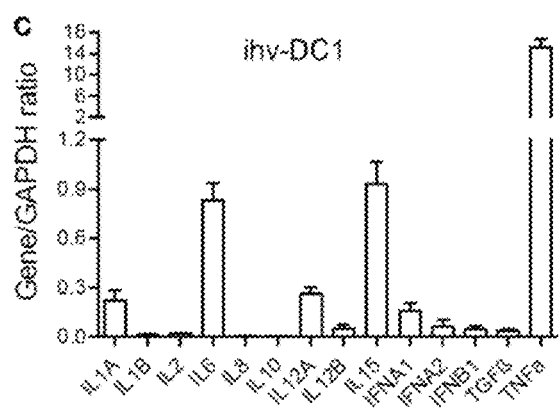
Figure 2D:
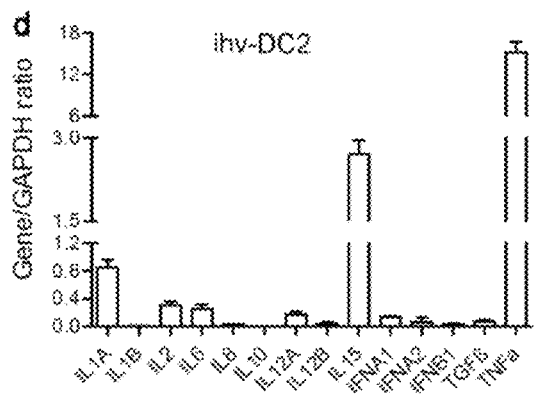
Figure 2E:
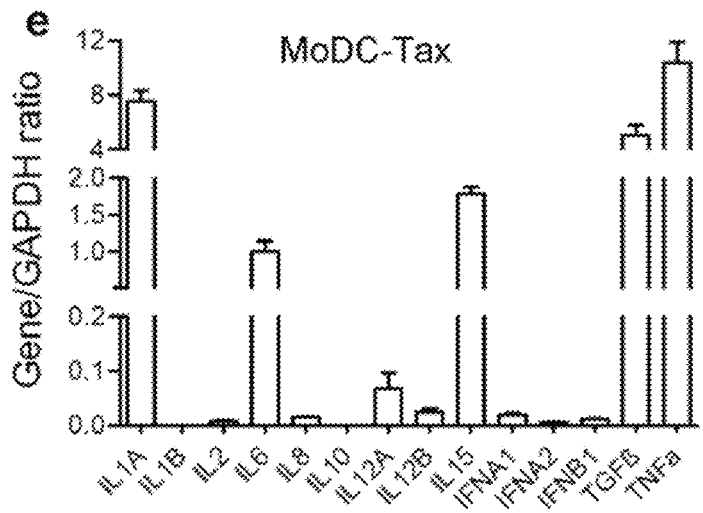
Figure 2F:
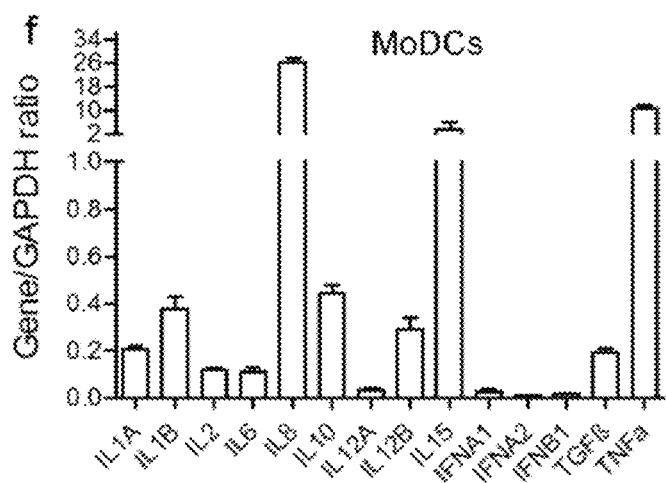

The intracellular dsRNA-sensing TLR3 receptor was expressed while TLR4 was negative in both ihv-DCs and MoDC-Tax cells (FIG. 2a). The cleaved form of TLR7 was detected in both ihv-DCs and MoDC-Tax, but not in MoDCs (FIG. 2b), suggesting that Tax upregulated TLR7 in DCs. TLR9 was expressed highly in ihv-DC2, and slightly in MoDCs (FIG. 2b). Regardless of the TLR expression status, these receptors were no longer required for inducing DC maturation and activation, since these established DC cell lines persistently expressed high levels of co-stimulatory molecules such as CD80, CD86, CD70 and CD83.

The inflammatory cytokines such as IL-1A and TNFα were produced in all ihv-DCs and MoDCs, while the immune regulatory factors including IL-10 and TGFβ was expressed at a negligible level in ihv-DCs, and the MoDC-Tax cells produced TGFβ (FIG. 2c-2f). IL-15, which favors the development of CD8+ cytotoxic lymphocytes, was produced at high levels in all established DC cell lines and the activated MoDCs (FIG. 2c-2f). Taken these results together, the expression profiles of TLRs and cytokines in ihv-DCs correlated well with the phenotypes of mature and activated blood DCs that were generated by the conventional method.

Figure 2G:
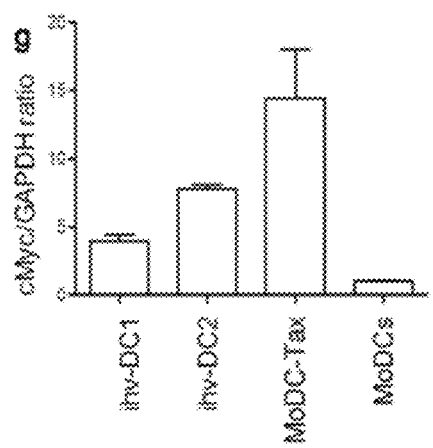
Figure 2H:
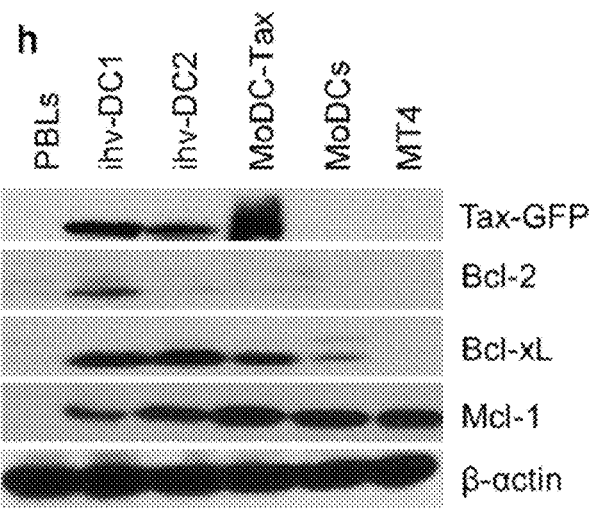
Figure 2I:
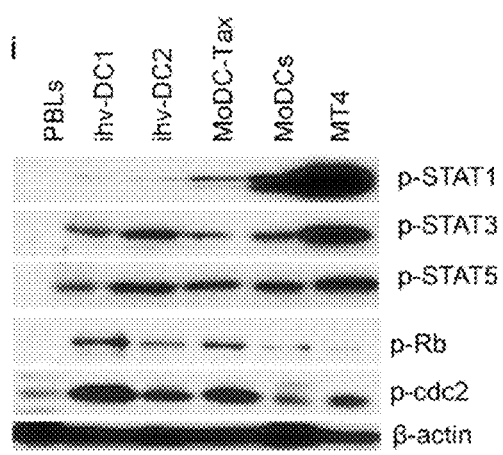
Figure 2J:
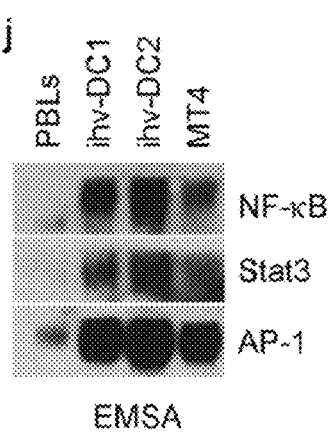

Tax had the capacity to drive cell cycle progression as evidenced by the over-expression of c-Myc in both ihv-DCs and MoDC-Tax cells (FIG. 2g). The pro-survival Bcl-2 protein, Bcl-xL, was notably upregulated only in the DCs that expressed Tax (FIG. 2h). The cell cycle regulators, pRb and cdc2, were phosphorylated in ihv-DCs (FIG. 2i). The phosphorylated forms of Stat1, Stat3 and Stat5 were detected in all DCs (FIG. 2l), and the activities of the transcriptional factors including NF-κB, Stat3 and AP-1 were also observed in ihv-DCs (FIG. 2j). Thus, it appeared that Tax immortalized blood DCs by a similar mechanism to that of Tax-mediated immortalization of CD4+ T cells through oncogenic activation and induction of cell cycle progression.

Induction of Antigen-Specific CTLs by Ihv-DCs

Figure 3A:
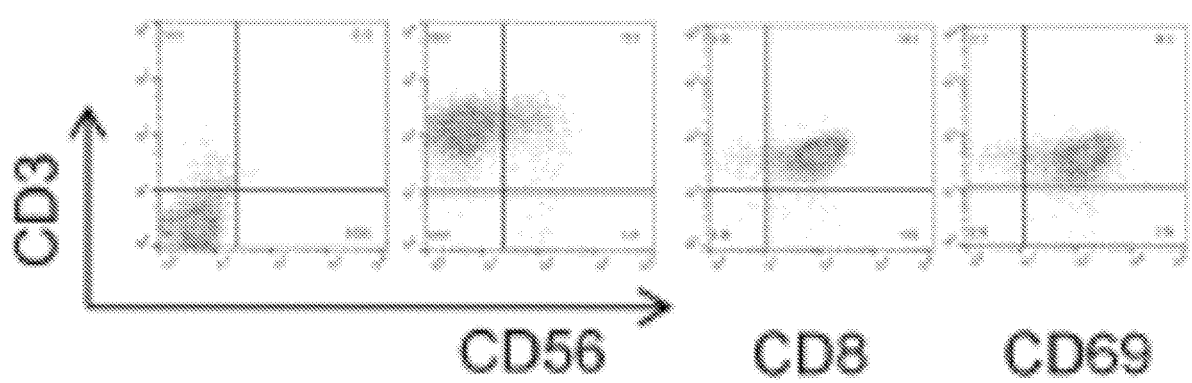
FIG. 3. Induction of antigen-specific CTLs by ihv-DCs. (a) Immunophenotype of ihv-DC2-activated CTLs by two-color FACS analysis. (b) The levels of perforin and granzyme B in ihv-DC-activated CTLs generated from six blood donors were evaluated with immunoblot using relevant antibodies. (c) The cytokine expression profiles of ihv-DC2-activated CTLs by qRT-PCR. (d) MT4L cells (MT4 cells expressing luciferase) are transduced with the HLA-A2.1 lentivirus to generate MT4L-A2.1 cells. The HLA-A2 expression in MT4L and MT4L-A2.1 cells was verified with FACS using anti-HLA-A2-APC. (e) Cell viability assay to determine the cytolysis of the modified MT4 cells by ihv-DC2-activated CTLs. (f) NIH3T3 cells were transduced with the luciferase and HLA-A2 lentiviruses, together with or without the Tax-FLAG lentivirus, to generate 3T3L-A2.1 and 3T3L-A2.1/Tax cells. HLA-A2 staining in 3T3 cells by FACS was shown in the left panel, while the Tax expression was determined by immunofluorescence imaging using anti-FLAG antibody (right panel). Cell viability assay was performed to determine the cytolysis of the 3T3L-A2.1 and 3T3L-A2.1/Tax cells by ihv-DC2-activated CTLs using the luciferase assay (g) and cell imaging analysis (h). **: $p<0.01$ as determined by 2-tail student t-test.
Figure 3B:
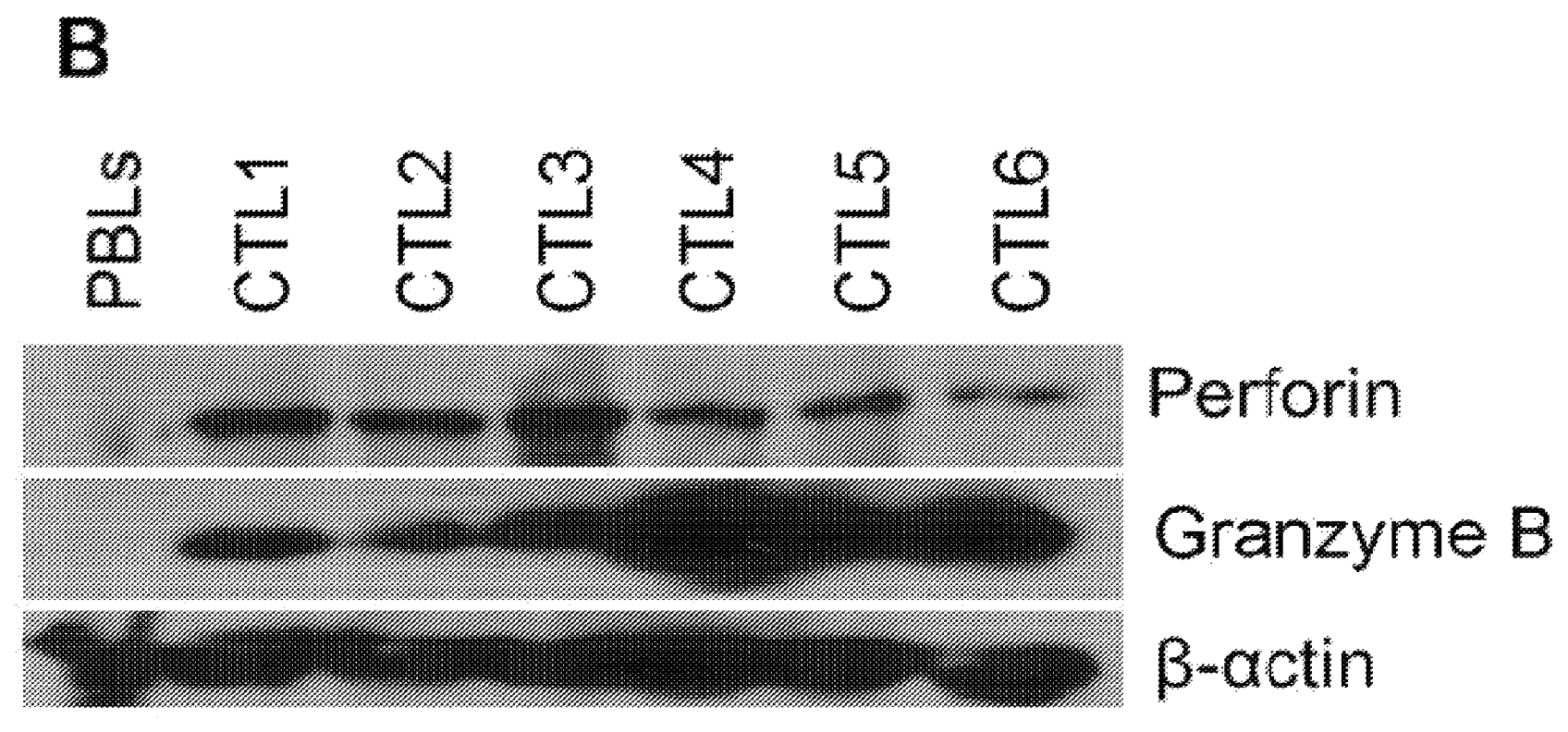
Figure 3C:
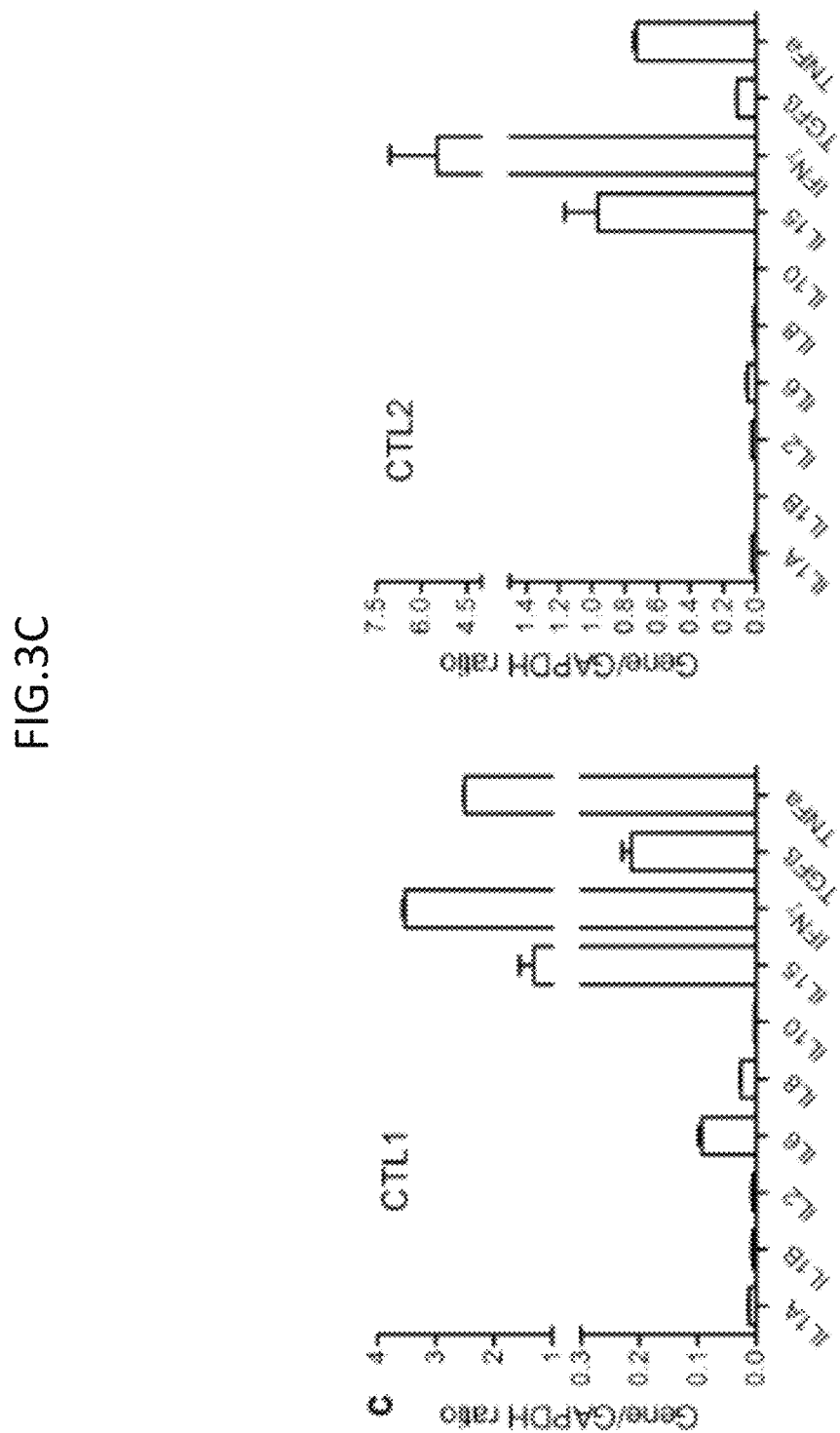
Figure 3D:
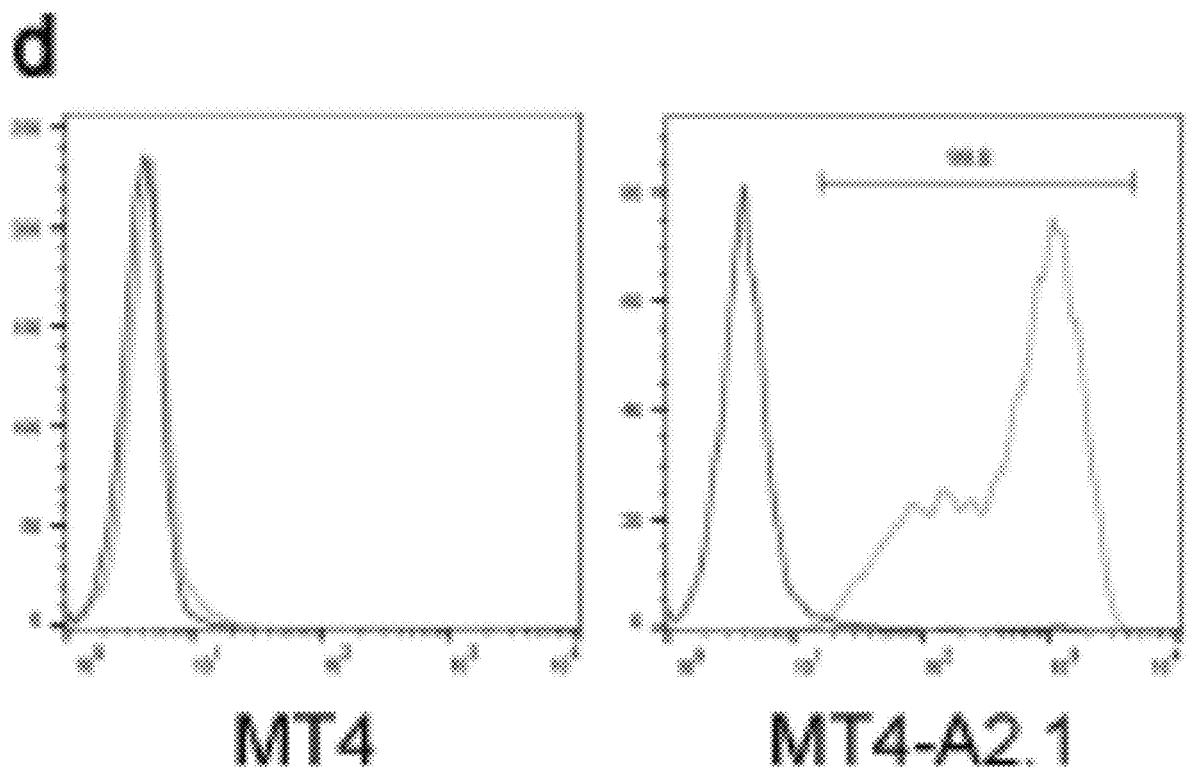
Figure 3E:
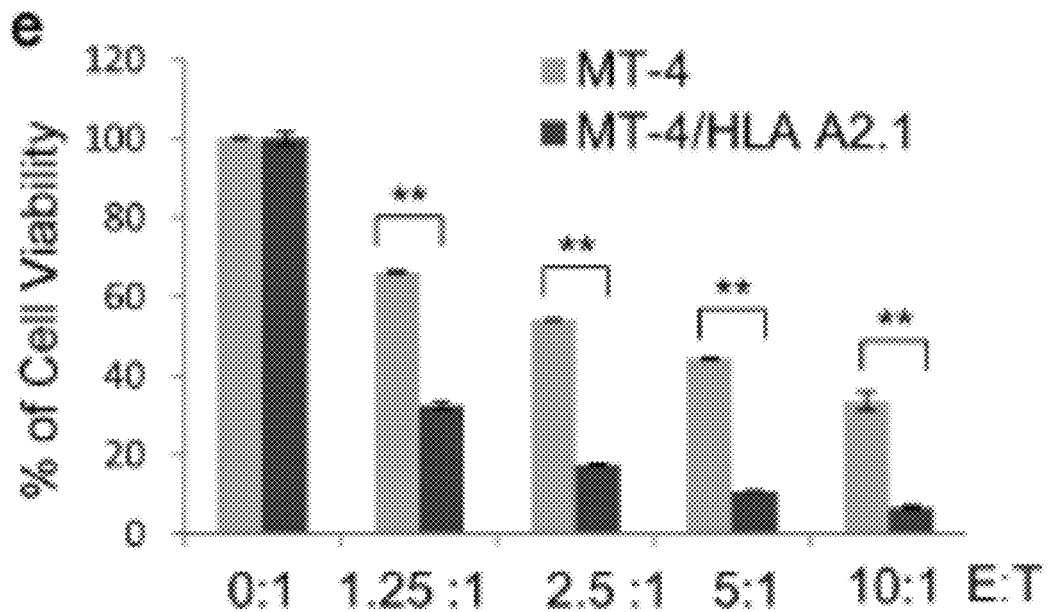
Figure 3F:
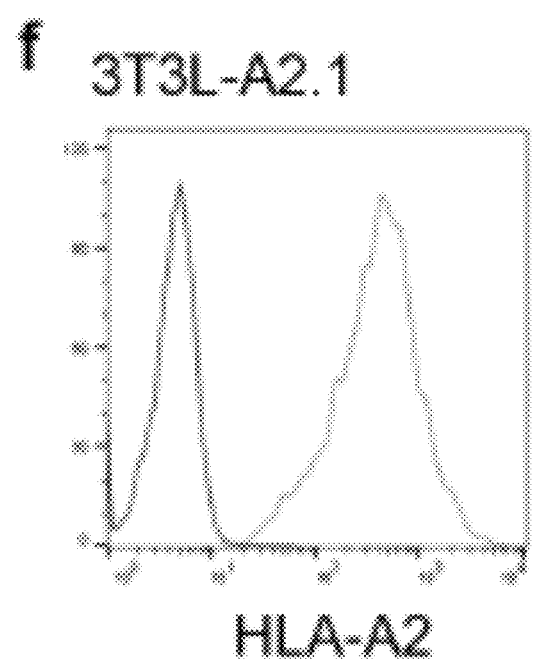
Figure 3G:
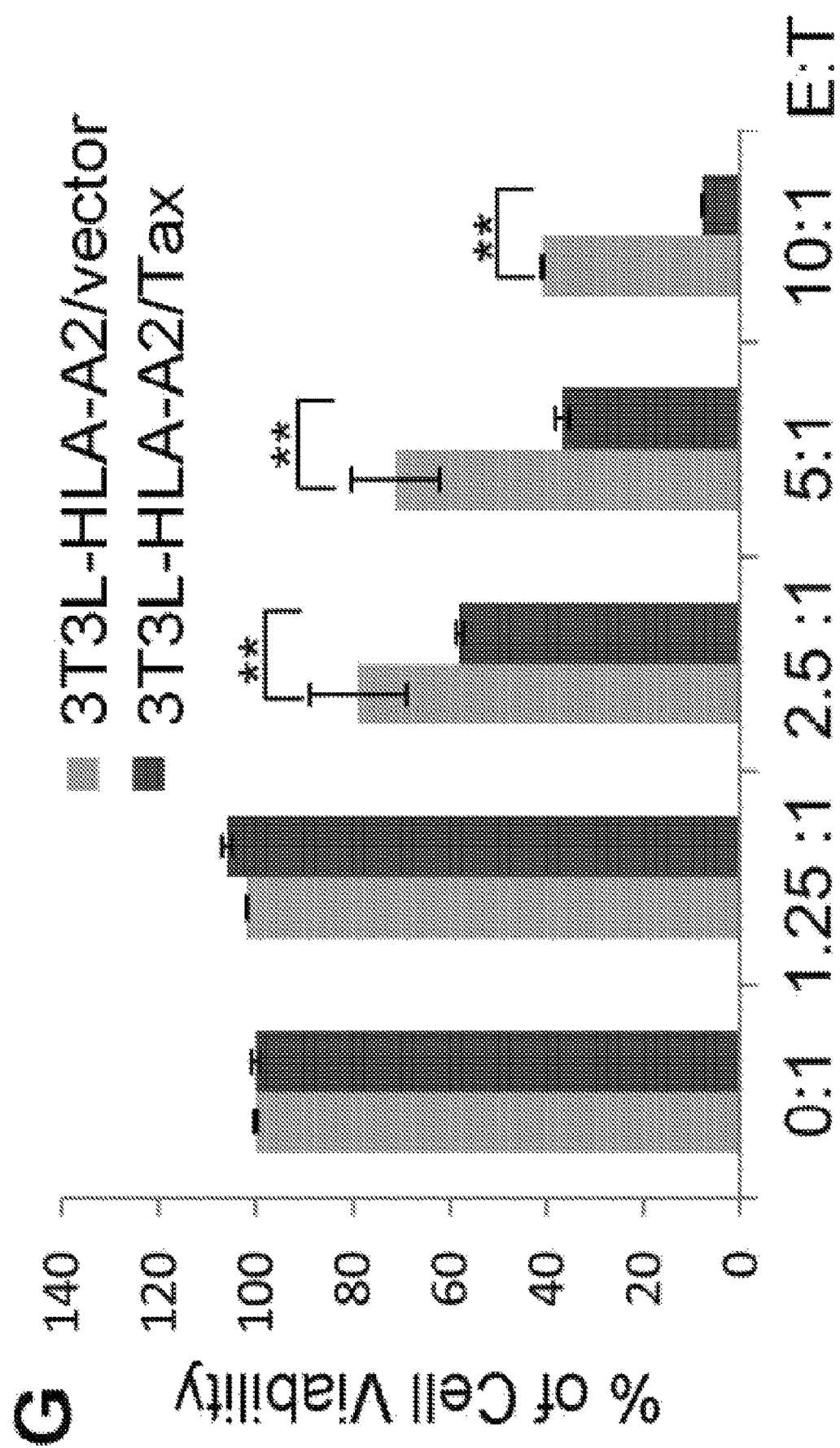
Figure 3H:
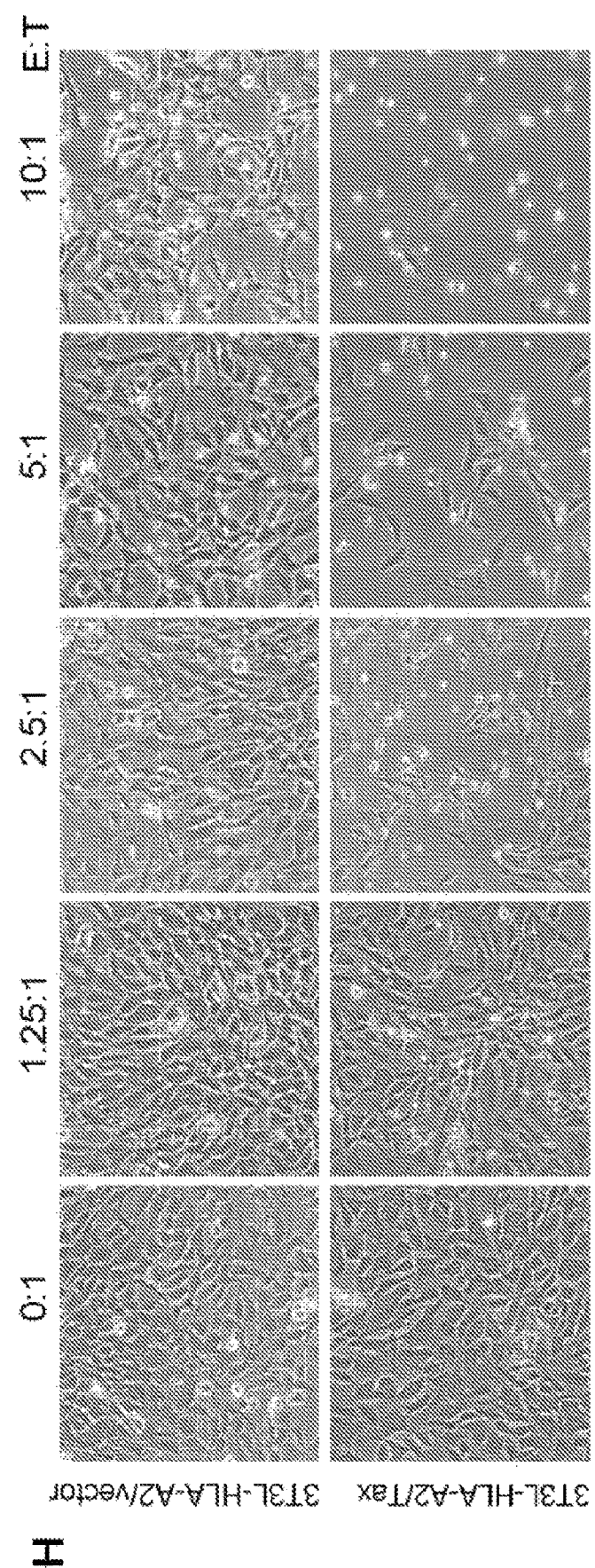

The HLA-A and -B alleles from ihv-DCs were cloned and sequenced. The sequence analysis indicated that ihv-DC1 cells were HLA-A30/B71 while ihv-DC2 cells were HLA-A2.1/B40. Because HLA-A2 is one of the most frequent HLA alleles, it was first determined to test the functionality of ihv-DC2 in induction of cytotoxic lymphocytes. A mixed leukocyte reaction (MLR) assay was set up the by mixing ihv-DC2 cells with naïve PBMCs directly isolated from HLA-A2+ healthy blood donors at the ratio of 1:100. It was observed that ihv-DC2 cells induced drastic expansion of donor lymphocytes in the absence of recombinant IL-2 in the first 2-3 days. The reactive lymphocytes continued to proliferate in the presence of recombinant IL-2 for 4-6 weeks. Two weeks following MLR, the ihv-DC-activated, proliferating lymphocytes generated from PBMCs of various donors displayed a predominant immunophenotype of effector CD8+ T cells, expressed abundant amounts of cytotoxic components, perforin and granzyme B, and produced large amounts of IFNγ and TNFα (FIGS. 3a, 3b and 3c). The ihv-DC cells were completely disappeared as evidenced by lack of the Tax-GFP green fluorescence signal in the MLR culture. The ihv-DC2-activated CTLs were evaluated for their recognition of the Tax antigen. HLA-A2.1 was first expressed into the HLA-A2-negative MT4 cells (Tax+ HTLV-1-transformed T cells) (FIG. 3d). It was found that the ihv-DC2-activated CTLs induced cytolysis of MT4-A2.1 cells more potently than that of MT4 cells (FIG. 3e). A target cell model was next developed using engineered NIH3T3 cells by sequential lentiviral transduction of luciferase, beta-2-microglobulin (B2M) and HLA-A2.1, together with or without Tax-FLAG (FIG. 3f). Tax was mainly localized in the cytoplasmic puncta (FIG. 3f). It was shown that the ihv-DC-activated CTLs induced cytolysis of roughly 90% Tax-expressing, HLA-A2+3T3 cells at the E:T ratio of 10:1 (FIGS. 3g and 3h).

Figure 4A:
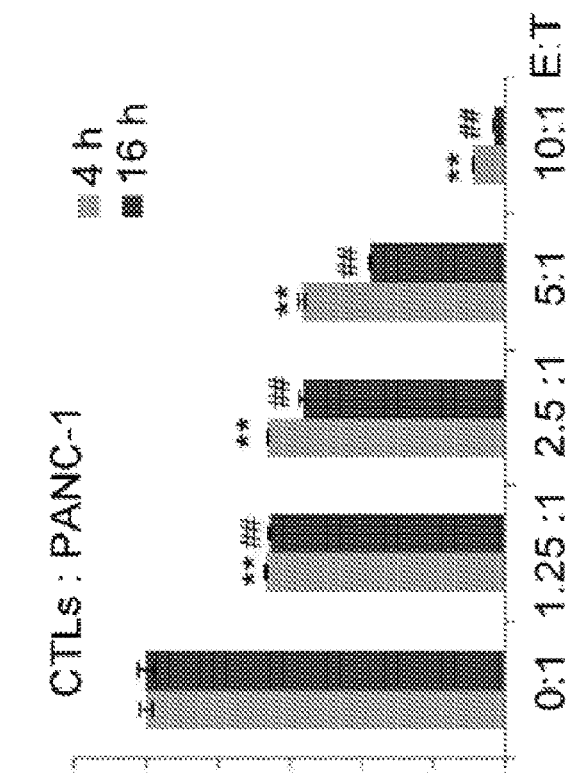
FIG. 4. HLA-restricted cancer killing by ihv-DC2-activated CTLs. Cell viability assay to determine the cytolysis of A375 cells (a), PANC-1 cells (b) and H1299 cells (c) by ihv-DC2-activated CTLs using the luciferase assay and cell imaging analysis (d). (e) FACS analysis of the HLA-A2 expression in A375, PANC-1, H1299 and H1299-HLA-A2.1 cells. H1299-HLA-A2.1 cells were developed by lentiviral transduction of HLA-A2.1 into H1299 cells. Cell viability assay was conducted to determine the cytolysis of H1299/HLA-A2.1 cells by ihv-DC1-activated CTLs using the luciferase assay (f) and cell imaging analysis (g). **: $p<0.01$ as determined by 2-tail student t-test.
Figure 4B:
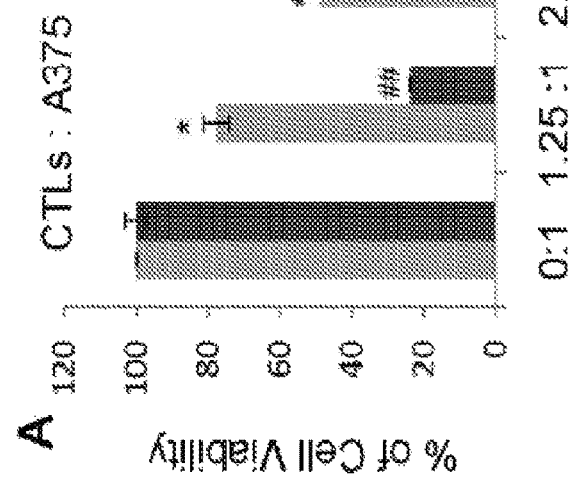
Figure 4C:
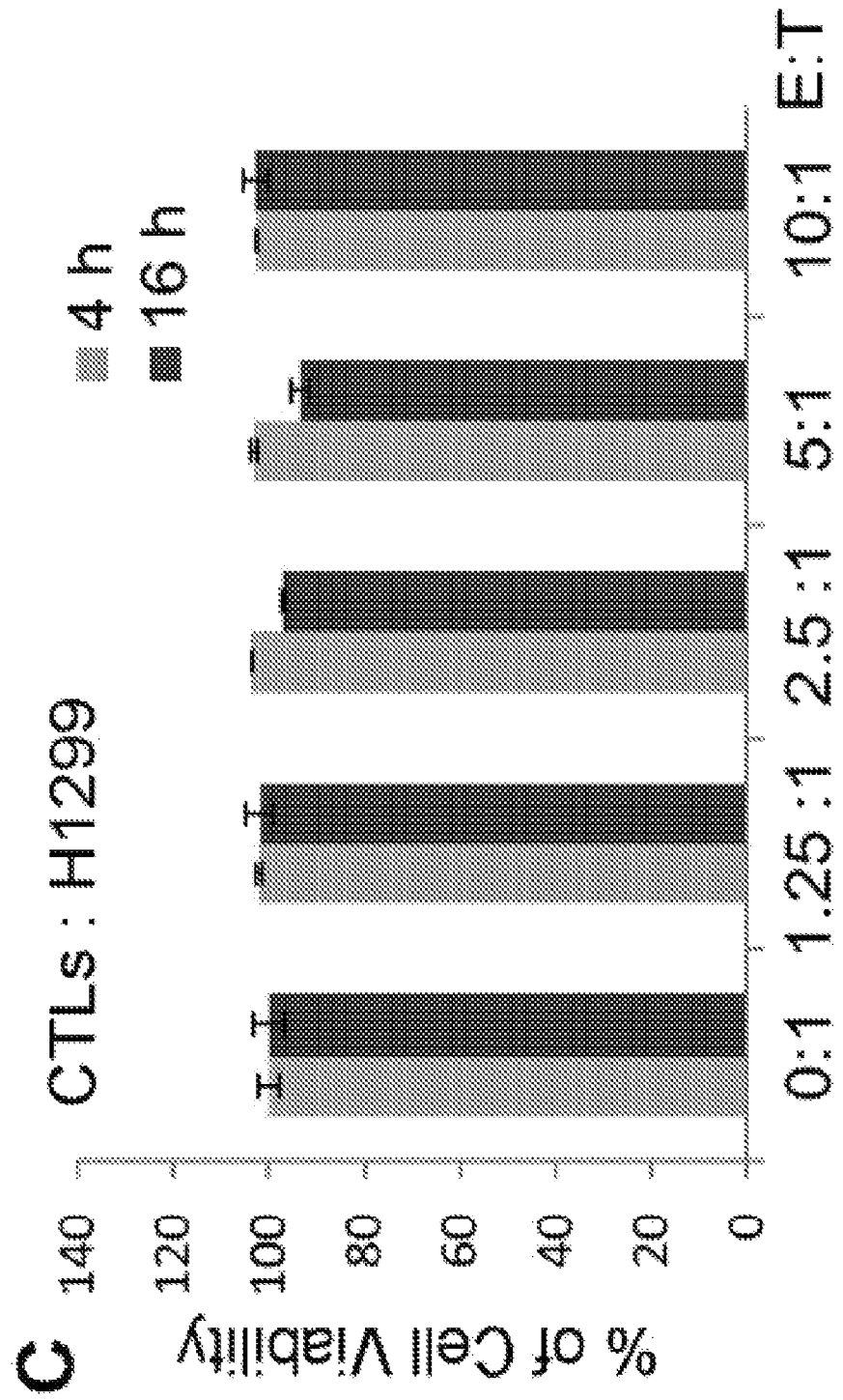
Figure 4D:
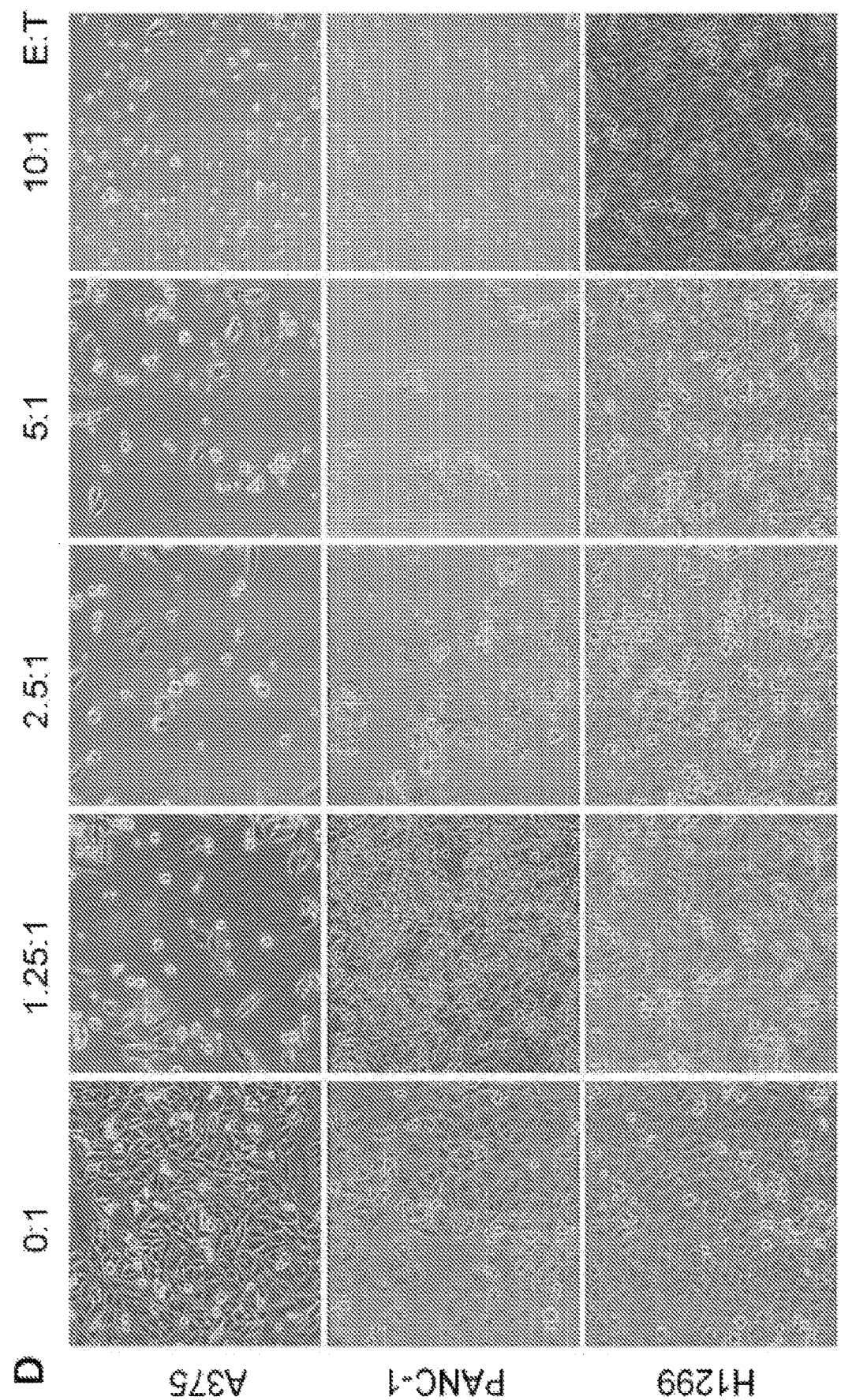
Figure 4E:
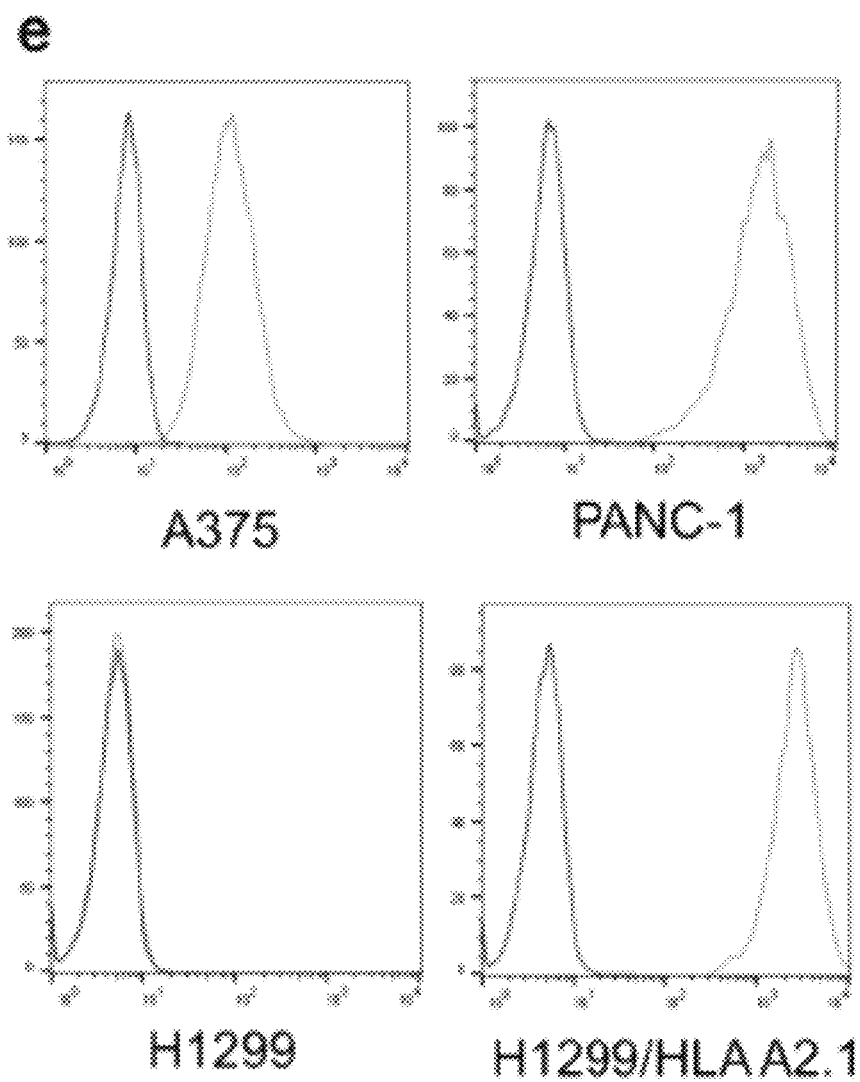
Figure 4F:
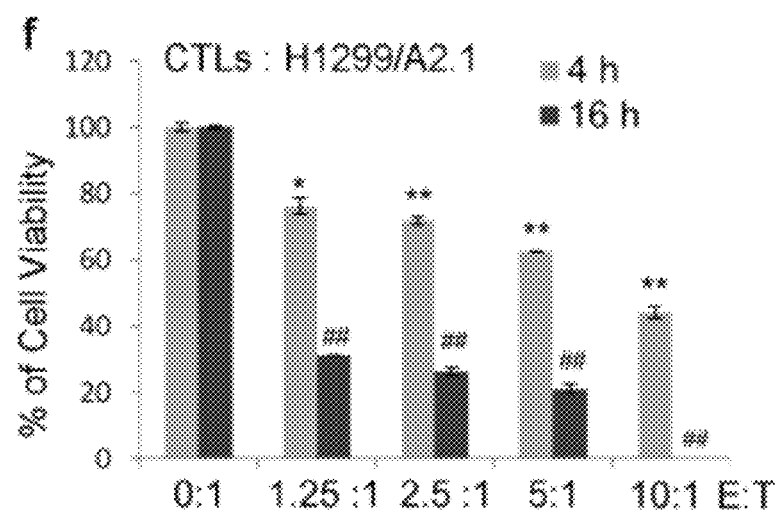
Figure 4G:
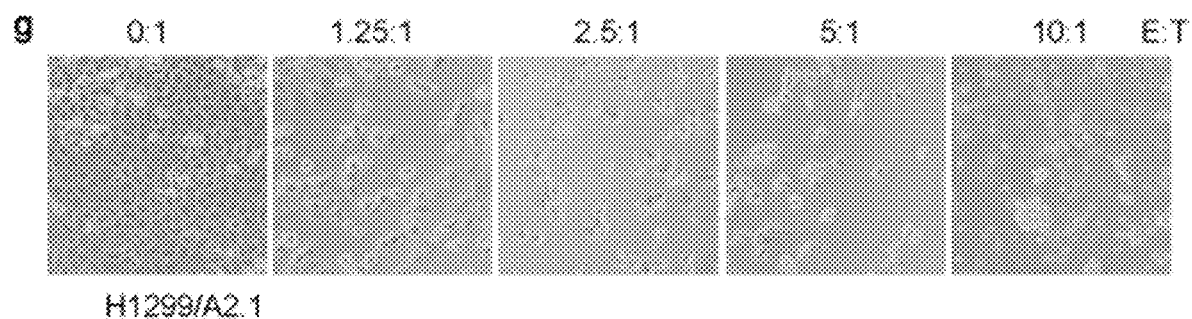

Since the Tax-immortalized DCs over-expressed and activated cellular proto-oncoproteins, such as c-Myc, to promote cell cycle progression and proliferation, it is plausible that the CTLs activated by ihv-DCs could recognize cancer cells in which these oncoproteins are often deregulated. To test this hypothesis, two HLA-A2+ cancer cell lines, A375 (metastatic melanoma) and PANC-1 (pancreatic cancer), and one HLA-A2-negative cell line, H1299 (lung cancer) were selected. It was shown that the ihv-DC2-activated CTLs effectively induced cytolysis of A375 and PANC-1 cells but had no apparent killing activity on H1299 cells (FIG. 4a-4d). HLA-A2.1 cDNA was next introduced into H1299 cells (FIG. 4e), and found that the HLA-A2.1+H1299 cells became sensitive to the killing mediated by the ihv-DC2-activated CTLs (FIG. 4f, 4g). Collectively, these results supported the notion that the ihv-DC2-activated CTLs had the capacity to mediate HLA-restricted target cell killing on Tax-expressing cells and cancer cells.

Expression of an hTERT Fragment in Ihv-DCs to Develop hTERT-Specific CTLs

Figure 5A:
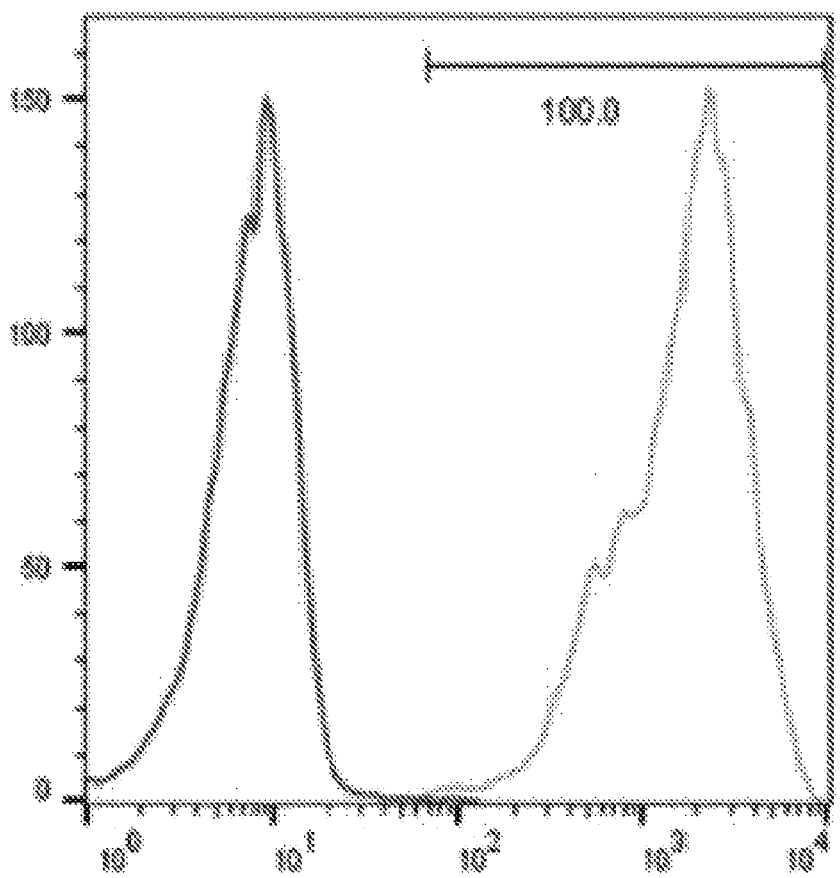
FIG. 5. Expression of an hTERT fragment in ihv-DC1 cells to generate hTERT-specific CTLs. (a) HLA-A2 expression in ihv-DC1 cells transduced with the HLA-A2.1 lentivirus. (b) Six HLA-A2-restricted CTL epitopes on hTERT (aa301-700) was depicted. (c) pTERT was generated by the fusion of IκBα with TERT (aa301-700), which was delivered into ihv-DC1 cells via lentiviral transduction. The expression of pTERT was verified with anti-IκBα immunoblot using the whole cellular extracts from ihv-DCs that were pre-treated with DMSO or with MG132 (5 μM) for 1 hour. (d) Image of the FLAG-TERT (aa301-700) expression in HLA-A2+ NIH3T3 cells using anti-FLAG antibody staining. Cell viability assay was conducted to determine the cytolysis of the 3T3L-A2.1/FLAG-TERT (aa301-700) cells by ihv-DC1- or ihv-DC1/pTERT-activated CTLs using the luciferase assay (e) and cell imaging analysis (f). **: $p<0.01$ as determined by 2-tail student t-test.

One of the significant advantages of the established dendritic cell lines is that unlike primary DCs, the DC cell lines can be genetically modified to enhance their functions in antigen presentation. To verify this idea, HLA-A2.1 was introduced into the HLA-A2-negative ihv-DC1 cells to generate ihv-DC1-A2.1 cells. Nearly 100% ihv-DC1-A2.1 cells were HLA-A2+(FIG. 5a). A known universal tumor antigen was selected and introduced into ihv-DC1-A2.1 cells. hTERT is over-expressed in more than 90% of human cancer, and constitutes numbers of recognized CTL epitopes 24. To facilitate antigen processing, a fusion construct was designed, pTERT, which consisted of the proteasomal target sequence of IκBα and the fragment of hTERT (aa301-700) that covered six HLA-A2-restricted CTL epitopes (FIG. 5b, 5c). Because the ihv-DCs exhibited a constitutive activity of NF-κB, pTERT would be expectedly degraded in a rapid rate, potentially producing abundant amounts of the TERT peptides in forming complexes with HLA molecules. pTERT was introduced into the ihv-DC1-A2.1 cells via lentiviral transduction. It was found that pTERT was barely detected in DMSO-treated ihv-DC1/pTERT cells, and the pre-treatment of these DCs with MG132, a chemical inhibitor of the proteasome, induced the accumulation of pTERT (FIG. 5c). Next, a target cell model was designed using engineered 3T3L-A2.1 cells by lentiviral transduction of FLAG-TERT (aa301-700) (FIG. 5d). ihv-DC1-A2.1 and ihv-DC1-A2.1/pTERT cells were used to prime naïve PBMCs to generate cytotoxic lymphocytes. It was found that ihv-DC1-A2.1/pTERT-activated CTLs induced cytolysis of the engineered NIH3T3 cells much more potently than ihv-DC1-A2.1-activated CTLs (FIG. 5e, 5f). These findings supported the idea that the established ihv-DCs could be further engineered to deliver a given tumor antigen intracellularly.

Non-HLA-Restricted Cancer Cell Killing by Ihv-DC1-Activated CTLs

Figure 6A:
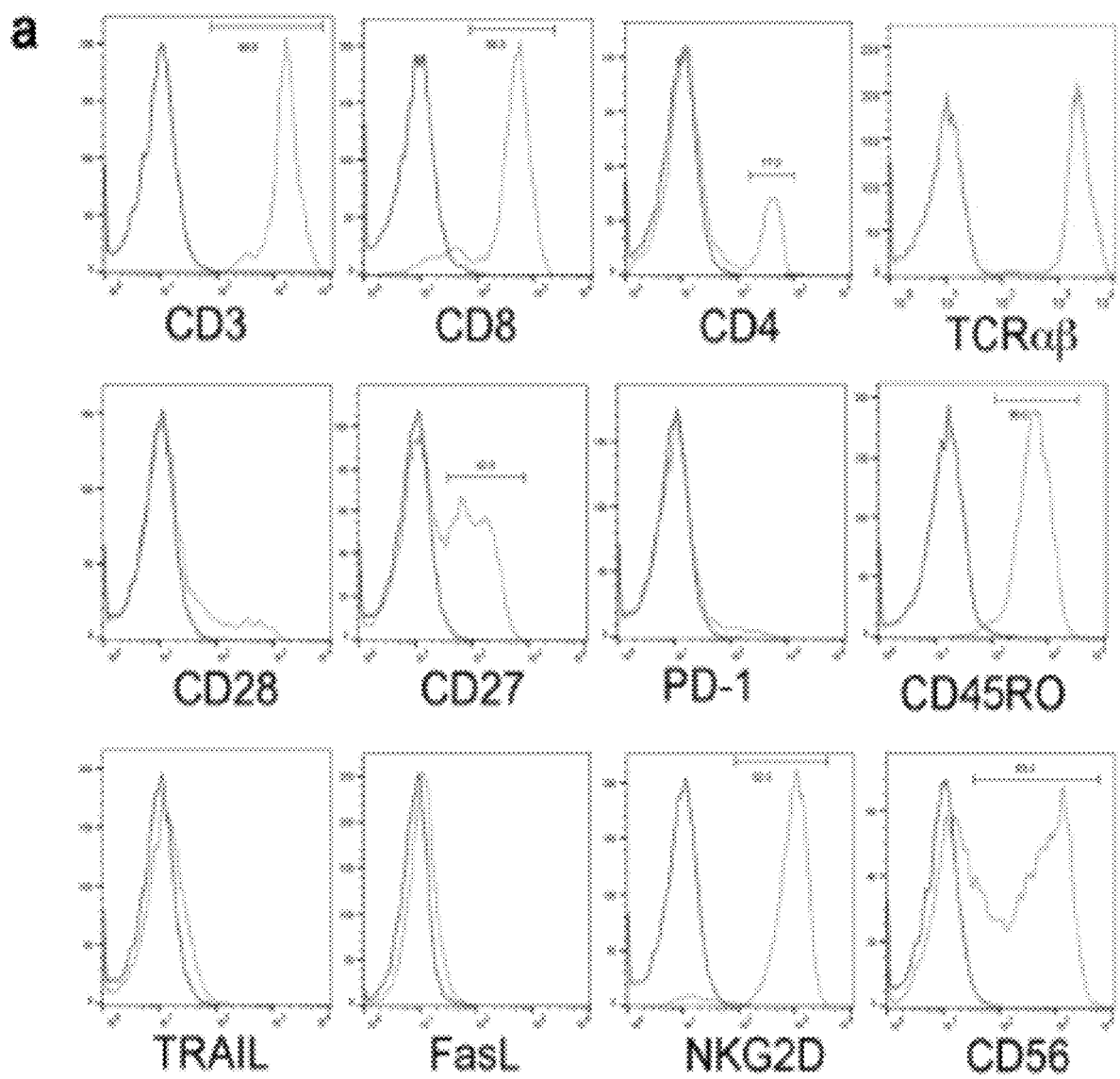
FIG. 6. Non-HLA-restricted cancer cell killing by the ihv-DC1-activated CD3+/CD56+ CTLs. (a) Immunophenotype of ihv-DC1-activated CTLs. (b) MICA/B expression in various cancer cell lines as examined by FACS. Cell viability assay was conducted to determine the cytolysis of H1299 cells (c), HeLa cells (d) and A375 cells (e) by ihv-DC1-activated CTLs using the luciferase assay. The cell imaging analysis of various cancer cell lines (f) and normal fibroblasts (g) that were incubated with ihv-DC1-activated CTLs at the indicated E:T ratios. **: $p<0.01$ as determined by 2-tail student t-test.
Figure 6B:
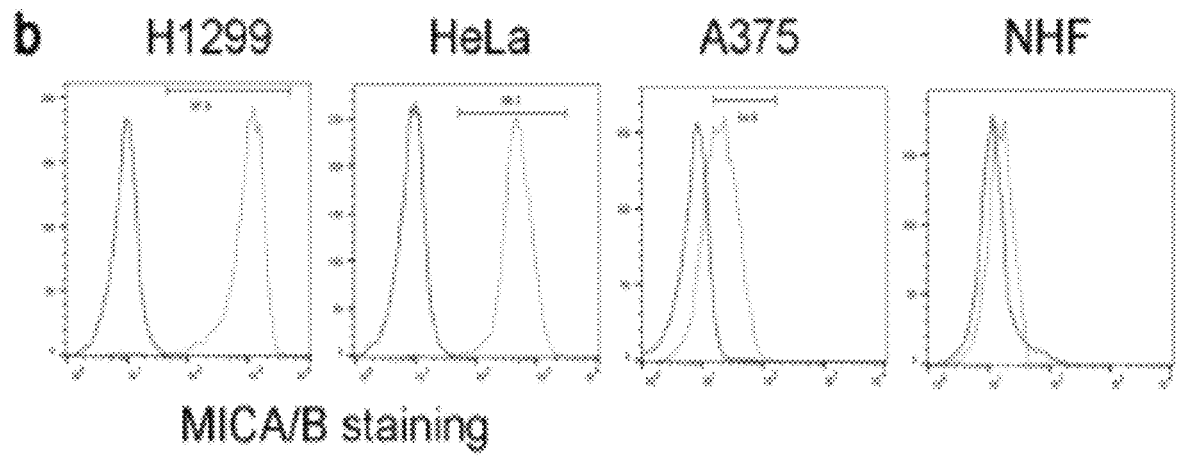
Figure 6C:
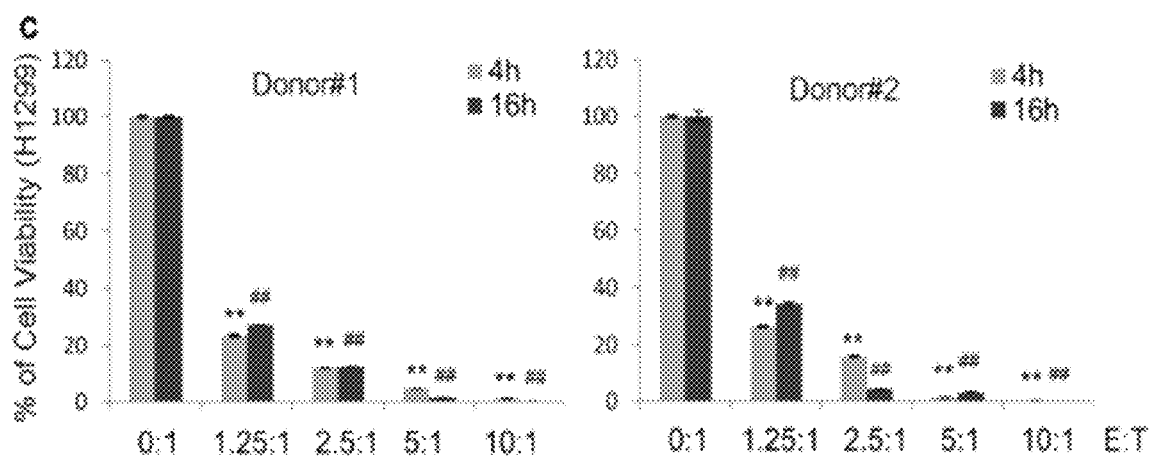
Figure 6D:
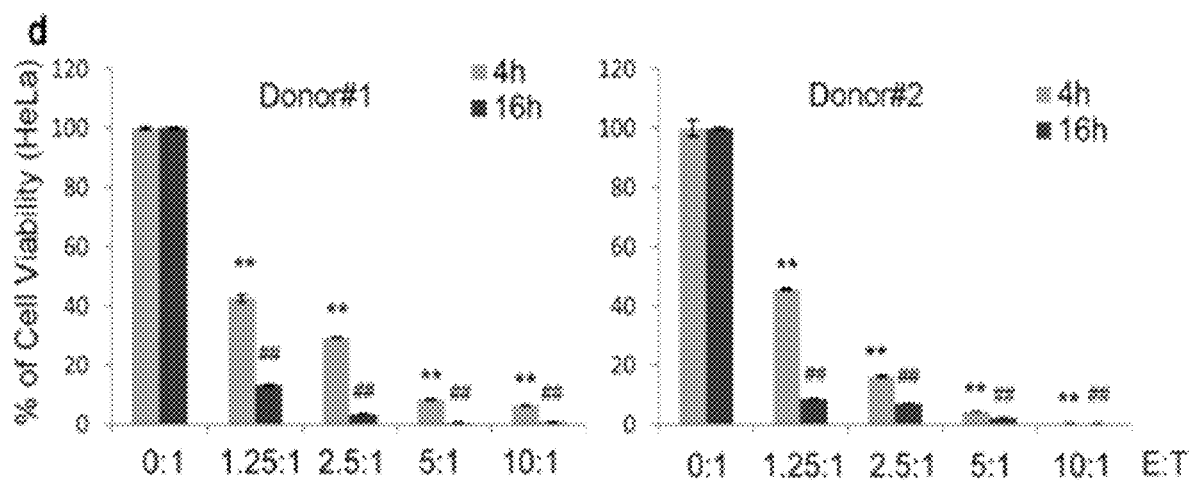
Figure 6E:
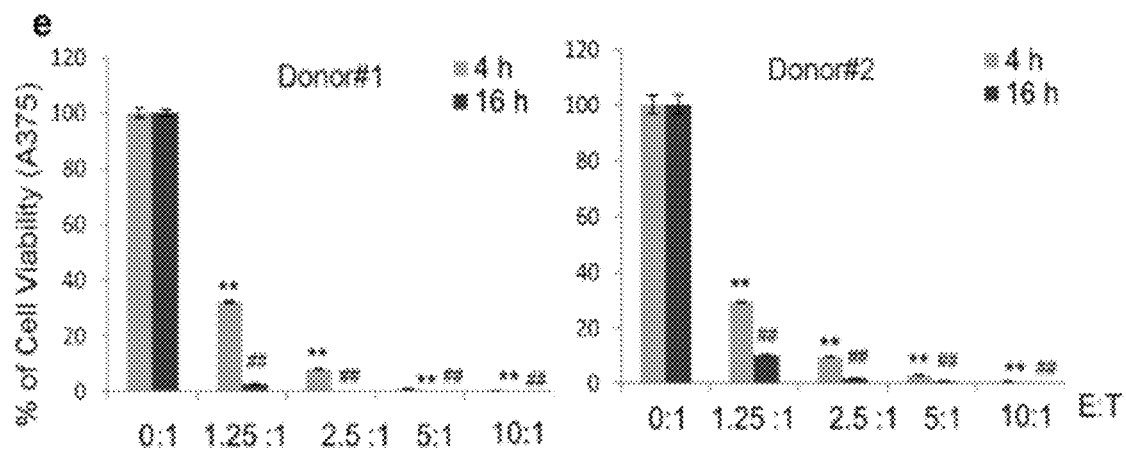
Figure 6F:
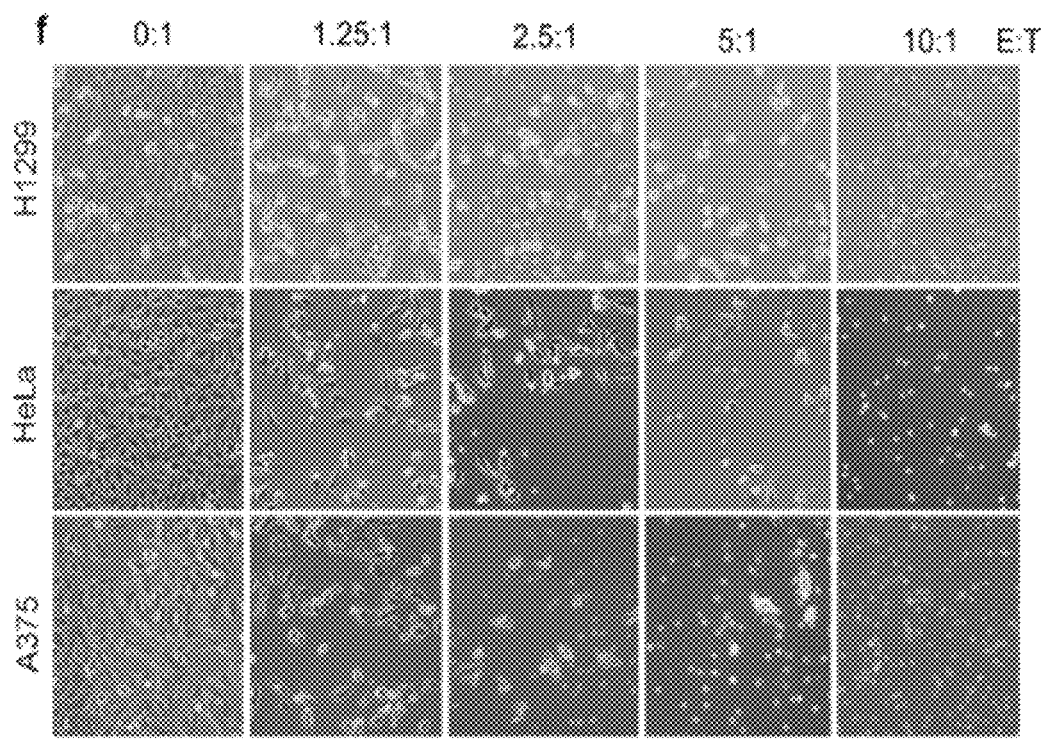
Figure 6G:
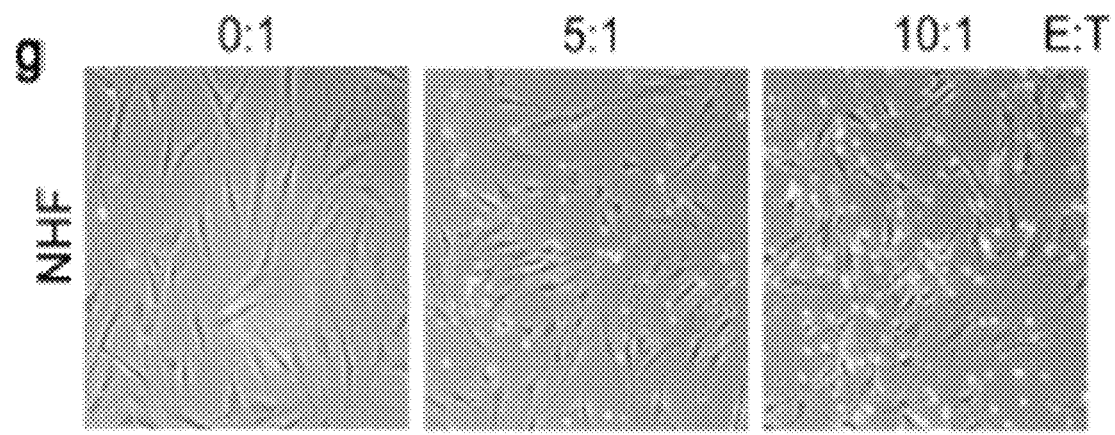

Unlike ihv-DC2 cells, the ihv-DC1-activated CTLs constituted a predominant population of CD3+/CD56+ T cells (FIG. 6a), which resembled the composition of cytokine-induced killer cells (CIK) that kill cancer cells through the interaction of NKG2D and its ligands in a non-HLA-restricted manner. The NKG2D ligands, including MICA/MICB, were selectively expressed on the surface of cancer cells and virally infected cells, but were not detected or expressed at very low levels in normal cells 25,26. This unique feature serves as a selective target for CTL-mediated killing on cancer cells. As shown in FIG. 6b, MICA/B were expressed in H1299, HeLa and A375 cells, but were undetected in normal human fibroblasts (NHF). It was found that ihv-DC1-activated CTLs very potently induced cytolysis of all these cancer cells regardless of their HLA types (FIG. 6c-6f). In contrast, these CTLs had no killing activity on NHF cells (FIG. 6g).

Figure 7A:
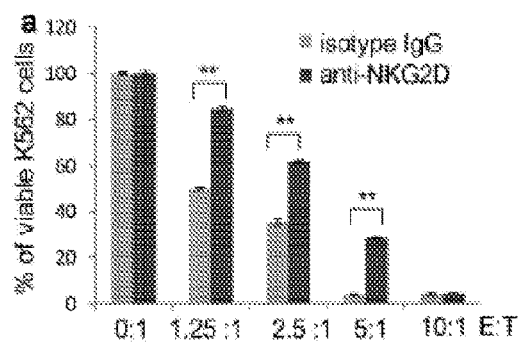
FIG. 7. ihv-DC1-activated CTLs kill cancer cells via the interaction of NKG2D and its ligands. (a) K562 cells were mixed with ihv-DC1-activated CTLs at indicated E:T ratios in the presence of isotype IgG antibody or anti-NKG2D antibody (50 μg/ml) for 4 hours. The cytolysis was determined by the luciferase assay. (b) K562 cells were mixed with ihv-DC1-activated. CTLs at the fixed E:T ratio (2.5:1) in the presence of isotype IgG antibody and anti-NKG2D antibody at indicated doses for 4 hours. (c) A375 cells were mixed with ihv-DC1-activated CTLs at indicated E:T ratios in the presence of isotype IgG antibody and anti-NKG2D antibody (50 μg/ml). The cytolysis was determined by the luciferase assay. (d) 3T3L cells were transduced with the hMICA lentivirus, and the expression of hMICA was examined by FACS. Cell viability assay was conducted to determine the cytolysis of 3T3L/vector and 3T3L/hMICA cells by ihv-DC1-activated CTLs using the luciferase assay (e) and cell imaging analysis (f). **: $p<0.01$ as determined by 2-tail student t-test.
Figure 7B:
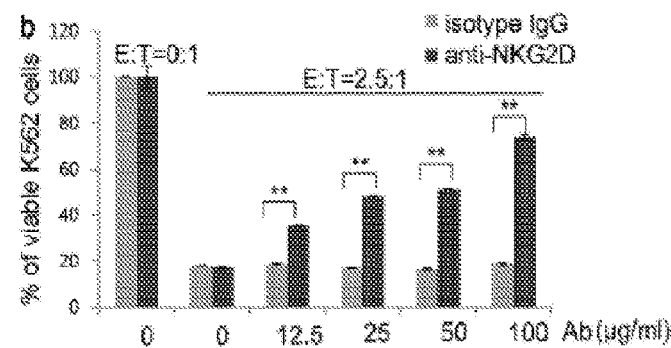
Figure 7C:
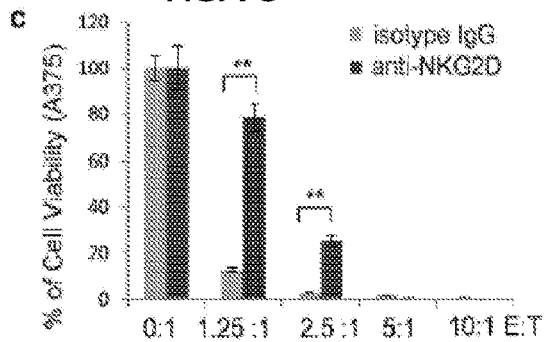
Figure 7D:
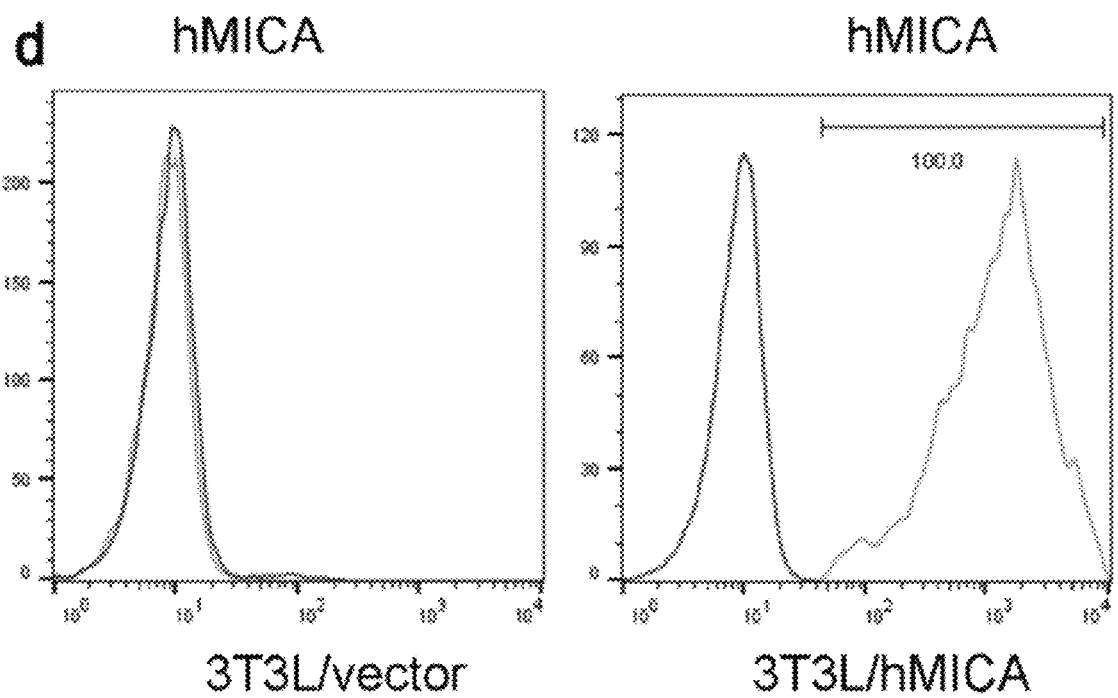
Figure 7E:
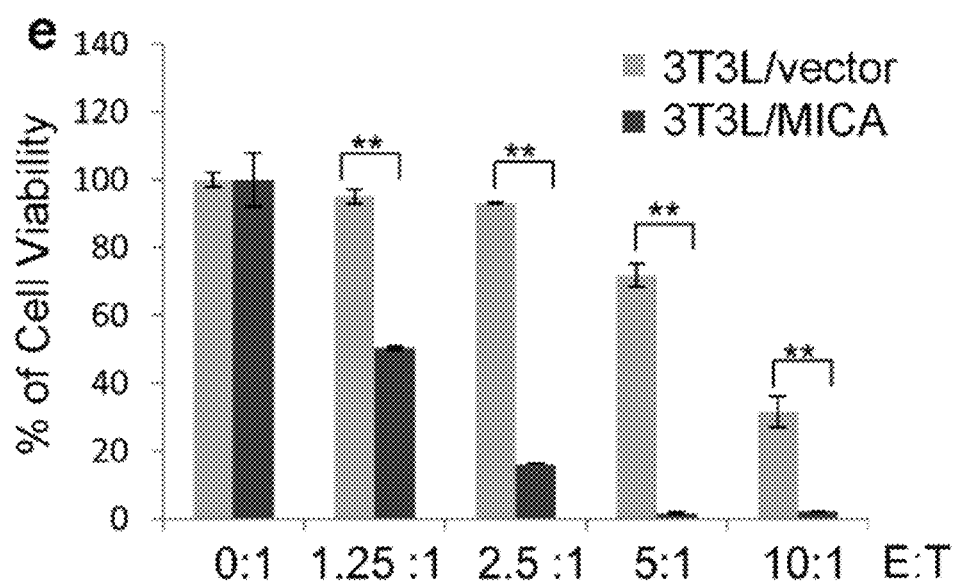
Figure 7F:
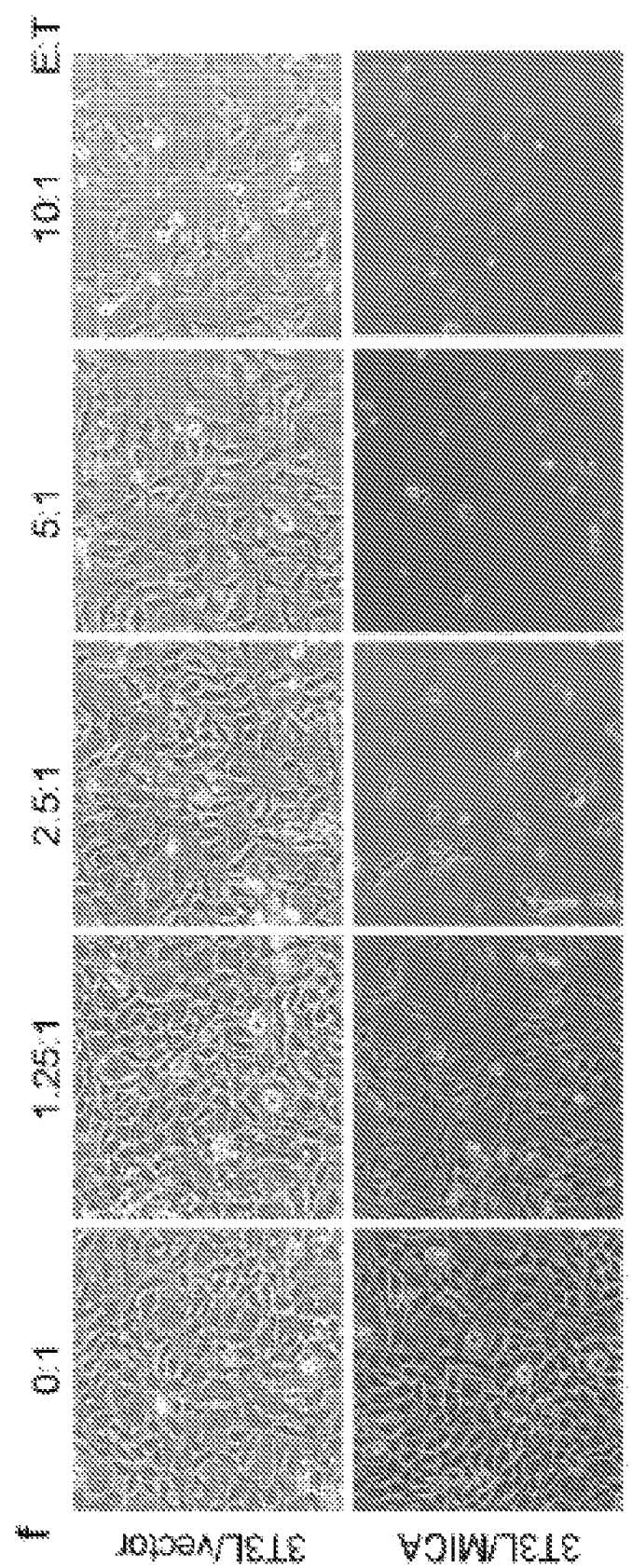

To investigate this cytolytic mechanism further, a blocking antibody was utilized for NKG2D. K562 cells were known to be resistant to CTL-mediated killing because they lack the surface expression of HLA molecules, but were sensitive to NK cells that kill target cells via the interaction of NKG2D and its ligands. At the fixed amount of anti-NKG2D antibody (50 μg/ml), it effectively prevented K562 cells from the killing by the ihv-DC1-activated CTLs at the lower E:T ratios (1.25:1 and 2.5:1) (FIG. 7a). While at the higher E:T ratios (5:1 and 10:1), the anti-NKG2D antibody appeared to be less effective in protecting K562 cells from killing (FIG. 7a). Next, a fixed E:T ratio (2.5:1) and increasing amounts of anti-NKG2D antibody was employed. It was shown that this blocking antibody prevented the ihv-DC1-CTL-mediated killing of K562 cells in a dose-dependent manner (FIG. 7b). Similarly, it was found that anti-NKG2D antibody (50 μg/ml) rescued melanoma cells from the cytolysis by the ihv-DC1-activated CTLs at the lower E:T ratios (FIG. 7c). NIH3T3 cells were further engineered by expressing luciferase, with or without human MICA (FIG. 7d). Since human HLA alleles were absent in NIH3T3 cells and therefore, the killing of these target cells by human CTLs would be unlikely mediated through the TCR recognition. It was indeed found that the ihv-DC1-activated CTLs induced cytolysis of 3T3L/hMICA cells more potently than killing 3T3L/vector cells (FIG. 7e, 7f). Collectively, these findings indicated that ihv-DC1-activated CTLs, with the predominant composition of CD3+/CD56+ T cells, induced cytolysis of cancer cells via the interaction of NKG2D and its ligands expressed on cancer cells, and they also had the capacity to kill target cells in an HLA-dependent manner as seen in FIG. 5. Furthermore, the high density of NKG2D expressed in ihv-DC1-activated CTLs could potentially overcome the neutralizing effect from soluble NKG2D ligands.

Ihv-DC1-Based Immunotherapy for Human Breast Cancer in NSG Mouse Models

Figure 8B:
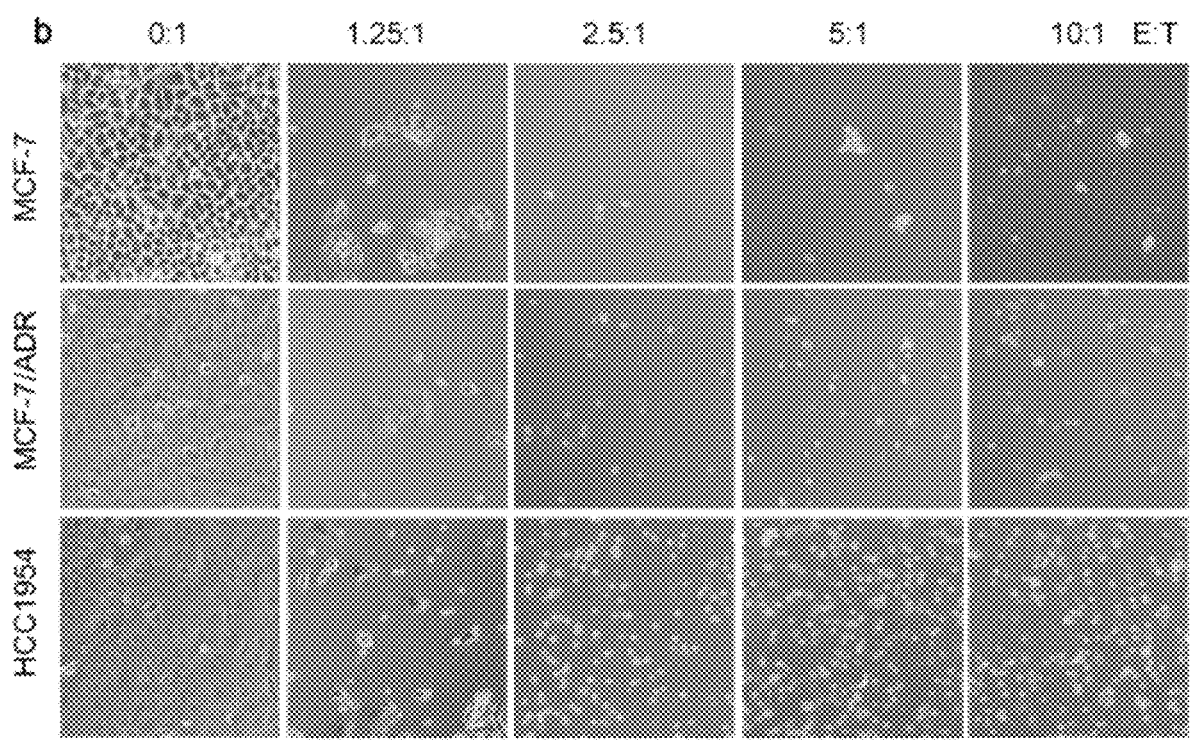
FIG. 8. ihv-DC1-activated CTLs kill breast cancer cells in an NKG2D-dependent manner. Cell viability assay was conducted to determine the cytolysis of MCF-7, MCF-7/ADR and HCC1954 cells by ihv-DC1-activated CTLs by the luciferase assay (a) and cell imaging analysis (b). (c) MICA/B expression in MCF-7, MCF-7/ADR and HCC1954 cells as examined by FACS. (d) MCF-7, MCF-7/ADR and HCC1954 cells were incubated with ihv-DC1-activated CTLs at indicated E:T ratios in the presence of isotype IgG antibody (100 μg/ml) or the NKG2D blocking antibody (100 μg/ml). The cytolysis of various cancer cell lines by ihv-DC1-activated CTLs was determined by the luciferase assay.
Figure 8C:
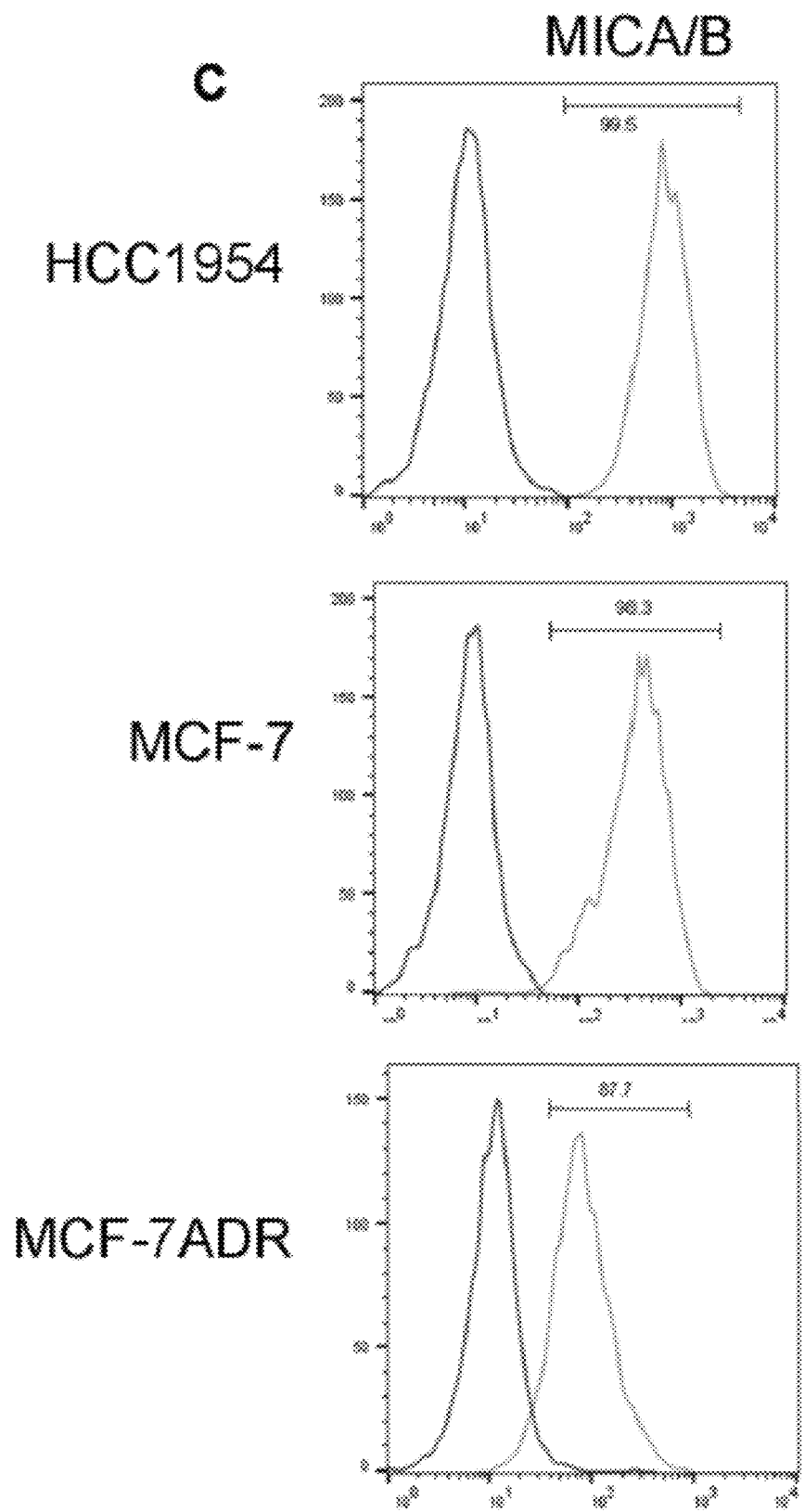
Figure 8D:
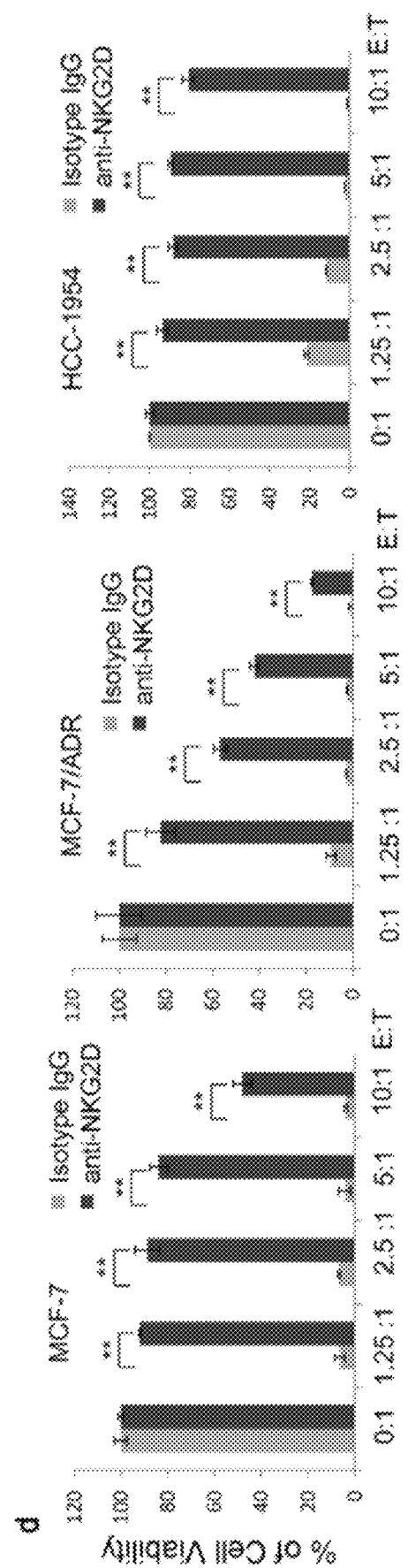

To explore the application of ihv-DCs-based immunotherapy, ihv-DC1 cells were selected for their unique ability in generating abundant amounts of CD3+/CD56+ T cells that killed cancer cells in a non-HLA-restricted manner. Three breast cancer cell lines, including MCF-7, MCF-7/ADR (a multi-chemo-resistant derivative of MCF-7) and the HER2/Neu+ HCC1954 cells, were chosen. It was observed that the ihv-DC1-activated CTLs very potently induced cytolysis of these breast cancer cells (FIG. 8a, 8b). MICA/B were expressed highly on all tested breast cancer cell lines (FIG. 8c). The NKG2D blocking antibody (100 μg/ml) efficiently prevented cancer cell killing from the CTLs (FIG. 8d).

Figure 9A:
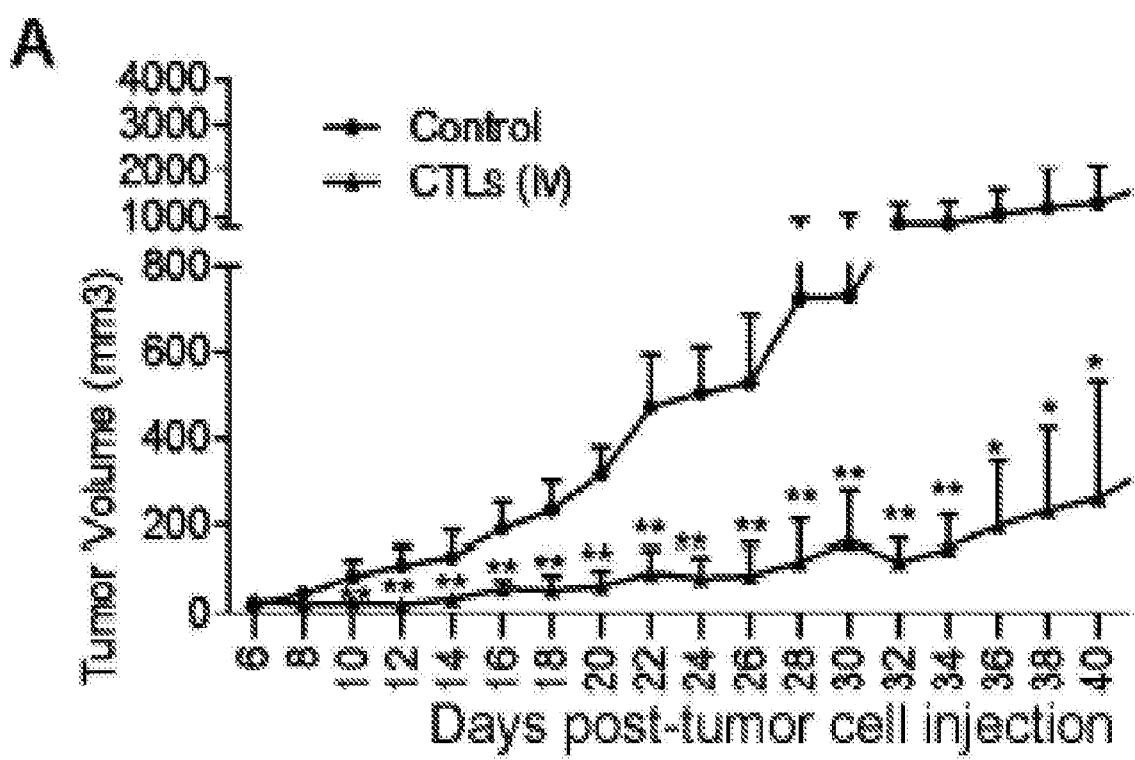
FIG. 9. ihv-DC1-activated CTLs inhibit the growth of HCC1954 tumors in NSG mice. The breast cancer xenograft and the CTL therapy were described in the METHODS. (a)
Figure 10A:
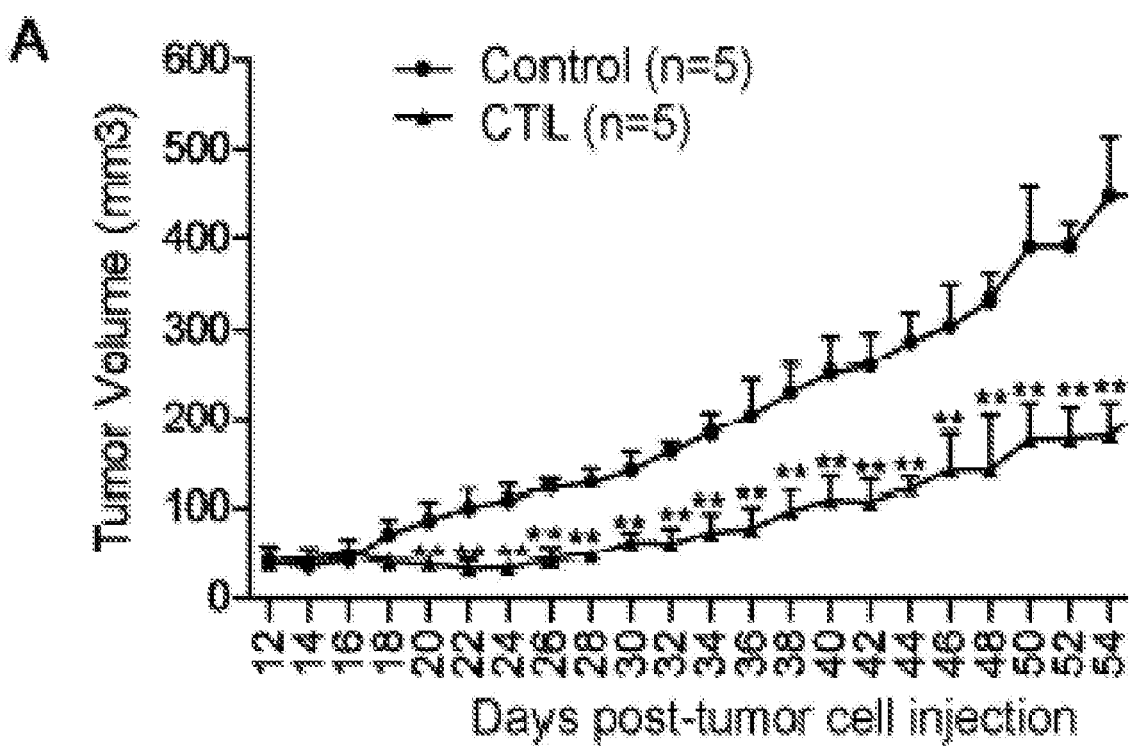
Figure 10B:
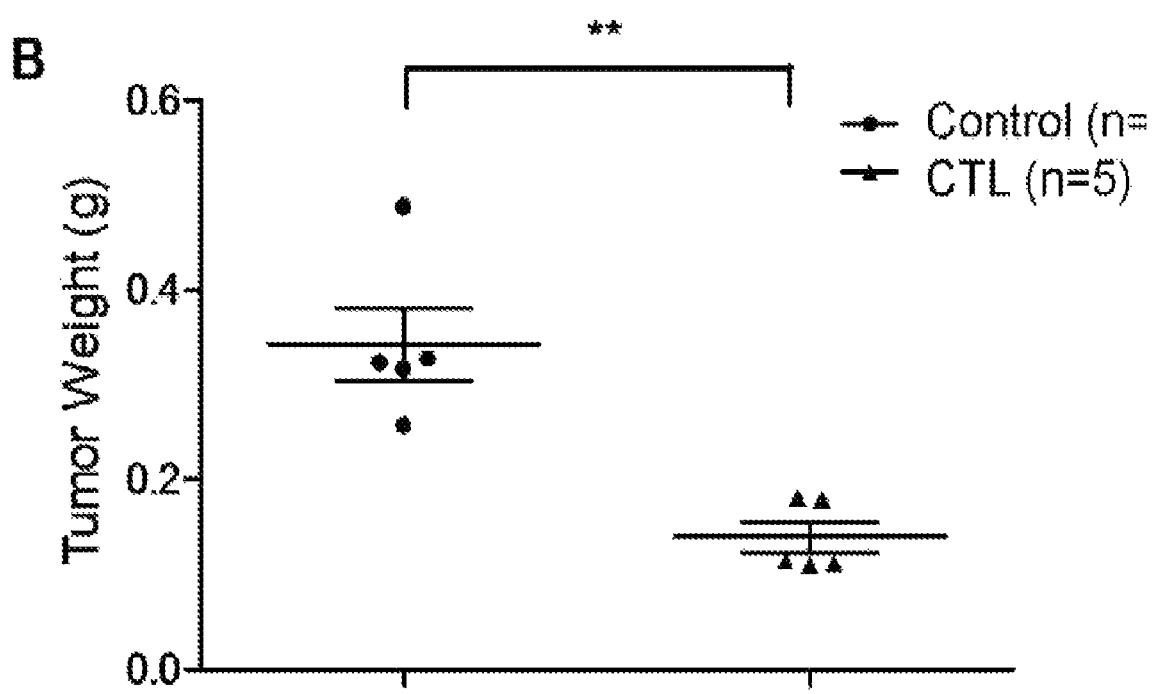
Figure 10C:
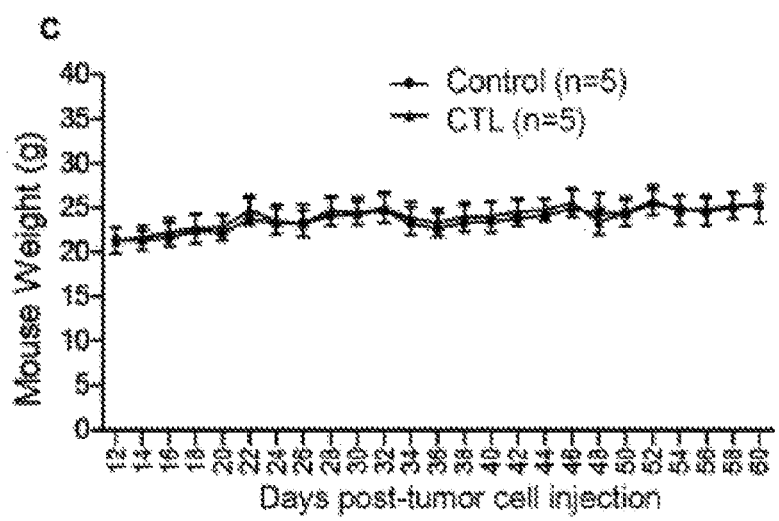
Figure 10D:
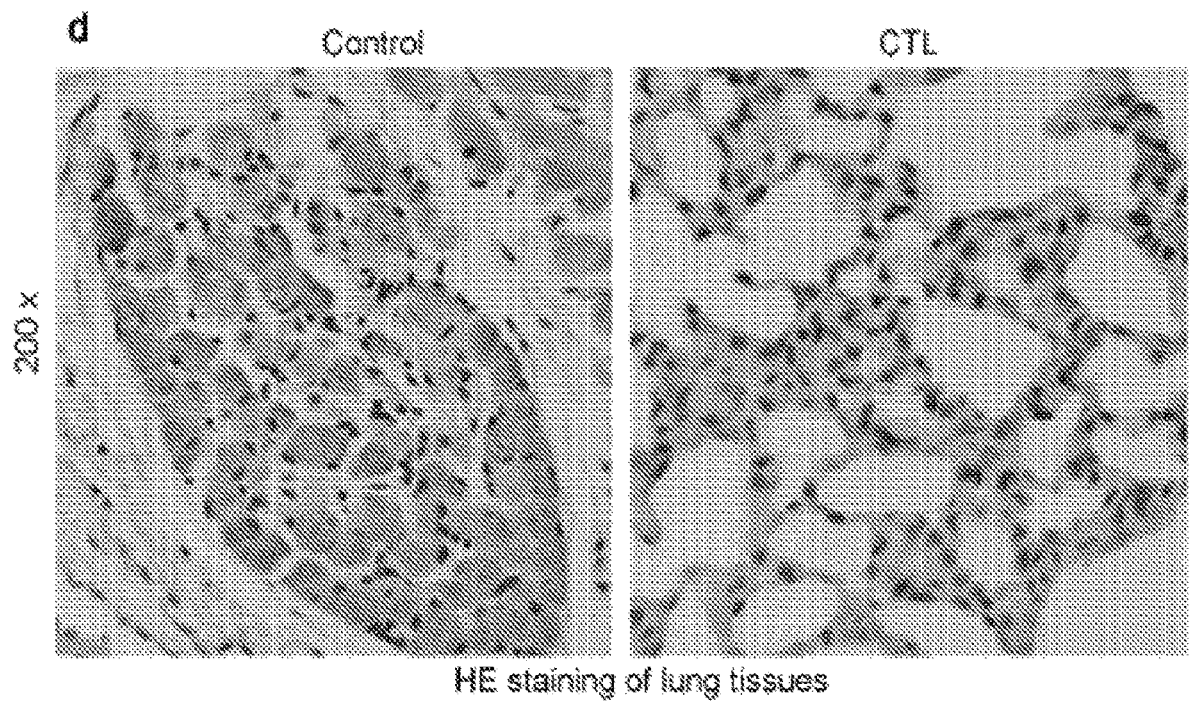
Figure 10E:
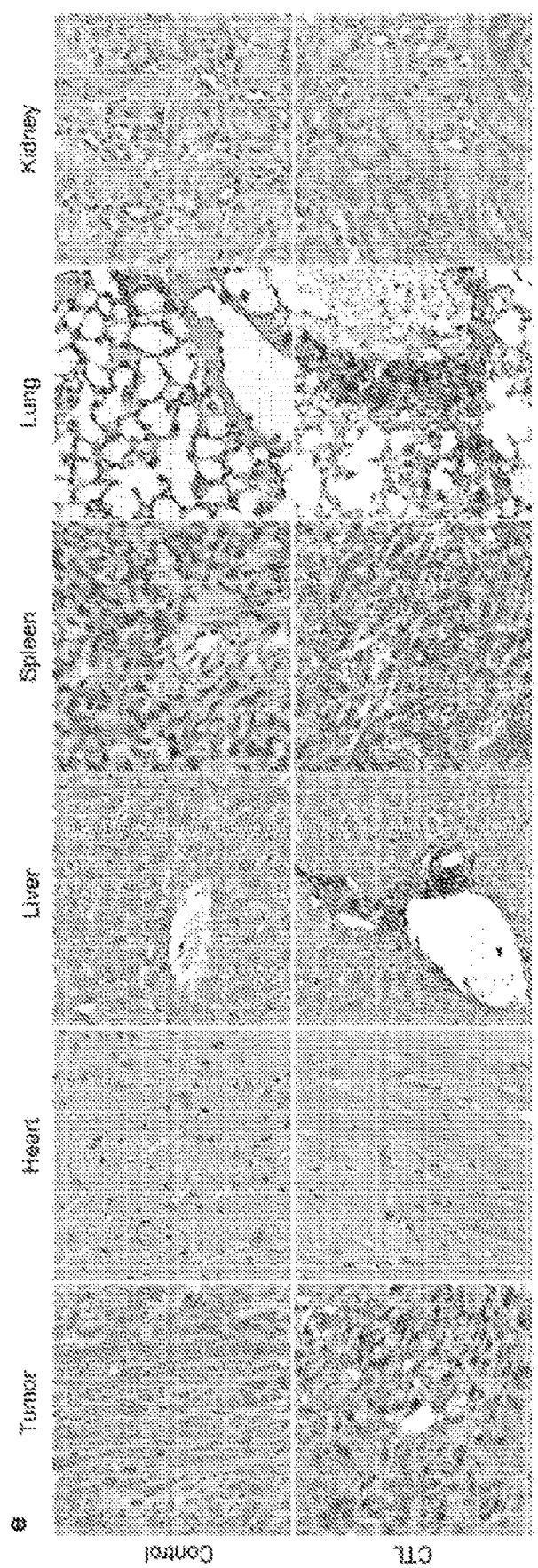

These encouraging in vitro results prompted us to investigate T cell therapy in orthotopic breast cancer NSG mouse models. In the first animal study, the ihv-DC1-activated CTLs drastically suppressed the growth of the established HCC1954 tumor in the mammary fat pads following the T cell therapy method described in the methods (FIG. 9a-9c). More strikingly, the ihv-DC1-activated CTLs effectively inhibited lung metastasis of HCC1954 tumor. In all mice of the CTL treatment group, no metastatic loci were seen, whereas the micro-metastasis in the lung from all mice of the non-treatment group was detected (FIG. 9d). Anti-human CD3 staining was next applied to assess the in vivo trafficking patterns of the infused CTLs. It was shown that human CD3+ T cells were detected in the tumor mass, spleen and lung tissues, and a few CD3+ cells were found in the liver in the CTL group mice (FIG. 9e). No infiltrating T cells were found in the heart and kidney in the CTL group mice (FIG. 9e). The second animal experiment utilized MCF-7/ADR breast cancer NSG mouse model. It was observed that similar to the HCC1954 NSG model, the ihv-DC1-activated CTLs inhibited the growth of MCF-7/ADR tumor in the mammary fat pads (FIG. 10a-10b). During the 60 days of the experiment period, no weight loss and other side effects were seen in the CTL group mice (FIG. 10c). More importantly, the ihv-DC1-activated CTLs effectively inhibited the lung metastasis of MCF-7/ADR tumor in the CTL group mice (FIG. 10d). The infused CTLs infiltrated into the tumor mass, liver, spleen and lung tissues, but not into the heart and kidney (FIG. 10e). These data, therefore, validated the therapeutic efficacy of the ihv-DC1-activated CTLs in mouse models and also indicated their desirable in vivo trafficking patterns.

Described herein is the development of immortalized and constitutively activated human primary blood dendritic cell (DC) lines, ihv-DC, by expressing the viral Tax protein that induces cell cycle progression through oncogenic activation. The ihv-DCs are a subset of CD11c+/CD205+ DCs, persistently display co-stimulatory molecules and are able to prime donor-derived lymphocytes to generate CD8+ effector cytotoxic T lymphocytes (CTLs) that can recognize and kill the Tax-expressing cells and cancer cells in an HLA-restricted manner. The ihv-DCs can be genetically modified to express a human telomerase reverse transcriptase (hTERT) fragment in priming T cells to generate HLA-A2-restricted, hTERT-specific CTLs. In addition to priming T cells to mediate HLA-restricted target cell killing, one of the ihv-DC lines, ihv-DC1, promotes robust expansion of CD3+/CD56+ CTLs with a broad anti-cancer activity through the interaction of NKG2D with its ligands expressed in cancer cells. The ihv-DC1-activated CTLs potently inhibit the growth of established tumors and suppress lung metastasis of breast cancer cells in orthotopic NSG mouse models. More importantly, the ihv-DC1-activated CTLs are able to infiltrate into primary tumor loci and metastatic site, mimicking the natural in vivo CTL trafficking features. These established human blood DCs will facilitate the development of cell-based immunotherapy.

Described herein is a new method to develop human blood dendritic cell lines by selecting PHA/IL-2 stimulated, Tax-transduced PBMCs from blood donors. The established ihv-DCs can be reliably grown and maintained in culture for prolonged time without losing their maturation and activation phenotypes. A method to amplify monocyte-derived dendritic cells (MoDCs) by expressing Tax in GM-CSF/IL-4-induced DCs that are differentiated from adherent monocytes is also described herein. In some embodiments, the second method enables growth of mature and activated MoDCs for up to three months. This method can generate adequate numbers of activated MoDCs from several million PBMCs, which is a significant advantage over the conventional MoDC method by eliminating undesirable apheresis procedures. Besides, unlike primary DCs, the established DCs can be easily modified by expressing a given tumor antigen intracellularly, thereby presenting multiple antigenic epitopes in priming CD8 T cells and enhancing the development of anti-cancer immunity.

The ability of Tax in immortalizing and activating blood DCs has not been previously reported. Without being bound by theory, the success of the effort is attributed to cell selection and culture techniques at several levels. First, PHA/IL-2 stimulate T cell proliferation, and the activated T cells could secrete soluble factors that possibly enable blood immature DCs to be transduced by the Tax lentivirus since primary immature DCs are highly resistant to lentiviral transduction. Second, because the majority of the Tax-transduced lymphocytes proliferate much faster than the Tax-transduced DCs, depletion of T cells at the early selection stage is an essential step that allows low numbers of DCs to thrive. Third, most Tax-transduced DCs could experience a "growth crisis" at the third month following transduction, and some of them regain their growth strength after passing this stage. Therefore, a continuous culture effort is necessary to aid the Tax-transduced DCs to become immortal.

One of the crucial phenotypes is that ihv-DCs are constitutively activated, with no need for additional stimulations. Tax apparently has the capacity to promote DC maturation and activation. It is reasoned that Tax-induced activation of NF-κB signaling plays a key role in the process of DC maturation and activation. Upon encountering invading pathogens, the components of pathogens stimulate TLRs such as TLR3 and TLR4 in immature DCs. TLR3 or TLR4 engagement activates the receptor-associated TRAF6, which in turn induces the activation of its downstream signaling molecules including the IκB kinase complex, the central regulator of NF-κB signaling. Kobayashi, T. et al. TRAF6 is a critical factor for dendritic cell maturation and development. *Immunity* 19, 353-363 (2003); Hull, C., McLean, G., Wong, F., Duriez, P. J. & Karsan, A. Lipopolysaccharide signals an endothelial apoptosis pathway through TNF receptor-associated factor 6-mediated activation of c-Jun NH2-terminal kinase. *The journal of Immunology* 169, 2611-2618 (2002). It is well recognized that NF-κB is the key mediator in inducing DC maturation and activation. Rescigno, M., Martino, M., Sutherland, C. L., Gold, M. R. & Ricciardi-Castagnoli, P. Dendritic cell survival and maturation are regulated by different signaling pathways, *The Journal of Experimental Medicine* 188, 2175-2180 (1998); Ardeshna, K. M., Pizzey, A. R., Devereux, S. & Khwaja, A. The PI3 kinase, p38 SAP kinase, and NF-κB signal transduction pathways are involved in the survival and maturation of lipopolysaccharide-stimulated human monocyte-derived dendritic cells, *Blood* 96, 1039-1046 (2000). TRAF6 is also necessary for activating MAP kinase, consequently inducing AP-1 activation. Bradley, J. R. & Pober, J. S. Tumor necrosis factor receptor-associated factors (TRAFs). *Oncogene* 20, 6482-6491 (2001). Further, the Stat3 activity is crucial for IL-15-derived DCs to acquire their antigen-presenting capability and to mediate polarized CD8+ T cell response. Okada, S., Han, S., Patel, E. S., Yang, L.-J. & Chang, L,-J. STAT3 signaling contributes to the high effector activities of interleukin-15-derived dendritic cells. *Immunology and Cell Biology* 93, 461-471 (2015). Consistent with these reports, it is demonstrated that ihv-DCs exhibit the constitutive activities of NF-κB, AP-1 and Stat3 as induced by Tax and possibly inflammatory cytokines such as IL-1 and TNFα, thereby contributing to their maturation and activation.

Both ihv-DC1 and ihv-DC2 cells have the ability to prime naïve PBMCs to generate antigen-specific CTLs that induce cytolysis of target cells in an HLA-restricted manner. However, ihv-DC1 cells apparently differ from ihv-DC2 cells since the former could also induce and expand CD3+/CD56+ T cells that can kill target cells in a non-MA-restricted manner. By analyzing the expression profiles of DC markers, co-stimulatory molecules and cytokines, it is believed that the level of 4-1BBL and the ratio of CD11c/4-1BBL are likely playing a crucial role in determining the fate of the composition of cytotoxic lymphocytes. Compared to ihv-DC1 cells, ihv-DC2 cells express a lower level of 4-1BBL and a higher level of CD11c, promoting generation of CD3+/CD56− T cells. Conversely, ihv-DC1 cells express a higher level of 4-1BBL and a lower level of CD11c, thereby inducing the development and expansion of CD3+CD56+ T cells. To verify this possibility, expression of 4-1BBL was enhanced in the DCs that express a low level of 4-1BBL. We have indeed found that the DCs with a much higher level of 4-1BBL primed naïve PBMCs to generate CD3+/CD56+ T cells as well as NK cells (data not shown). This phenomenon will be investigated further in the future study. Therefore, the ihv-DC1 cells are unique because they can prime naïve PBMCs to generate abundant amounts of CD3+/CD56+ effector T cells that are able to kill a variety of cancer cells regardless of their HLA types.

In theory, DC-primed T cells are antigen-specific, killing target cells in an HLA-restricted manner in an autologous setting. However, the number of tumor antigen-specific lymphocytes in healthy donors is extremely low and therefore, it is a challenging task to generate adequate numbers of tumor antigen-specific CTLs for cancer therapy using the autologous setting. Notably, up to 10% of naïve lymphocytes display alloreactive capability, recognizing the tumor antigen/HLA complex in a non-syngeneic setting. Rossjohn, J. & McCluskey, J. How a home-grown T cell receptor interacts with a foreign landscape, *Cell* 129, 19-20 (2007); Gras, S., Kjer-Nielsen, L., Chen, Z., Rossjohn, J. & McCluskey, J. The structural bases of direct T-cell allorecognition: implications for T-cell-mediated transplant rejection. *Immunology and Cell Biology* 89, 388-395 (2011); Morelli, A. E. & Thomson, A. W. Dendritic cells: regulators of alloimmunity and opportunities for tolerance induction. *Immunological Reviews* 196, 125-146 (2003). It was found that ihv-DC1-activated allogeneic CTLs are antigen-specific, recognizing the target cells that present the Tax antigen/HLA-A2 complex and the tumor antigen/HLA-A2 complex. In addition, like NK cells, the ihv-DC1-activated CTLs kill a broad range of human cancer through NKG2D that targets its ligands, a group of stress-induced surface molecules typically expressed in cancer cells and virally infected cells. Nausch, N. & Cerwenka, A. NKG2D ligands in tumor immunity. *Oncogene* 27, 5944-5958 (2008). Raulet, D. H., Gasser, S., Gowen, B. G., Deng, W. & Jung, H. Regulation of ligands for the NKG2D activating receptor. *Annual Review of immunology* 31, 413-441 (2013); Verneris, M. R., Karami, M., Baker, J., Jayaswal, A. & Negrin, R. S. Role of NKG2D signaling in the cytotoxicity of activated and expanded CD8+ T cells. *Blood* 103, 3065-3072 (2004); Karimi, M. et al. Silencing human NKG2D, DAP10, and DAP12 reduces cytotoxicity of activated CD8+ T cells and NK cells. *The Journal of Immunology* 175, 7819-7828 (2005). Through the interaction of NKG2D on CTLs with its ligands on cancer cells, the ihv-DC1-induced CTLs release cytotoxic components including perforin and granzymes, causing cancer cell death. With this respect, the ihv-DC1-activated CTLs function similarly to NK cells or to cytokine-induced killer cells (CIK) that kill cancer cells in a non-HLA-restricted manner. Marten, A. et al. Enhanced lytic activity of cytokine-induced killer cells against multiple myeloma cells after co-culture with idiotype-pulsed dendritic cells. *Haematologica* 86, 1029-1037 (2001); Wang, Y.-F. et al. Cytokine-induced killer cells co-cultured with complete tumor antigen-loaded dendritic cells, have enhanced selective cytotoxicity on carboplatin-resistant retinoblastoma cells. *Oncology Reports* 29, 1841-1850 (2013); Wongkajornsilp, N. et al. Sunitinib indirectly enhanced anti-tumor cytotoxicity of cytokine-induced killer cells and CD3+CD56+ subset through the co-culturing dendritic cells. *PloS One* 8, e78980 (2013); Castillo, E. F., Stonier, S. W., Frasca, L. & Schluns, K. S. Dendritic cells support the in vivo development and maintenance of NK cells via IL-15 trans-presentation. *The Journal of Immunology* 183, 4948-4956 (2009); Denman, C. J. et al. Membrane-bound IL-21 promotes sustained ex vivo proliferation of human natural killer cells. *PloS One* 7, e30264 (2012); Domogala, A., Madrigal, J. A. & Saudemont, A. Natural killer cell immunotherapy: from bench to bedside. *Frontiers in Immunology* 6, 264 (2015); Childs, R. W., & Carlsten, M. Therapeutic approaches to enhance natural killer cell cytotoxicity against cancer: the force awakens. *Nature Reviews Drug Discovery* 14, 487-498 (2015). Moreover, these CTLs still retain their ability to recognize target cells via the tumor antigen/HLA complex. Furthermore, under the HLA-matched conditions, these CTLs attack cancer cells via two mechanisms: the TCR recognition on the TAA/HLA complex and the NKG2D interaction with its ligands, potentially offering an optimal therapeutic efficacy.

In summary, the ihv-DC models offer several notable features. (a) ihv-DCs are activated and mature DCs, thereby eliminating the need of the complex maturation and activation process to acquire functional DCs. (b) ihv-DCs cells constitutively express abundant amounts of the co-stimulatory receptors including CD80, CD86 and CD70, which stimulate antigen-specific CD8+ cytotoxic T cells to proliferate. (c) ihv-DCs also express the chemokine receptor CCR7, the lymphoid tissue homing receptor. (d) The ihv-DC model can provide a particularly useful tool to study dendritic cell biology. These DCs can be modified genetically for investigating the role of existing or putative co-stimulatory receptors that mediate or enhance a protective anti-cancer or anti-viral immunity.

Materials and Methods

Cell Lines, Antibodies and Cytokines.

H1299, PANC-1, HCC1954, MCF-7, HeLa and NIH3T3 cell lines were obtained from ATCC. MCF-7/ADR cell line was described previously. Wu, L. et al. The reversal effects of 3-bromopyruvate on multidrug resistance in vitro and in vivo derived from human breast MCF-7/ADR cells. *PloS One* 9, e112132 (2014). A375 and NHF cell lines were kindly provided by Drs. Isaiah J. Fidler and Jieyu Zhu respectively. MT4 cells were obtained from NIH AIDS reagent program.

Recombinant IL-2 was acquired from AIDS research and reference reagent program. TNFα was purchased from R&D and LPS was from Sigma. Antibodies for perforin (PRF1) and granzyme B (GZMB) were from Santa Cruz Biotechnology, and anti-beta-actin from Sigma (St. Louis, Mo.). Anti-phospho-Stat proteins and anti-Bcl-2 family proteins were obtained from Cell Signaling. The NKG2D blocking antibody and isotype IgG control antibody as well as various APC- or FITC-labeled antibodies were purchased from Biolegend. GM-CSF-Fc4 and IL-4-Fc4 proteins are generated from 293 cells transduced with the lentivirus fusion gene constructs using PCR-based cloning method with the cDNAs of GM-CSF, IL-4 and IgG4 obtained from Open Biosystems.

Lentiviral Vector, Viral Production and Transduction.

The tax gene from HTLV-2 was fused with the fragment encoding enhanced green fluorescence protein (EGFP), and the tax2-gfp fusion fragment was cloned into the lentiviral vector in which the human elongation factor promoter drives the expression of transgene. The lentiviral vectors that express HLA-A2 (cDNAs from A375 cells), B2M (cDNA from normal lymphocytes) and MICA (cDNA from A375 cells) were constructed using the PCR-based cloning method. To generate the fusion gene construct, pTERT (aa301-700), IκBα (cDNA from normal lymphocytes) and hTERT (aa301-700) (cDNAs from U2OS cells) were amplified by the high fidelity PCR, enzyme-digested and inserted into the lentiviral vector.

To generate recombinant lentiviruses, the lentiviral construct was co-transfected with the packaging plasmid mix containing the expression plasmids for VSV-G, Gag-Pol and Rev (Invitrogen) into 293 cells using SuperFect transfection reagent (Qiagen). The viral supernatants were collected and were subjected to ultracentrifugation at 25,000 rpm/4° C. for 2 hours. The virus pellets were resuspended and were stored at −80° C.

To generate target cell lines expressing luciferase, PANC-1, A375, HeLa, H1299, MCF-7, MCF-7/ADR, HCC1954, MT4 and NIH3T3 cells were transduced with the luciferase lentivirus at the multiplicity of infection (MOI) of 10. The expression of luciferase in these cell lines was verified by the luciferase activity assay using the kit from Promega according to the manufacturer's recommended protocol. The pTERT-expressing DCs were generated by the pTERT lentiviral transduction for ihv-DCs at the MOI 20.

Generation of Ihv-DC Cell Lines.

Leukopaks were obtained from New York Blood Bank. Human peripheral blood mononuclear cells (PBMCs) were isolated from leukopaks and stimulated with PHA (5 µg/ml) for 24 h, followed by adding recombinant IL-2 (100 units/ml). The activated PBMCs were cultured for 4-5 days and were then transduced with the Tax2-GFP lentivirus in the presence of polybrene (10 µg/ml). The transduced cells were cultured continuously in the complete RPMI1640 medium containing 10% fetal bovine serum (Sigma) and 100 units/ml of recombinant IL-2. Alternatively, the transduced cells were cultured in RPMI1640 medium supplemented with 5% heat-inactivated human AB serum (Sigma). Two to three weeks following transduction, the transduced cells were negatively selected with anti-CD3 magnetic beads (Life technologies) to deplete T cells. CD3-negative cells were maintained in culture continuously and were analyzed for their immunophenotypes about three months following transduction. Two DC cell lines were established from two blood donors, and were named as ihv-DC1 and ihv-DC2. The ihv-DC1 cells lost CD40 during the passages of culture and CD40 was restored by the CD40 lentiviral transduction. The ihv-DCs were grown in the RPMI1640 medium supplemented with 10% FBS or 5% heat-inactivated human AB serum in the presence of IL-2 (50-100 units/ml)

To generate monocyte-derived DCs, adherent monocytes from 4 million PBMCs were stimulated with GM-CSF-Fc4/IL-4-Fc4 using the conditioned medium of the GM-CSF-Fc4/IL-4-Fc4-producing 293 cells at 1:10 dilution for 7 days. The differentiated DCs were subsequently transduced with the Tax2-GFP lentivirus. The Tax-expressing MoDCs (MoDC-Tax) were cultured in the RPMI1640 medium with 10% FBS in the presence of GM-CSF-Fc4/IL-4-Fc4 for 5-7 days, and then continued to be maintained in culture in the presence of recombinant IL-2 at 100 units/ml. The activated MoDCs were generated by stimulating the GM-CSF-Fc4/IL-4-Fc4-differentiated MoDCs with TNFα (50 ng/ml) and LPS (1 µg/ml) for two days. The mature and activated MoDCs showed typical dendrites and were harvested for RNA and protein extractions.

Immunophenotyping Analysis by Flow Cytometry.

The immunophenotypes of ihv-DCs cells, MoDC-Tax and DC-activated lymphocytes were analyzed with FACS. Cells were stained with allophycocyanin (APC)-conjugated antibodies (Biolegend) as indicated in the figures according to the manufacturer's instructions. The stained cells were subjected to FACS analysis. For TLR3 intracellular staining, the ihv-DC cells were stained with APC-conjugated anti-TLR3 antibody or IgG isotype control antibody after permeabilization using the intracellular staining kit from eBioscience according to the manufacturer's instructions.

Allogeneic Mixed Leukocyte Reaction (MLR) Assay.

The ihv-DCs were mixed with naïve PBMCs isolated from leukopaks at the ratio of 1:100. The mixed cells were kept in culture without adding exogenous cytokines for 2-3 days, followed by adding recombinant IL-2 (100 u-200 units/ml). The proliferation of the ihv-DC-reactive lymphocytes was monitored with FACS, and the presence of ihv-DCs in the mixed culture was monitored using fluorescence microscopy. 2-3 weeks following MLR, the ihv-DC-activated lymphocytes were analyzed with FACS and were examined for their cytotoxic activity on target cells.

Cytotoxicity Assay.

Various cell lines that were modified to express luciferase were used as targets, while the ihv-DC-activated lymphocytes generated from 18-21 days following MLR were served as effectors. Cancer cells were first placed in 24-well plates for 2 hours for complete attachment. The ihv-DC-activated lymphocytes were then placed on cancer cells at the indicated E:T ratios. At the 4 h or 16 h timepoint following co-culturing effector and target cells, viable cells were washed with PBS buffer to remove cellular debris and were subjected to the luciferase activity assay using the kit from Promega. The cytotoxic activity of the ihv-DC-activated lymphocytes therefore was determined by comparing the luciferase activities in the target cells that were treated without or with the cytotoxic lymphocytes at the indicated E:T ratios.

Electrophoretic Mobility Gel Shift Assay (EMSA).

Nuclear extracts were prepared from various cell lines using NE-PER nuclear and cytoplasmic extraction reagents (Pierce). The oligonucleotide was 5'-end-labeled with biotin (Integrated DNA Technologies) and annealed to its complementary strand. The binding activities were examined by EMSA using a light shift chemiluminescent EMSA kit (Pierce) following the protocol reported previously (Jain, P. et al. DC-SIGN mediates cell-free infection and transmission of human T-cell lymphotropic virus type 1 by dendritic cells. *Journal of Virology* 83, 10908-10921 (2009).). The oligonucleotide probes are for STAT3 (5'-GATCCTTCTGG-GAATTCCTAGATC-3') (SEQ ID NO:18), NF-κB (5'-GAT-CCGGCAGGGGAATCTCCCTCTC-3') (SEQ ID NO:19) and AP-1 (5'-CGCTTGATGACTCAG-CCGGAA-3') (SEQ ID NO:20).

Immunofluorescence Imaging.

Cells were washed with PBS and fixed for 20 min with 4% para-formaldehyde and 10 min with 0.1% Triton® X-100. After washing, cells were incubated with 5% goat serum albumin as the blocking solution. The primary antibody anti-Flag (1:100, sigma, USA) was applied, followed by the secondary antibody, anti-rabbit Alexa Fluor 488 (Cell Signaling, USA) at the dilution of 1:200. After washed for three times with cold TBST buffer, and the cell nuclei were stained with DAPI (1:2000, Cell Signaling, USA). The stained cells were examined using fluorescence microscopy (Nikon E800, Japan).

Quantitative Real-Time PCR (qRT-PCR).

Total RNA was isolated using the RNeasy kit (Qiagen), and its concentration was determined using the Nano-Drop1000 spectrophotometer (Thermo Scientific). The quality and integrity of total RNA was assessed on 1% formaldehyde-agarose gels. cDNA was synthesized using the Omniscript reverse transcriptase kit (Qiagen) following the manufacturer's recommended protocol. Template samples in triplicate were subjected to the real-time quantitative PCR (Stratagene Mx3005P system) using Power SYBR Green (Applied Biosystems). The primer sequences are listed in Table 1.

TABLE 1

Primers for real-time PCR analysis

| Gene | Forward (5'-3') | Reverse (5'-3') |
|---|---|---|
| GAPDH | GCACCGTCAAGGCTGAGAAC SEQ ID NO: 21 | TGGTGAAGACGCCAGTGGA SEQ ID NO: 22 |
| IL-1A | CAGTGCTGCTGAAGGAGATG SEQ ID NO: 23 | AACAAGTTTGGATGGGCAAC SEQ ID NO: 24 |
| IL-1B | TGGCAATGAGGATGACTTGT SEQ ID NO: 25 | TGGTGGTCGGAGATTCGTA SEQ ID NO: 26 |
| IL2 | CTCACCAGGATGCTCACATTTA SEQ ID NO: 27 | CCTCCAGAGGTTTGAGTTCTTC SEQ ID NO: 28 |
| IL6 | GGAGACTTGCCTGGTGAAA SEQ ID NO: 29 | CTGGCTTGTTCCTCACTACTC SEQ ID NO: 30 |
| IL8 | CTGGCCGTGGCTCTCTTG SEQ ID NO: 31 | CCTTGGCAAAACTGCACCTT SEQ ID NO: 32 |
| IL10 | TTTCCCTGACCTCCCTCTAA SEQ ID NO: 33 | CGAGACACTGGAAGGTGAATTA SEQ ID NO: 34 |
| IL-12A | CCTTGTGGCTACCCTGGTCCTC SEQ ID NO: 35 | CTCAGCAGGTTTTGGGAGTGGT SEQ ID NO: 36 |
| IL12B | ACCAGAGCAGTGAGGTCTTA SEQ ID NO: 37 | CTCCTTTGTGACAGGTGTACTG SEQ ID NO: 38 |
| IL15 | GAGTCCGGAGATGCAAGTATTC SEQ ID NO: 39 | CCTCCAGTTCCTCACATTCTTT SEQ ID NO: 40 |
| IFNA1 | ACCCACAGCCTGGATAACAG SEQ ID NO: 41 | ACTGGTTGCCATCAAACTCC SEQ ID NO: 42 |
| IFNA2 | TCAATCTCTTCAGCACAAAGGA SEQ ID NO: 43 | ATCACACAGGCTTCCAGGTC SEQ ID NO: 44 |
| IFNB1 | TCTCCTGTTGTGCTTCTCCA SEQ ID NO: 45 | GTCAAAGTTCATCCTGTCCTTG SEQ ID NO: 46 |
| TGF-β | GCCGAATTCCGGATCTACAA SEQ ID NO: 47 | CTCCTGGAGCACCTGATAAAC SEQ ID NO: 48 |
| IFN-γ | CCCATGGGTTGTGTGTTTATTT SEQ ID NO: 49 | AAACCGGCAGTAACTGGATAG SEQ ID NO: 50 |
| TNFα | GATCCCTGACATCTGGAATCTG SEQ ID NO: 51 | GAAACATCTGGAGAGAGGAAGG SEQ ID NO: 52 |
| cMyc | CAGAGGAGGAACGAGCTAAA SEQ ID NO: 53 | TTGGACGGACAGGATGTATG SEQ ID NO: 54 |

Animals and Xenograft Models.

The animal study was performed using the approved IACUC protocol. Female NSG mice (4-6 weeks, 18-22 g weight) were obtained from the animal center at the University of Maryland School of Medicine, and were housed in a specific pathogen-free room. MCF-7/ADR cells (4 million), HCC1554 cells (1 million) were collected and resuspended in Hanks buffer with an equal volume of Matrigel (BD, USA) and then were injected into the mammary fat pads of female NSG mice. After cancer cell implantation, the mice were randomized into two groups (CTL and control). The treatment began when tumors were palpable. The treatment group mice were injected via the tailvein of mice with the ihv-DC1-activated CTLs (q5d×8, 20 million in 100 μL plus 1,000 u recombinant IL-2), and the control group mice were injected via the tailvein of mice with Hanks buffer (q5d×8, iv, 100 μL plus 1,000 u recombinant IL-2). The animals' weight was measured every 2 days. The tumor growth was recorded starting from the first day of the treatment and was measured for the volume of the xenograft every 2 days. The tumor volume (V) was calculated using the formula $V=\pi a*b2/6$, where a and b are the longest and shortest diameters, respectively.

Immunohistochemistry and HE Staining.

Tissue sections were incubated at 60° C. for 10 min and then deparaffinized in xylene and subsequently in ETOH and DI water. After deparaffinization, tissue sections were immersed into a preheated antigen unmasking solution (Vector, CA, USA), placed into a pressure cooker for 5-10 min and then cooled to room temperature under cold water. The anti-human CD3 antibody (1:100) was used to stain the pre-treated tissue sections. Then the endogenous peroxidase activity was blocked by incubation of tissue sections with 3% hydrogen peroxide in PBS for 10 min. Biotinylated goat anti-mouse IgG Antibody (H+L) (1:200) (Vector, CA, USA) was applied as the secondary antibody. A VECTASTAIN Elite ABC HRP Kit (Vector, CA, USA) was used as chromogen, and hematoxylin counterstain was also performed.

The protocol was detailed in Table 2. HE staining (paraffin-embedded) was conducted by the Pathology Electron Microscopy and Histology Laboratory, University of Maryland School of Medicine.

TABLE 2

| Deparaffinization | Xylene(10 min), Xylene(5 min), 100% ETOH(2 min), 100% ETOH(2 min), 95% ETOH(2 min), 75% ETOH(2 min), Distilled Water(2 min) |
|---|---|
| Unmask treat | Pressure cook |
| Blocking 5% Goat serum | 30 min |
| Blocking 0.1 mg/ml Fab GXM(H + L) | 60 min |
| Primary antibody (CD3) | Overnight |
| 3% H$_2$O$_2$ in PBS blocking | 10 min |
| Secondary antibody (Biotinylated anti-mouse IgG(H + L)) | 30 min |
| Vector ABC kit Substrates | Novored |
| Nucleus stain | Hematoxylin |

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

I claim:

1. An engineered primary blood dendritic cell, wherein the dendritic cell is genetically engineered to express a functional Tax protein from a T cell leukemia virus, wherein the dendritic cell is CD205+ and CD11c+, wherein the dendritic cell presents one or more antigens or antigenic fragments or variants thereof, wherein the one or more antigens or antigenic fragments or variants thereof is from a cancer cell or a pathogen, wherein the pathogen is selected from bacteria, fungi, parasite or virus, wherein the virus is not a T cell leukemia virus, wherein the Tax protein is from HTLV-2.

2. The dendritic cell of claim 1, wherein the dendritic cell has a constitutive maturation and activation phenotype.

3. The dendritic cell of claim 1, wherein the dendritic cell is a human cell.

4. The dendritic cell of claim 1, wherein the dendritic cell expresses one or more dendritic cell maturation and activation markers.

5. The dendritic cell claim 1, wherein the antigen is a cancer antigen.

6. The dendritic cell of claim 1, wherein the cell presents the antigen in an HLA-restricted manner.

7. The dendritic cell of claim 1, wherein the antigen is introduced by viral transduction.

8. The dendritic cell of claim 7, wherein the virus is a lentivirus.

9. The dendritic cell of claim 1, wherein the dendritic cell is capable of priming naive lymphocytes to generate cytotoxic lymphocytes that recognize antigen.

10. A method for producing cytotoxic T lymphocytes, comprising culturing dendritic cells of claim 1 together with cells comprising naive lymphocytes for a period of time, whereby cytotoxic T lymphocytes are produced.

11. The method of claim 10, wherein the cytotoxic T lymphocytes are antigen specific and induce cytolysis of target cells in an HLA-restricted manner.

12. A method of treating a disease or condition in a subject, comprising administering to the subject an effective amount of cytotoxic T lymphocytes, wherein the cytotoxic T lymphocytes are produced by the method of claim 10.

13. A method of treating a disease or condition in a subject, comprising administering to the subject an effective amount of a dendritic cell of claim 1.

14. An engineered primary blood dendritic cell, wherein the dendritic cell is genetically engineered to express a functional Tax protein from a T cell leukemia virus, wherein the dendritic cell is CD205+ and CD11c+, wherein the dendritic cell presents one or more antigens or antigenic fragments or variants thereof, wherein the Tax protein is from HTLV-2.

15. An engineered primary blood dendritic cell, wherein the dendritic cell is genetically engineered to express a functional Tax protein from a T cell leukemia virus, wherein the dendritic cell is CD205+ and CD11c+, wherein the dendritic cell presents one or more antigens or antigenic fragments or variants thereof, wherein the one or more antigens or antigenic fragments or variants thereof is human telomerase reverse transcriptase or an antigenic fragment or variant thereof.

* * * * *

SEQUENCE LISTING

<160> NUMBER OF SEQ ID NOS: 54

<210> SEQ ID NO 1
<211> LENGTH: 353
<212> TYPE: PRT
<213> ORGANISM: HTLV-1

<400> SEQUENCE: 1

```
Met Ala His Phe Pro Gly Phe Gly Gln Ser Leu Leu Phe Gly Tyr Pro
1               5                   10                  15

Val Tyr Val Phe Gly Asp Cys Val Gln Gly Asp Trp Cys Pro Ile Ser
            20                  25                  30

Gly Gly Leu Cys Ser Ala Arg Leu His Arg His Ala Leu Leu Ala Thr
        35                  40                  45

Cys Pro Glu His Gln Ile Thr Trp Asp Pro Ile Asp Gly Arg Val Ile
    50                  55                  60

Gly Ser Ala Leu Gln Phe Leu Ile Pro Arg Leu Pro Ser Phe Pro Thr
65                  70                  75                  80

Gln Arg Thr Ser Lys Thr Leu Lys Val Leu Thr Pro Pro Ile Thr His
                85                  90                  95

Thr Thr Pro Asn Ile Pro Pro Ser Phe Leu Gln Ala Met Arg Lys Tyr
            100                 105                 110

Ser Pro Phe Arg Asn Gly Tyr Met Glu Pro Thr Leu Gly Gln His Leu
        115                 120                 125

Pro Thr Leu Ser Phe Pro Asp Pro Gly Leu Arg Pro Gln Asn Leu Tyr
    130                 135                 140

Thr Leu Trp Gly Gly Ser Val Val Cys Met Tyr Leu Tyr Gln Leu Ser
145                 150                 155                 160

Pro Pro Ile Thr Trp Pro Leu Leu Pro His Val Ile Phe Cys His Pro
                165                 170                 175

Gly Gln Leu Gly Ala Phe Leu Thr Asn Val Pro Tyr Lys Arg Ile Glu
            180                 185                 190

Glu Leu Leu Tyr Lys Ile Ser Leu Thr Thr Gly Ala Leu Ile Ile Leu
        195                 200                 205

Pro Glu Asp Cys Leu Pro Thr Thr Leu Phe Gln Pro Ala Arg Ala Pro
    210                 215                 220

Val Thr Leu Thr Ala Trp Gln Asn Gly Leu Leu Pro Phe His Ser Thr
225                 230                 235                 240

Leu Thr Thr Pro Gly Leu Ile Trp Thr Phe Thr Asp Gly Thr Pro Met
```

```
                  245                 250                 255
Ile Ser Gly Pro Cys Pro Lys Asp Gly Gln Pro Ser Leu Val Leu Gln
            260                 265                 270

Ser Ser Ser Phe Ile Phe His Lys Phe Gln Thr Lys Ala Tyr His Pro
        275                 280                 285

Ser Phe Leu Leu Ser His Gly Leu Ile Gln Tyr Ser Ser Phe His Ser
    290                 295                 300

Leu His Leu Leu Phe Glu Glu Tyr Thr Asn Ile Pro Ile Ser Leu Leu
305                 310                 315                 320

Phe Asn Glu Lys Glu Ala Asp Asp Asn Asp His Glu Pro Gln Ile Ser
                325                 330                 335

Pro Gly Gly Leu Glu Pro Pro Ser Glu Lys His Phe Arg Glu Thr Glu
            340                 345                 350

Val
```

<210> SEQ ID NO 2
<211> LENGTH: 1062
<212> TYPE: DNA
<213> ORGANISM: HTLV-1

<400> SEQUENCE: 2

```
atggcccatt tcccagggtt tggacagagt cttcttttcg atacccagt ctacgtgttt      60
ggagactgtg tacaaggcga ctggtgcccc atctctgggg gactatgttc ggcccgccta    120
catcgtcacg ccctactggc cacctgtcca gagcatcaga tcacctggga ccccatcgac    180
ggacgcgtta tcggctcagc tctacagttc cttatccctc gactcccctc cttcccacc     240
cagagaacct ctaagaccct caaggtcctt accccgccaa tcactcatac aaccccaac    300
attccaccct cctcctcca ggccatgcgc aaatactccc ccttccgaaa tggatacatg    360
gaacccaccc ttgggcagca cctcccaacc ctgtctttc cagaccccgg actccggccc    420
caaaacctgt acaccctctg ggaggctcc gttgtctgca tgtacctcta ccagctttcc    480
ccccccatca cctggccccct cctgccccac gtgattttt gccaccccgg ccagctcggg    540
gccttcctca ccaatgttcc ctacaagcga atagaagaac tcctctataa aatttccctc    600
accacagggg ccctaataat tctacccgaa gactgtttgc ccaccaccct tttccagcct    660
gctagggcac ccgtcacgct aacagcctgg caaaacggcc tccttccgtt ccactcaacc    720
ctcaccactc caggccttat tggacattt accgatggca cgcctatgat ttccgggccc    780
tgccctaaag atggccagcc atctttagta ctacagtcct cctcctttat atttcacaaa    840
tttcaaacca aggcctacca cccctcattt ctactctcac acggcctcat acagtactct    900
tcctttcata gtttacatct cctgtttgaa gaatacacca catcccccat ttctctactt    960
tttaacgaaa aagaggcaga tgacaatgac catgagcccc aaatatccc cgggggctta   1020
gagcctccca gtgaaaaaca tttccgagaa acagaagtct ga                      1062
```

<210> SEQ ID NO 3
<211> LENGTH: 331
<212> TYPE: PRT
<213> ORGANISM: HTLV-2

<400> SEQUENCE: 3

```
Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Val Ser
            20                  25                  30
```

Gly Gly Leu Cys Ser Thr Arg Leu His Arg His Ala Leu Leu Ala Thr
            35                  40                  45

Cys Pro Glu His Gln Leu Thr Trp Asp Pro Ile Asp Gly Arg Val Val
 50                  55                  60

Ser Ser Pro Leu Gln Tyr Leu Ile Pro Arg Leu Pro Ser Phe Pro Thr
 65                  70                  75                  80

Gln Arg Thr Ser Arg Thr Leu Lys Val Leu Thr Pro Thr Thr Pro
                85                  90                  95

Val Ser Pro Lys Val Pro Pro Ala Phe Phe Gln Ser Met Arg Lys His
                100                 105                 110

Thr Pro Tyr Arg Asn Gly Cys Leu Glu Pro Thr Leu Gly Asp Gln Leu
            115                 120                 125

Pro Ser Leu Ala Phe Pro Glu Pro Gly Leu Arg Pro Gln Asn Ile Tyr
    130                 135                 140

Thr Thr Trp Gly Lys Thr Val Val Cys Leu Tyr Leu Tyr Gln Leu Ser
145                 150                 155                 160

Pro Pro Met Thr Trp Pro Leu Ile Pro His Val Ile Phe Cys His Pro
                165                 170                 175

Arg Gln Leu Gly Ala Phe Leu Thr Lys Val Pro Leu Lys Arg Leu Glu
            180                 185                 190

Glu Leu Leu Tyr Lys Met Phe Leu His Thr Gly Thr Val Ile Val Leu
        195                 200                 205

Pro Val Asp Asp Leu Pro Thr Thr Met Phe Gln Pro Val Arg Ala Pro
    210                 215                 220

Cys Ile Gln Thr Ala Trp Cys Thr Gly Leu Leu Pro Tyr His Ser Ile
225                 230                 235                 240

Leu Thr Thr Pro Gly Leu Ile Trp Thr Phe Asn Asp Gly Ser Pro Met
                245                 250                 255

Ile Ser Gly Pro Cys Pro Lys Ala Gly Gln Pro Ser Leu Val Val Gln
            260                 265                 270

Ser Ser Leu Leu Ile Phe Glu Lys Phe Gln Thr Lys Ala Phe His Pro
        275                 280                 285

Ser Tyr Leu Leu Ser His Gln Leu Ile Gln Tyr Ser Ser Phe His Asn
    290                 295                 300

Leu His Leu Leu Phe Asp Glu Tyr Thr Asn Ile Pro Val Ser Ile Leu
305                 310                 315                 320

Phe Asn Lys Glu Glu Ala Asp Asn Gly Asp
                325                 330

<210> SEQ ID NO 4
<211> LENGTH: 996
<212> TYPE: DNA
<213> ORGANISM: HTLV-2

<400> SEQUENCE: 4
atggcccatt tcccaggatt tggacaaagc ctcctatatg ataccccgt  ctacgtgttt      60 ggcgattgtg tacaggccga ttggtgtccc gtctcaggtg gtctatgttc cacccgccta     120
catcgacatg cctcctggc  cacctgtcca gagcaccaac tcacctggga ccccatcgat     180
ggacgcgttg tcagctctcc tctccaatac cttatccctc gcctcccctc cttccccacc     240
cagagaacct caaggaccct caaggtcctt acccctccca ccactcctgt ctcccccaag     300
gttccacctg ccttctttca atcaatgcga aagcacaccc cctaccgaaa tggatgcctg     360
gaaccaaccc tcggggatca gctcccctcc ctcgccttcc ccgaacctgg cctccgtccc     420

```
caaaacatct acaccacctg gggaaaaacc gtagtatgcc tatacctata ccagctttcc    480
ccacccatga catggccact tatacccat gtcatattct gccacccag acaattagga    540 gccttcctca ccaaggtgcc tctaaaacga ttagaagaac ttctatacaa aatgttccta    600
cacacaggga cagtcatagt cctcccagtg gacgacctac ccaccacaat gttccaaccc    660
gtgagggctc cctgtatcca gactgcctgg tgtacaggac ttctccccta tcactccatc    720
ttaacaaccc caggtctaat atggaccttc aatgacggct caccaatgat ttccggccct    780
tgccccaaag cagggcagcc atctttagta gttcagtcct ccctattaat cttcgaaaaa    840
ttccaaacca aagccttcca tccctcctat ctactctctc atcagcttat acaatactcc    900
tccttccata accttcacct tctattcgat gaatacacca acatccctgt ctctatttta    960
tttaataaag aagaggcgga tgacaatggc gactga                             996
```

<210> SEQ ID NO 5
<211> LENGTH: 350
<212> TYPE: PRT
<213> ORGANISM: HTLV-3

<400> SEQUENCE: 5

```
Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Ile Ser
            20                  25                  30

Gly Gly Leu Cys Ser Ala Arg Leu His Arg His Ala Leu Leu Ala Thr
        35                  40                  45

Cys Pro Glu His Gln Ile Thr Trp Asp Pro Ile Asp Gly Arg Val Val
    50                  55                  60

Ser Ser Ala Leu Gln Tyr Leu Ile Pro Arg Leu Pro Ser Phe Pro Thr
65                  70                  75                  80

Gln Arg Thr Thr Arg Thr Leu Lys Val Leu Thr Pro Pro Thr Thr Ala
                85                  90                  95

Ala Thr Pro Lys Ile Pro Pro Ser Phe Phe His Ala Val Lys Lys His
            100                 105                 110

Thr Pro Phe Arg Asn Asn Cys Leu Glu Leu Thr Leu Gly Glu Gln Leu
        115                 120                 125

Pro Ala Met Ser Phe Pro Asp Pro Gly Leu Arg Pro Gln Asn Ile Tyr
    130                 135                 140

Thr Met Trp Gly Ser Ser Val Val Cys Leu Tyr Leu Tyr Gln Leu Ser
145                 150                 155                 160

Pro Pro Met Thr Trp Pro Leu Ile Pro His Val Ile Phe Cys His Pro
                165                 170                 175

Glu Gln Leu Gly Ala Phe Leu Thr Arg Val Pro Thr Lys Arg Leu Glu
            180                 185                 190

Glu Leu Leu Tyr Lys Ile Phe Leu Ser Thr Gly Ala Ile Ile Ile Leu
        195                 200                 205

Pro Glu Asn Cys Phe Pro Thr Thr Leu Phe Gln Pro Thr Arg Ala Pro
    210                 215                 220

Ala Val Gln Ala Pro Trp His Thr Gly Leu Leu Pro Cys Gln Lys Glu
225                 230                 235                 240

Ile Ala Thr Pro Gly Leu Ile Trp Thr Phe Thr Asp Gly Ser Pro Met
                245                 250                 255

Ile Ser Gly Pro Cys Pro Lys Glu Gly Gln Pro Ser Leu Val Val Gln
            260                 265                 270
```

Ser Ser Thr Phe Ile Phe Gln Gln Phe Gln Thr Lys Ala Ser His Pro
        275                 280                 285

Ala Phe Leu Leu Ser His Lys Leu Ile His Tyr Ser Ser Phe His Ser
        290                 295                 300

Leu His Leu Leu Phe Glu Glu Tyr Thr Thr Ile Pro Phe Ser Leu Leu
305                 310                 315                 320

Phe Asn Glu Lys Gly Ala Asn Val Asp Asp Glu Pro Arg Asp Gly
                325                 330                 335

Ser Gln Pro Pro Ala Arg Gly Gln Ile Ala Glu Ser Pro Val
        340                 345                 350

<210> SEQ ID NO 6
<211> LENGTH: 1053
<212> TYPE: DNA
<213> ORGANISM: HTLV-3

<400> SEQUENCE: 6
atggcccatt tcccaggttt cggacagagc cttctctacg gtaccctgt ctacgttttc      60 ggcgactgtg tacaggccga ttggtgcccc atttctgggg ggctttgttc cgctcggcta    120
caccgccatg cctactggc cacgtgcccc gaacatcaga ttacctggga ccccatcgat     180
ggacgcgttg tcagctcagc tctacaatac cttatccctc gactcccctc cttccccacc    240
cagagaacta cccgcaccct caaggttctc acccccccaa ccactgctgc gaccccaag    300 attcctccat ccttcttcca cgccgttaaa aaacacaccc ccttccgaaa caattgcctt    360
gaactcaccc tgggagagca gttgccagcc atgtccttcc ccgaccctgg gctccgaccc    420
caaaacatct acaccatgtg gggaagctcc gttgtgtgcc tttacctcta tcagctctcc    480
ccccccatga cctggcctct aatcccgcat gttatattct gccatcctga gcagcttgga    540
gccttcctca cccgagtccc taccaaacga ttagaagaac tcctgtataa gatattttta    600
agcacagggg cgataatcat cctgcctgaa aactgttttc aaccaccct gttccaaccc     660 acccgcgcgc ccgcggtgca ggccccctgg cacacaggcc tgctcccgtg tcaaaaggaa    720
attgctaccc ccgggctcat ttggactttc actgatggca gccccatgat tccggccct    780 tgccccaaag aaggacagcc atctttagta gtacaatcat ctacatttat cttttcaacaa  840 ttccaaacca aggccagtca ccccgctttc ctcttgtccc acaaactaat ccactactcc    900
tcttttcatt ccctccacct cctctttgag gaatatacaa ctatcccctt ttctctactt    960
tttaatgaaa aaggggcaaa tgtcgatgat gatgagcccc gagacgggtc acaaccacca   1020
gctagaggac aaatagctga gtcacccgtc tga                                1053

<210> SEQ ID NO 7
<211> LENGTH: 345
<212> TYPE: PRT
<213> ORGANISM: HTLV-4

<400> SEQUENCE: 7

Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Ile Ser
            20                  25                  30

Gly Gly Leu Cys Ser Pro Arg Leu His Arg His Ala Leu Leu Ala Thr
        35                  40                  45

Cys Pro Glu His Gln Ile Thr Trp Asp Pro Ile Asp Gly Arg Val Val
    50                  55                  60

Gly Ser Pro Leu Gln Tyr Leu Ile Pro Arg Leu Pro Ser Phe Pro Thr
65                  70                  75                  80

Gln Arg Thr Ser Lys Thr Leu Lys Val Leu Thr Pro Thr Thr Pro
            85                  90                  95

Val Thr Pro Lys Val Pro Pro Ser Phe Phe Gln Ser Val Arg Arg His
            100                 105                 110

Ser Pro Tyr Arg Asn Gly Cys Leu Glu Thr Thr Leu Gly Glu Gln Leu
            115                 120                 125

Pro Ser Leu Ala Phe Pro Glu Pro Gly Leu Arg Pro Gln Asn Val Tyr
        130                 135                 140

Thr Ile Trp Gly Lys Thr Ile Val Cys Leu Tyr Ile Tyr Gln Leu Ser
145                 150                 155                 160

Pro Pro Met Thr Trp Pro Leu Ile Pro His Val Ile Phe Cys Asn Pro
                165                 170                 175

Arg Gln Leu Gly Ala Phe Leu Ser Asn Val Pro Pro Lys Arg Leu Glu
                180                 185                 190

Glu Leu Leu Tyr Lys Leu Tyr Leu His Thr Gly Ala Ile Ile Ile Leu
            195                 200                 205

Pro Glu Asp Ala Leu Pro Thr Thr Leu Phe Gln Pro Val Arg Ala Pro
    210                 215                 220

Cys Val Gln Thr Thr Trp Asn Thr Gly Leu Leu Pro Tyr Gln Pro Asn
225                 230                 235                 240

Leu Thr Thr Pro Gly Leu Ile Trp Thr Phe Asn Asp Gly Ser Pro Met
                245                 250                 255

Ile Ser Gly Pro Cys Pro Lys Ala Gly Gln Pro Ser Leu Val Val Gln
                260                 265                 270

Ser Ser Leu Leu Ile Phe Glu Arg Phe Gln Thr Lys Ala Tyr His Pro
            275                 280                 285

Ser Tyr Leu Leu Ser His Gln Leu Ile Gln Tyr Ser Ser Phe His His
        290                 295                 300

Leu Tyr Leu Leu Phe Asp Glu Tyr Thr Thr Ile Pro Phe Ser Leu Leu
305                 310                 315                 320

Phe Lys Glu Lys Glu Gly Asp Asp Arg Asp Asn Asp Pro Leu Pro Gly
                325                 330                 335

Ala Thr Ala Ser Pro Gln Gly Gln Asn
            340                 345

<210> SEQ ID NO 8
<211> LENGTH: 1038
<212> TYPE: DNA
<213> ORGANISM: HTLV-4

<400> SEQUENCE: 8
atggcccact tcccaggatt cgggcagagc ctcctctatg atacccccgt ctatgtgttt    60
ggcgattgtg ttcaagccga ttggtgcccc atctccggtg gattatgctc ccccgccta   120 catcgccacg ccctcctggc cacctgcccc gagcaccaga tcacctggga ccccatcgat   180
ggacgagttg tcggctcgcc tctccaatac cttatccctc gcctcccctc cttcccacc    240 caacgaacct ccaagaccct caaagtcctt accccaccaa ccactcctgt cacccccaag   300
gttccaccct ccttctttca gtccgtgcgg aggcacagcc cctaccgcaa cggatgtctt   360
gaaacaaccc ttggagagca gctccccctcc cttgcatttc ctgagccagg cctcaggccc   420
caaaacgtct acaccatctg gggaaagacc atagtgtgtc tatacatcta ccagctgtcc   480

```
cctcccatga cctggcccct cattccccat gtcatatttt gcaacccag gcagcttggc      540 gcttttctaa gcaatgtgcc ccccaagcga ttagaagaac tcctctacaa actttatcta      600
cacaccggcg ccataatcat cctgccggaa gacgccctgc ctaccaccct atttcagcct      660
gttcgagcac cctgtgtcca aactacctgg aacacaggac ttctcccata ccagccaaac      720
ctgactaccc ctggcctgat atggaccttt aatgatgggt ctcctatgat ttcaggacct      780
tgccctaagg cagggcagcc atccttggta gtacagtcct cactactaat cttcgagaga      840
tttcaaacca agcctatca tccctcttac ctcctctccc accaattgat acagtattcc      900
tccttccatc acctctactt actctttgat gaatatacta ctatcccctt ctctctacta      960
tttaaggaaa agagggaga tgacaggac aacgaccctc tcccagggc gacagcaagc    1020 cccaaggac aaaactag                                                   1038
```

<210> SEQ ID NO 9
<211> LENGTH: 1069
<212> TYPE: PRT
<213> ORGANISM: Homo sapiens

<400> SEQUENCE: 9

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270
```

-continued

```
Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
        290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                    325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                    405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
        450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                    485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
        530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                    565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
        610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                    645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
```

690             695             700
Glu Leu Tyr Phe Val Lys Val Asp Val Thr Gly Ala Tyr Asp Thr Ile
705             710             715             720

Pro Gln Asp Arg Leu Thr Glu Val Ile Ala Ser Ile Ile Lys Pro Gln
            725             730             735

Asn Thr Tyr Cys Val Arg Arg Tyr Ala Val Val Gln Lys Ala Ala His
            740             745             750

Gly His Val Arg Lys Ala Phe Lys Ser His Val Ser Thr Leu Thr Asp
            755             760             765

Leu Gln Pro Tyr Met Arg Gln Phe Val Ala His Leu Gln Glu Thr Ser
770             775             780

Pro Leu Arg Asp Ala Val Val Ile Glu Gln Ser Ser Leu Asn Glu
785             790             795             800

Ala Ser Ser Gly Leu Phe Asp Val Phe Leu Arg Phe Met Cys His His
            805             810             815

Ala Val Arg Ile Arg Gly Lys Ser Tyr Val Gln Cys Gln Gly Ile Pro
            820             825             830

Gln Gly Ser Ile Leu Ser Thr Leu Leu Cys Ser Leu Cys Tyr Gly Asp
            835             840             845

Met Glu Asn Lys Leu Phe Ala Gly Ile Arg Arg Asp Gly Leu Leu Leu
850             855             860

Arg Leu Val Asp Asp Phe Leu Leu Val Thr Pro His Leu Thr His Ala
865             870             875             880

Lys Thr Phe Leu Ser Tyr Ala Arg Thr Ser Ile Arg Ala Ser Leu Thr
            885             890             895

Phe Asn Arg Gly Phe Lys Ala Gly Arg Asn Met Arg Arg Lys Leu Phe
            900             905             910

Gly Val Leu Arg Leu Lys Cys His Ser Leu Phe Leu Asp Leu Gln Val
            915             920             925

Asn Ser Leu Gln Thr Val Cys Thr Asn Ile Tyr Lys Ile Leu Leu Leu
930             935             940

Gln Ala Tyr Arg Phe His Ala Cys Val Leu Gln Leu Pro Phe His Gln
945             950             955             960

Gln Val Trp Lys Asn Pro Thr Phe Phe Leu Arg Val Ile Ser Asp Thr
            965             970             975

Ala Ser Leu Cys Tyr Ser Ile Leu Lys Ala Lys Asn Ala Gly Met Ser
            980             985             990

Leu Gly Ala Lys Gly Ala Ala Gly Pro Leu Pro Ser Glu Ala Val Gln
            995             1000            1005

Trp Leu Cys His Gln Ala Phe Leu Leu Lys Leu Thr Arg His Arg
    1010            1015            1020

Val Thr Tyr Val Pro Leu Leu Gly Ser Leu Arg Thr Ala Gln Thr
    1025            1030            1035

Gln Leu Ser Arg Lys Leu Pro Gly Thr Thr Leu Thr Ala Leu Glu
    1040            1045            1050

Ala Ala Ala Asn Pro Ala Leu Pro Ser Asp Phe Lys Thr Ile Leu
    1055            1060            1065

Asp

<210> SEQ ID NO 10
<211> LENGTH: 3210
<212> TYPE: DNA
<213> ORGANISM: Homo sapiens

<400> SEQUENCE: 10

```
atgccgcgcg ctccccgctg ccgagccgtg cgctccctgc tgcgcagcca ctaccgcgag    60
gtgctgccgc tggccacgtt cgtgcggcgc ctggggcccc agggctggcg gctggtgcag   120
cgcggggacc cggcggcttt ccgcgcgctg gtggcccagt gcctggtgtg cgtgccctgg   180
gacgcacggc cgccccccgc cgccccctcc ttccgccagg tgtcctgcct gaaggagctg   240
gtggcccgag tgctgcagag gctgtgcgag cgcggcgcga gaacgtgct ggccttcggc    300
ttcgcgctgc tggacggggc ccgcggggc ccccccgagg ccttcaccac cagcgtgcgc    360
agctacctgc ccaacacggt gaccgacgca ctgcggggga gcgggggcgtg ggggctgctg   420
ctgcgccgcg tgggcgacga cgtgctggtt cacctgctgg cacgctgcgc gctctttgtg   480
ctggtggctc ccagctgcgc ctaccaggtg tgcgggccgc cgctgtacca gctcggcgct   540
gccactcagg cccggccccc gccacacgct agtggacccc gaaggcgtct gggatgcgaa   600
cgggcctgga accatagcgt cagggaggcc ggggtccccc tgggcctgcc agccccgggt   660
gcgaggaggc gcggggcag tgccagccga agtctgccgt tgcccaagag gcccaggcgt    720
ggcgctgccc ctgagccgga gcggacgccc gttgggcagg ggtcctgggc ccacccgggc   780
aggacgcgtg gaccgagtga ccgtggtttc tgtgtggtgt cacctgccag acccgccgaa   840
gaagccacct cttttggaggg tgcgctctct ggcacgcgcc actcccaccc atccgtgggc   900
cgccagcacc acgcgggccc cccatccaca tcgcggccac cacgtccctg ggacacgcct   960
tgtcccccgg tgtacgccga gaccaagcac ttcctctact cctcaggcga caaggagcag  1020
ctgcggccct ccttcctact cagctctctg aggcccagcc tgactggcgc tcggaggctc  1080
gtggagacca tctttctggg ttccaggccc tggatgccag ggactccccg caggttgccc  1140
cgcctgcccc agcgctactg gcaaatgcgg cccctgtttc tggagctgct ggggaaccac  1200
gcgcagtgcc cctacggggt gctcctcaag acgcactgcc cgctgcgagc tgcggtcacc  1260
ccagcagccg tgtctgtgc ccgggagaag ccccagggct ctgtggcggc ccccgaggag   1320
gaggacacag accccccgtcg cctggtgcag ctgctccgcc agcacagcag ccctggcag   1380
gtgtacggct tcgtgcgggc ctgcctgcgc ggctggtgc ccccaggcct ctggggctcc   1440
aggcacaacg aacgccgctt cctcaggaac accaagaagt tcatctccct ggggaagcat  1500
gccaagctct cgctgcagga gctgacgtgg aagatgagcg tgcgggactg cgcttggctg  1560
cgcaggagcc cagggggttgg ctgtgttccg gccgcagagc accgtctgcg tgaggagatc  1620
ctggccaagt tcctgcactg gctgatgagt gtgtacgtcg tcgagctgct caggtctttc  1680
ttttatgtca cggagaccac gtttcaaaag aacaggctct ttttctaccg gaagagtgtc  1740
tggagcaagt tgcaaagcat tggaatcaga cagcacttga gagggtgca gctgcgggag  1800
ctgtcggaag cagaggtcag gcagcatcgg gaagccaggc ccgccctgct gacgtccaga  1860
ctccgcttca tccccaagcc tgacgggctg cggccgattg tgaacatgga ctacgtcgtg  1920
ggagccagaa cgttccgcag agaaaagagg gccgagcgtc tcacctcgag ggtgaaggca  1980
ctgttcagcg tgctcaacta cgagcgggcg cggcgccccg gcctcctggg cgcctctgtg  2040
ctgggcctgg acgatatcca cagggcctgg cgcaccttcg tgctgcgtgt gcgggcccag  2100
gacccgccgc ctgagctgta ctttgtcaag gtggatgtga cgggcgcgta cgacaccatc  2160
ccccaggaca ggctcacgga ggtcatcgcc agcatcatca accccagaa cacgtactgc  2220
gtgcgtcggt atgccgtggt ccagaaggcc gcccatggga cgtccgcaa ggccttcaag  2280
agccacgtct ctaccttgac agacctccag ccgtacatgc gacagttcgt ggctcacctg  2340
```

```
caggagacca gcccgctgag ggatgccgtc gtcatcgagc agagctcctc cctgaatgag   2400
gccagcagtg gcctcttcga cgtcttccta cgcttcatgt gccaccacgc cgtgcgcatc   2460
aggggcaagt cctacgtcca gtgccagggg atcccgcagg gctccatcct ctccacgctg   2520
ctctgcagcc tgtgctacgg cgacatggag aacaagctgt tgcggggat tcggcgggac   2580 gggctgctcc tgcgtttggt ggatgatttc ttgttggtga cacctcacct cacccacgcg   2640
aaaaccttcc tcagctatgc ccggacctcc atcagagcca gtctcacctt caaccgcggc   2700
ttcaaggctg gaggaacat gcgtcgcaaa ctctttgggg tcttgcggct gaagtgtcac   2760
agcctgtttc tggatttgca ggtgaacagc ctccagacgg tgtgcaccaa catctacaag   2820
atcctcctgc tgcaggcgta caggtttcac gcatgtgtgc tgcagctccc atttcatcag   2880
caagtttgga agaaccccac attttttcctg cgcgtcatct ctgacacggc ctccctctgc   2940
tactccatcc tgaaagccaa gaacgcaggg atgtcgctgg gggccaaggg cgccgccggc   3000
cctctgccct ccgaggccgt gcagtggctg tgccaccaag cattcctgct caagctgact   3060
cgacaccgtg tcacctacgt gccactcctg gggtcactca ggacagccca gacgcagctg   3120
agtcggaagc tcccggggac gacgctgact gccctggagg ccgcagccaa cccggcactg   3180
ccctcagact tcaagaccat cctggactga                                    3210

<210> SEQ ID NO 11
<211> LENGTH: 317
<212> TYPE: PRT
<213> ORGANISM: Homo sapiens

<400> SEQUENCE: 11

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
                20                  25                  30

Gly Leu Asp Ser Met Lys Asp Glu Glu Tyr Glu Gln Met Val Lys Glu
            35                  40                  45

Leu Gln Glu Ile Arg Leu Glu Pro Gln Glu Val Pro Arg Gly Ser Glu
        50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
```

210                 215                 220
Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Leu Gly Gln Leu
                260                 265                 270

Thr Leu Glu Asn Leu Gln Met Leu Pro Glu Ser Glu Asp Glu Ser
            275                 280                 285

Tyr Asp Thr Glu Ser Glu Phe Thr Glu Phe Thr Glu Asp Leu Pro
            290                 295                 300

Tyr Asp Asp Cys Val Phe Gly Gly Gln Arg Leu Thr Leu
305                 310                 315

<210> SEQ ID NO 12
<211> LENGTH: 954
<212> TYPE: DNA
<213> ORGANISM: Homo sapiens

<400> SEQUENCE: 12

```
atgttccagg cggccgagcg cccccaggag tgggccatgg agggcccccg cgacgggctg     60
aagaaggagc ggctactgga cgaccgccac gacagcggcc tggactccat gaaagacgag    120
gagtacgagc agatggtcaa ggagctgcag gagatccgcc tcgagccgca ggaggtgccg    180
cgcggctcgg agccctggaa gcagcagctc accgaggacg ggactcgtt cctgcacttg    240
gccatcatcc atgaagaaaa ggcactgacc atggaagtga tccgccaggt gaagggagac    300
ctggcttttcc tcaacttcca gaacaacctg cagcagactc cactccactt ggctgtgatc    360
accaaccagc agaaattgc tgaggcactt ctggggagctg ctgtgatcc tgagctccga    420
gactttcgag gaaatacccc cctacacctt gcctgtgagc agggctgcct ggccagcgtg    480
ggagtcctga ctcagtcctg caccaccccg cactccact ccatcctgaa ggctaccaac    540
tacaatggcc acacgtgtct acacttagcc tctatccatg gctacctggg catcgtggag    600
cttttggtgt ccttgggtgc tgatgtcaat gctcaggagc cctgtaatgg ccggactgcc    660
cttcacctcg cagtggacct gcaaaatcct gacctggtgt cactcctgtt gaagtgtggg    720
gctgatgtca acagagttac ctaccagggc tattctcccct accagctcac ctggggccgc    780
ccaagcaccc ggatacagca gcagctgggc cagctgacac tagaaaacct tcagatgctg    840
ccagagagtg aggatgagga gagctatgac acagagtcag agttcacgga gttcacagag    900
gacgagctgc cctatgatga ctgtgtgttt ggaggccagc gtctgacgtt atga    954
```

<210> SEQ ID NO 13
<211> LENGTH: 719
<212> TYPE: PRT
<213> ORGANISM: artificial sequence
<220> FEATURE:
<223> OTHER INFORMATION: Fusion protein

<400> SEQUENCE: 13

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
                20                  25                  30

Gly Leu Asp Ser Met Lys Asp Glu Glu Tyr Glu Gln Met Val Lys Glu
            35                  40                  45

-continued

```
Leu Gln Glu Ile Arg Leu Glu Pro Gln Glu Val Pro Arg Gly Ser Glu
 50                  55                  60

Pro Trp Lys Gln Gln Leu Thr Glu Asp Gly Asp Ser Phe Leu His Leu
 65                  70                  75                  80

Ala Ile Ile His Glu Glu Lys Ala Leu Thr Met Glu Val Ile Arg Gln
                 85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
            115                 120                 125

Ala Leu Leu Gly Ala Gly Cys Asp Pro Glu Leu Arg Asp Phe Arg Gly
130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
            195                 200                 205

Val Asn Ala Gln Glu Pro Cys Asn Gly Arg Thr Ala Leu His Leu Ala
210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
            245                 250                 255

Thr Trp Gly Arg Pro Ser Thr Arg Ile Gln Gln Leu Gly Gln Leu
            260                 265                 270

Thr Leu Glu Asn Leu Gln Met Leu Pro Glu Ser Glu Asp Glu Glu Ser
            275                 280                 285

Tyr Asp Thr Glu Ser Glu Phe Thr Glu Phe Thr Glu Asp Glu Leu Pro
            290                 295                 300

Tyr Asp Asp Cys Val Phe Gly Gly Gln Arg Leu Thr Leu Gly Ser Arg
305                 310                 315                 320

Gln His His Ala Gly Pro Pro Ser Thr Ser Arg Pro Arg Pro Trp
            325                 330                 335

Asp Thr Pro Cys Pro Pro Val Tyr Ala Glu Thr Lys His Phe Leu Tyr
            340                 345                 350

Ser Ser Gly Asp Lys Glu Gln Leu Arg Pro Ser Phe Leu Leu Ser Ser
            355                 360                 365

Leu Arg Pro Ser Leu Thr Gly Ala Arg Arg Leu Val Glu Thr Ile Phe
370                 375                 380

Leu Gly Ser Arg Pro Trp Met Pro Gly Thr Pro Arg Arg Leu Pro Arg
385                 390                 395                 400

Leu Pro Gln Arg Tyr Trp Gln Met Arg Pro Leu Phe Leu Glu Leu Leu
            405                 410                 415

Gly Asn His Ala Gln Cys Pro Tyr Gly Val Leu Leu Lys Thr His Cys
            420                 425                 430

Pro Leu Arg Ala Ala Val Thr Pro Ala Ala Gly Val Cys Ala Arg Glu
            435                 440                 445

Lys Pro Gln Gly Ser Val Ala Ala Pro Glu Glu Glu Asp Thr Asp Pro
450                 455                 460

Arg Arg Leu Val Gln Leu Leu Arg Gln His Ser Ser Pro Trp Gln Val
```

```
                      465                 470                 475                 480
Tyr Gly Phe Val Arg Ala Cys Leu Arg Arg Leu Val Pro Pro Gly Leu
                485                 490                 495

Trp Gly Ser Arg His Asn Glu Arg Arg Phe Leu Arg Asn Thr Lys Lys
                500                 505                 510

Phe Ile Ser Leu Gly Lys His Ala Lys Leu Ser Leu Gln Glu Leu Thr
                515                 520                 525

Trp Lys Met Ser Val Arg Asp Cys Ala Trp Leu Arg Arg Ser Pro Gly
                530                 535                 540

Val Gly Cys Val Pro Ala Ala Glu His Arg Leu Arg Glu Ile Leu
545                 550                 555                 560

Ala Lys Phe Leu His Trp Leu Met Ser Val Tyr Val Glu Leu Leu
                565                 570                 575

Arg Ser Phe Phe Tyr Val Thr Glu Thr Thr Phe Gln Lys Asn Arg Leu
                580                 585                 590

Phe Phe Tyr Arg Lys Ser Val Trp Ser Lys Leu Gln Ser Ile Gly Ile
                595                 600                 605

Arg Gln His Leu Lys Arg Val Gln Leu Arg Glu Leu Ser Glu Ala Glu
                610                 615                 620

Val Arg Gln His Arg Glu Ala Arg Pro Ala Leu Leu Thr Ser Arg Leu
625                 630                 635                 640

Arg Phe Ile Pro Lys Pro Asp Gly Leu Arg Pro Ile Val Asn Met Asp
                645                 650                 655

Tyr Val Val Gly Ala Arg Thr Phe Arg Arg Glu Lys Arg Ala Glu Arg
                660                 665                 670

Leu Thr Ser Arg Val Lys Ala Leu Phe Ser Val Leu Asn Tyr Glu Arg
                675                 680                 685

Ala Arg Arg Pro Gly Leu Leu Gly Ala Ser Val Leu Gly Leu Asp Asp
                690                 695                 700

Ile His Arg Ala Trp Arg Thr Phe Val Leu Arg Val Arg Ala Gln
705                 710                 715

<210> SEQ ID NO 14
<211> LENGTH: 2160
<212> TYPE: DNA
<213> ORGANISM: artificial sequence
<220> FEATURE:
<223> OTHER INFORMATION: fusion construct

<400> SEQUENCE: 14
atgttccagg cggccgagcg ccccccaggag tgggccatgg agggcccccg cgacgggctg     60
aagaaggagc ggctactgga cgaccgccac gacagcggcc tggactccat gaaagacgag    120
gagtacgagc agatggtcaa ggagctgcag gagatccgcc tcgagccgca ggaggtgccg    180
cgcggctcgg agccctggaa gcagcagctc accgaggacg gggactcgtt cctgcacttg    240
gccatcatcc atgaagaaaa ggcactgacc atgaagtga tccgccaggt gaagggagac    300
ctggccttcc tcaacttcca gaacaacctg cagcagactc actccacttg gctgtgatc    360 accaaccagc cagaaattgc tgaggcactt ctgggagctg ctgtgatcc tgagctccga    420 gactttcgag gaaataccccc cctacacctt gcctgtgagc agggctgcct ggccagcgtg    480
ggagtcctga ctcagtcctg caccacccccg cacctccact ccatcctgaa ggctaccaac    540
tacaatggcc acacgtgtct acacttagcc tctatccatg ctacctggg catcgtggag    600 cttttggtgt ccttgggtgc tgatgtcaat gctcaggagc cctgtaatgg ccggactgcc    660
```

```
cttcacctcg cagtggacct gcaaaatcct gacctggtgt cactcctgtt gaagtgtggg      720
gctgatgtca acagagttac ctaccagggc tattctccct accagctcac ctggggccgc      780
ccaagcaccc ggatacagca gcagctgggc cagctgacac tagaaaacct tcagatgctg      840
ccagagagtg aggatgagga gagctatgac acagagtcag agttcacgga gttcacagag      900
gacgagctgc cctatgatga ctgtgtgttt ggaggccagc gtctgacgtt aggatcccgc      960
cagcaccacg cgggcccccc atccacatcg cggccaccac gtccctggga cacgccttgt     1020
cccccggtgt acgccgagac caagcacttc ctctactcct caggcgacaa ggagcagctg     1080
cggccctcct tcctactcag ctctctgagg cccagcctga ctggcgctcg gaggctcgtg     1140
gagaccatct ttctgggttc caggccctgg atgccaggga ctccccgcag gttgccccgc     1200
ctgccccagc gctactggca aatgcggccc ctgtttctgg agctgcttgg aaccacgcg     1260
cagtgcccct acggggtgct cctcaagacg cactgcccgc tgcgagctgc ggtcaccca     1320
gcagccggtg tctgtgcccg ggagaagccc cagggtctg tggcggcccc cgaggaggag     1380
gacacagacc cccgtcgcct ggtgcagctg ctccgccagc acagcagccc ctggcaggtg     1440
tacggcttcg tgcgggcctg cctgcgccgg ctggtgcccc caggcctctg gggctccagg     1500
cacaacgaac gccgcttcct caggaacacc aagaagttca tctccctggg gaagcatgcc     1560
aagctctcgc tgcaggagct gacgtggaag atgagcgtgc gggactgcgc ttggctgcgc     1620
aggagcccag gggttggctg tgttccggcc gcagagcacc gtctgcgtga ggagatcctg     1680
gccaagttcc tgcactggct gatgagtgtg tacgtcgtcg agctgctcag gtctttcttt     1740
tatgtcacgg agaccacgtt tcaaaagaac aggctctttt tctaccggaa gagtgtctgg     1800
agcaagttgc aaagcattgg aatcagacag cacttgaaga gggtgcagct gcgggagctg     1860
tcggaagcag aggtcaggca gcatcgggaa gccaggcccg ccctgctgac gtccagactc     1920
cgcttcatcc ccaagcctga cgggctgcgg ccgattgtga acatggacta cgtcgtggga     1980
gccagaacgt tccgcagaga aaagagggcc gagcgtctca cctcgagggt gaaggcactg     2040
ttcagcgtgc tcaactacga gcgggcgcgg cgccccggcc tcctgggcgc tctgtgctg     2100
ggcctggacg atatccacag ggcctggcgc accttcgtgc tgcgtgtgcg ggcccagtga   2160
```

<210> SEQ ID NO 15
<211> LENGTH: 365
<212> TYPE: PRT
<213> ORGANISM: Homo sapiens

<400> SEQUENCE: 15

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
            115                 120                 125

Ser Asp Trp Arg Phe Leu Arg Gly Tyr His Gln Tyr Ala Tyr Asp Gly
            130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
            165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
            210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
            290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
            325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 16
<211> LENGTH: 498
<212> TYPE: PRT
<213> ORGANISM: artificial sequence
<220> FEATURE:
<223> OTHER INFORMATION: fusion protein

<400> SEQUENCE: 16

Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Val Ser
            20                  25                  30

Gly Gly Leu Cys Ser Thr Arg Leu His Arg His Ala Leu Leu Ala Thr
            35                  40                  45

Cys Pro Glu His Gln Leu Thr Trp Asp Pro Ile Asp Gly Arg Val Val
            50                  55                  60

Ser Ser Pro Leu Gln Tyr Leu Ile Pro Arg Leu Pro Ser Phe Pro Thr
65                  70                  75                  80

Gln Arg Thr Ser Arg Thr Leu Lys Val Leu Thr Pro Thr Thr Pro
            85                  90                  95

Val Ser Pro Lys Val Pro Pro Ala Phe Phe Gln Ser Met Arg Lys His
            100                 105                 110

Thr Pro Tyr Arg Asn Gly Cys Leu Glu Pro Thr Leu Gly Asp Gln Leu
        115                 120                 125

Pro Ser Leu Ala Phe Pro Glu Pro Gly Leu Arg Pro Gln Asn Ile Tyr
    130                 135                 140

Thr Thr Trp Gly Lys Thr Val Val Cys Leu Tyr Leu Tyr Gln Leu Ser
145                 150                 155                 160

Pro Pro Met Thr Trp Pro Leu Ile Pro His Val Ile Phe Cys His Pro
                165                 170                 175

Arg Gln Leu Gly Ala Phe Leu Thr Lys Val Pro Leu Lys Arg Leu Glu
            180                 185                 190

Glu Leu Leu Tyr Lys Met Phe Leu His Thr Gly Thr Val Ile Val Leu
        195                 200                 205

Pro Val Asp Asp Leu Pro Thr Thr Met Phe Gln Pro Val Arg Ala Pro
    210                 215                 220

Cys Ile Gln Thr Ala Trp Cys Thr Gly Leu Leu Pro Tyr His Ser Ile
225                 230                 235                 240

Leu Thr Thr Pro Gly Leu Ile Trp Thr Phe Asn Asp Gly Ser Pro Met
                245                 250                 255

Ile Ser Gly Pro Cys Pro Lys Ala Gly Gln Pro Ser Leu Val Val Gln
            260                 265                 270

Ser Ser Leu Leu Ile Phe Glu Lys Phe Gln Thr Lys Ala Phe His Pro
        275                 280                 285

Ser Tyr Leu Leu Ser His Gln Leu Ile Gln Tyr Ser Ser Phe His Asn
    290                 295                 300

Leu His Leu Leu Phe Asp Glu Tyr Thr Asn Ile Pro Val Ser Ile Leu
305                 310                 315                 320

Phe Asn Lys Glu Glu Ala Asp Asp Asn Gly Asp Gly Ser Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
    370                 375                 380

Lys Leu Pro Val Pro Trp Pro Thr Leu Val Thr Thr Leu Thr Tyr Gly
385                 390                 395                 400

Val Gln Cys Phe Ser Arg Tyr Pro Asp His Met Lys Gln His Asp Phe
                405                 410                 415

Phe Lys Ser Ala Met Pro Glu Gly Tyr Val Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
    450                 455                 460

Glu Asp Gly Asn Ile Leu Gly His Lys Leu Glu Tyr Asn Tyr Asn Ser
465                 470                 475                 480

His Asn Val Tyr Ile Met Ala Asp Lys Gln Lys Asn Gly Ile Lys Val
                485                 490                 495

Asn Phe

<210> SEQ ID NO 17
<211> LENGTH: 1497
<212> TYPE: DNA
<213> ORGANISM: artificial sequence
<220> FEATURE:
<223> OTHER INFORMATION: fusion construct

<400> SEQUENCE: 17

```
atggcccatt tcccaggatt tggacaaagc ctcctatatg gatacccgt ctacgtgttt      60
ggcgattgtg tacaggccga ttggtgtccc gtctcaggtg gtctatgttc cacccgccta    120
catcgacatg ccctcctggc cacctgtcca gagcaccaac tcacctggga ccccatcgat    180
ggacgcgttg tcagctctcc tctccaatac cttatccctc gctcccctc cttccccacc    240
cagagaacct caaggaccct caaggtcctt acccctccca ccactcctgt ctccccaag    300
gttccacctg ccttctttca atcaatgcga aagcacaccc cctaccgaaa tggatgcctg    360
gaaccaaccc tcggggatca gctcccctcc ctcgccttcc ccgaacctgg cctccgtccc    420
caaaacatct acaccacctg gggaaaaacc gtagtatgcc tatacctata ccagcttttcc    480
ccacccatga catggccact tatacccat gtcatattct gccacccag acaattagga    540
gccttcctca ccaaggtgcc tctaaaacga ttagaagaac ttctatacaa aatgttccta    600
cacacaggga cagtcatagt cctcccagtg gacgacctac ccaccacaat gttccaaccc    660
gtgagggctc cctgtatcca gactgcctgg tgtacaggac ttctcccta tcactccatc    720
ttaacaaccc caggtctaat atggaccttc aatgacggct caccaatgat ttccggccct    780
tgccccaaag cagggcagcc atctttagta gttcagtcct ccctattaat cttcgaaaaa    840
ttccaaacca aagccttcca tccctcctat ctactctctc atcagcttat acaatactcc    900
tccttccata accttcacct tctattcgat gaatacacca acatccctgt ctctattta     960
tttaataaag aagaggcgga tgacaatggc gacggatccg tgagcaaggg cgaggagctg   1020
ttcaccgggg tggtgcccat cctggtcgag ctggacggcg acgtaaacgg ccacaagttc   1080
agcgtgtccg gcgagggcga gggcgatgcc acctacggca agctgaccct gaagttcatc   1140
tgcaccaccg gcaagctgcc cgtgccctgg cccaccctcg tgaccaccct gacctacggc   1200
gtgcagtgct tcagccgcta ccccgaccac atgaagcagc acgacttctt caagtccgcc   1260
atgcccgaag gctacgtcca ggagcgcacc atcttcttca aggacgacgg caactacaag   1320
acccgcgccg aggtgaagtt cgagggcgac accctggtga accgcatcga gctgaagggc   1380
atcgacttca aggaggacgg caacatcctg ggcacaagc tggagtacaa ctacaacagc   1440
cacaacgtct atatcatggc cgacaagcag aagaacggca tcaaggtgaa cttctaa      1497
```

<210> SEQ ID NO 18
<211> LENGTH: 24
<212> TYPE: DNA
<213> ORGANISM: artificial sequence
<220> FEATURE:
<223> OTHER INFORMATION: probe

<400> SEQUENCE: 18

```
gatccttctg ggaattccta gatc                                             24
```

<210> SEQ ID NO 19
<211> LENGTH: 25
<212> TYPE: DNA
<213> ORGANISM: artificial sequence
<220> FEATURE:
<223> OTHER INFORMATION: probe

<400> SEQUENCE: 19

```
gatccggcag gggaatctcc ctctc                                            25
```

-continued

```
<210> SEQ ID NO 20
<211> LENGTH: 21
<212> TYPE: DNA
<213> ORGANISM: artificial sequence
<220> FEATURE:
<223> OTHER INFORMATION: probe

<400> SEQUENCE: 20
cgcttgatga ctcagccgga a                                              21

<210> SEQ ID NO 21
<211> LENGTH: 20
<212> TYPE: DNA
<213> ORGANISM: artificial sequence
<220> FEATURE:
<223> OTHER INFORMATION: primer

<400> SEQUENCE: 21
gcaccgtcaa ggctgagaac                                                20

<210> SEQ ID NO 22
<211> LENGTH: 19
<212> TYPE: DNA
<213> ORGANISM: artificial sequence
<220> FEATURE:
<223> OTHER INFORMATION: primer

<400> SEQUENCE: 22
tggtgaagac gccagtgga                                                 19

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
cagtgctgct gaaggagatg                                                20

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
aacaagtttg gatgggcaac                                                20

<210> SEQ ID NO 25
<211> LENGTH: 20
<212> TYPE: DNA
<213> ORGANISM: artificial sequence
<220> FEATURE:
<223> OTHER INFORMATION: primer

<400> SEQUENCE: 25
tggcaatgag gatgacttgt                                                20

<210> SEQ ID NO 26
<211> LENGTH: 19
<212> TYPE: DNA
<213> ORGANISM: artificial sequence
<220> FEATURE:
<223> OTHER INFORMATION: primer
```

```
<400> SEQUENCE: 26
tggtggtcgg agattcgta                                              19

<210> SEQ ID NO 27
<211> LENGTH: 22
<212> TYPE: DNA
<213> ORGANISM: artificial sequence
<220> FEATURE:
<223> OTHER INFORMATION: primer

<400> SEQUENCE: 27
ctcaccagga tgctcacatt ta                                          22

<210> SEQ ID NO 28
<211> LENGTH: 22
<212> TYPE: DNA
<213> ORGANISM: artificial sequence
<220> FEATURE:
<223> OTHER INFORMATION: primer

<400> SEQUENCE: 28
cctccagagg tttgagttct tc                                          22

<210> SEQ ID NO 29
<211> LENGTH: 19
<212> TYPE: DNA
<213> ORGANISM: artificial sequence
<220> FEATURE:
<223> OTHER INFORMATION: primer

<400> SEQUENCE: 29
ggagacttgc ctggtgaaa                                              19

<210> SEQ ID NO 30
<211> LENGTH: 21
<212> TYPE: DNA
<213> ORGANISM: artificial sequence
<220> FEATURE:
<223> OTHER INFORMATION: primer

<400> SEQUENCE: 30
ctggcttgtt cctcactact c                                           21

<210> SEQ ID NO 31
<211> LENGTH: 18
<212> TYPE: DNA
<213> ORGANISM: artificial sequence
<220> FEATURE:
<223> OTHER INFORMATION: primer

<400> SEQUENCE: 31
ctggccgtgg ctctcttg                                               18

<210> SEQ ID NO 32
<211> LENGTH: 20
<212> TYPE: DNA
<213> ORGANISM: artificial sequence
<220> FEATURE:
<223> OTHER INFORMATION: primer

<400> SEQUENCE: 32
ccttggcaaa actgcacctt                                             20

<210> SEQ ID NO 33
```

```
<211> LENGTH: 20
<212> TYPE: DNA
<213> ORGANISM: artificial sequence
<220> FEATURE:
<223> OTHER INFORMATION: primer

<400> SEQUENCE: 33
tttccctgac ctccctctaa                                                    20

<210> SEQ ID NO 34
<211> LENGTH: 22
<212> TYPE: DNA
<213> ORGANISM: artificial sequence
<220> FEATURE:
<223> OTHER INFORMATION: primer

<400> SEQUENCE: 34
cgagacactg gaaggtgaat ta                                                 22

<210> SEQ ID NO 35
<211> LENGTH: 22
<212> TYPE: DNA
<213> ORGANISM: artificial sequence
<220> FEATURE:
<223> OTHER INFORMATION: primer

<400> SEQUENCE: 35
ccttgtggct accctggtcc tc                                                 22

<210> SEQ ID NO 36
<211> LENGTH: 22
<212> TYPE: DNA
<213> ORGANISM: artificial sequence
<220> FEATURE:
<223> OTHER INFORMATION: primer

<400> SEQUENCE: 36
ctcagcaggt tttgggagtg gt                                                 22

<210> SEQ ID NO 37
<211> LENGTH: 20
<212> TYPE: DNA
<213> ORGANISM: artificial sequence
<220> FEATURE:
<223> OTHER INFORMATION: primer

<400> SEQUENCE: 37
accagagcag tgaggtctta                                                    20

<210> SEQ ID NO 38
<211> LENGTH: 22
<212> TYPE: DNA
<213> ORGANISM: artificial sequence
<220> FEATURE:
<223> OTHER INFORMATION: primer

<400> SEQUENCE: 38
ctcctttgtg acaggtgtac tg                                                 22

<210> SEQ ID NO 39
<211> LENGTH: 22
<212> TYPE: DNA
<213> ORGANISM: artificial sequence
<220> FEATURE:
<223> OTHER INFORMATION: primer

<400> SEQUENCE: 39
```
gagtccggag atgcaagtat tc                                              22

<210> SEQ ID NO 40
<211> LENGTH: 22
<212> TYPE: DNA
<213> ORGANISM: artificial sequence
<220> FEATURE:
<223> OTHER INFORMATION: primer

<400> SEQUENCE: 40
cctccagttc ctcacattct tt                                              22

<210> SEQ ID NO 41
<211> LENGTH: 20
<212> TYPE: DNA
<213> ORGANISM: artificial sequence
<220> FEATURE:
<223> OTHER INFORMATION: primer

<400> SEQUENCE: 41
acccacagcc tggataacag                                                 20

<210> SEQ ID NO 42
<211> LENGTH: 20
<212> TYPE: DNA
<213> ORGANISM: artificial sequence
<220> FEATURE:
<223> OTHER INFORMATION: primer

<400> SEQUENCE: 42
actggttgcc atcaaactcc                                                 20

<210> SEQ ID NO 43
<211> LENGTH: 22
<212> TYPE: DNA
<213> ORGANISM: artificial sequence
<220> FEATURE:
<223> OTHER INFORMATION: primer

<400> SEQUENCE: 43
tcaatctctt cagcacaaag ga                                              22

<210> SEQ ID NO 44
<211> LENGTH: 20
<212> TYPE: DNA
<213> ORGANISM: artificial sequence
<220> FEATURE:
<223> OTHER INFORMATION: primer

<400> SEQUENCE: 44
atcacacagg cttccaggtc                                                 20

<210> SEQ ID NO 45
<211> LENGTH: 20
<212> TYPE: DNA
<213> ORGANISM: artificial sequence
<220> FEATURE:
<223> OTHER INFORMATION: primer

<400> SEQUENCE: 45
tctcctgttg tgcttctcca                                                 20

<210> SEQ ID NO 46
<211> LENGTH: 22
<212> TYPE: DNA

```
<213> ORGANISM: artificial sequence
<220> FEATURE:
<223> OTHER INFORMATION: primer

<400> SEQUENCE: 46
gtcaaagttc atcctgtcct tg                                              22

<210> SEQ ID NO 47
<211> LENGTH: 20
<212> TYPE: DNA
<213> ORGANISM: artificial sequence
<220> FEATURE:
<223> OTHER INFORMATION: primer

<400> SEQUENCE: 47
gccgaattcc ggatctacaa                                                 20

<210> SEQ ID NO 48
<211> LENGTH: 21
<212> TYPE: DNA
<213> ORGANISM: artificial sequence
<220> FEATURE:
<223> OTHER INFORMATION: primer

<400> SEQUENCE: 48
ctcctggagc acctgataaa c                                               21

<210> SEQ ID NO 49
<211> LENGTH: 22
<212> TYPE: DNA
<213> ORGANISM: artificial sequence
<220> FEATURE:
<223> OTHER INFORMATION: primer

<400> SEQUENCE: 49
cccatgggtt gtgtgtttat tt                                              22

<210> SEQ ID NO 50
<211> LENGTH: 21
<212> TYPE: DNA
<213> ORGANISM: artificial sequence
<220> FEATURE:
<223> OTHER INFORMATION: primer

<400> SEQUENCE: 50
aaaccggcag taactggata g                                               21

<210> SEQ ID NO 51
<211> LENGTH: 22
<212> TYPE: DNA
<213> ORGANISM: artificial sequence
<220> FEATURE:
<223> OTHER INFORMATION: primer

<400> SEQUENCE: 51
gatccctgac atctggaatc tg                                              22

<210> SEQ ID NO 52
<211> LENGTH: 22
<212> TYPE: DNA
<213> ORGANISM: artificial sequence
<220> FEATURE:
<223> OTHER INFORMATION: primer

<400> SEQUENCE: 52
gaaacatctg gagagaggaa gg                                              22
```

```
<210> SEQ ID NO 53
<211> LENGTH: 20
<212> TYPE: DNA
<213> ORGANISM: artificial sequence
<220> FEATURE:
<223> OTHER INFORMATION: primer

<400> SEQUENCE: 53
cagaggagga acgagctaaa                                              20

<210> SEQ ID NO 54
<211> LENGTH: 20
<212> TYPE: DNA
<213> ORGANISM: artificial sequence
<220> FEATURE:
<223> OTHER INFORMATION: primer

<400> SEQUENCE: 54
ttggacggac aggatgtatg                                              20
```